US008507240B2

(12) United States Patent
Lassen et al.

(10) Patent No.: US 8,507,240 B2
(45) Date of Patent: *Aug. 13, 2013

(54) HAFNIA PHYTASE VARIANTS

(75) Inventors: Soeren Flensted Lassen, Farum (DK); Leonardo De Maria, Frederiksberg (DK); Lars Kobberoee Skov, Ballerup (DK); Esben Peter Friis, Herlev (DK); Tomoko Matsui, Chiba (JP); Allan Noergaard, Chiba (JP); Jesper Vind, Vaerloese (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/472,822

(22) Filed: May 16, 2012

(65) Prior Publication Data

US 2012/0225468 A1  Sep. 6, 2012

Related U.S. Application Data

(62) Division of application No. 12/568,312, filed on Sep. 28, 2009, now Pat. No. 8,206,962.

(60) Provisional application No. 61/100,784, filed on Sep. 29, 2008.

(30) Foreign Application Priority Data

Sep. 26, 2008 (EP) ..................... 08165245

(51) Int. Cl.
  C12N 9/16 (2006.01)
  A23K 1/165 (2006.01)
  A23L 1/105 (2006.01)
  A23L 1/20 (2006.01)

(52) U.S. Cl.
  USPC ............... 435/196; 426/28; 426/31; 426/54; 426/623; 426/630; 426/635

(58) Field of Classification Search
  None
  See application file for complete search history.

(56) References Cited

U.S. PATENT DOCUMENTS

| | | | | |
|---|---|---|---|---|
| 6,511,699 B1* | 1/2003 | Lei | | 426/630 |
| 6,841,370 B1* | 1/2005 | Lei | | 435/196 |
| 7,238,378 B2* | 7/2007 | Matsui et al. | | 426/52 |
| 7,923,232 B2 | 4/2011 | Lassen et al. | | |
| 8,053,221 B2 | 11/2011 | Miasnikov et al. | | |
| 8,101,391 B2* | 1/2012 | Sjoeholm et al. | | 435/196 |
| 8,143,045 B2* | 3/2012 | Miasnikov et al. | | 435/196 |
| 8,143,046 B2* | 3/2012 | Cervin et al. | | 435/196 |
| 8,206,962 B2* | 6/2012 | Lassen et al. | | 435/195 |
| 2003/0103958 A1 | 6/2003 | Short et al. | | |
| 2005/0010037 A1 | 1/2005 | Wu et al. | | |
| 2010/0136113 A1* | 6/2010 | Steer et al. | | 424/484 |
| 2013/0017185 A1* | 1/2013 | De Maria et al. | | 424/94.6 |

FOREIGN PATENT DOCUMENTS

| | | |
|---|---|---|
| WO | 03/066847 A2 | 8/2003 |
| WO | 2006/043178 A2 | 4/2006 |
| WO | 2008/092901 A2 | 8/2008 |
| WO | 2008/097619 A2 | 8/2008 |
| WO | 2008/116878 A1 | 10/2008 |

OTHER PUBLICATIONS

Greaves et al., Nature, vol. 200, pp. 1231-1232 (1963).
Gu et al., Chinese J. Biotech., vol. 23, No. 6, pp. 1017-1021 (2007).
Huang et al., Biochemical and Biophysical Research Communications, vol. 350, No. 4, pp. 884-889 (2006).
Kim et al., Appl. Microbiol. Biotechnol., vol. 79, pp. 751-758 (2008).
Lehmann et al., Current Opinion in Biotechnology, vol. 12, pp. 371-375 (2001).
Lim et al., Nature Structural Biology, vol. 7, No. 2, pp. 108-113 (2000).
Mullaney et al., Biochemical and Biophysical Research Communications, vol. 328, No. 2, pp. 404-408 (2005).
Ryan et al., Computer Methods and Programs in Biomedicine, vol. 85, No. 1, pp. 69-76 (2006).
Shi et al., Aquaculture, vol. 275, Nos. 1-4, pp. 70-75 (2008).
Yoon et al., Enzyme and Microbial Technology, vol. 18, No. 6, pp. 449-454 (1996).
Zinin et al., Biotekhnolgiya vol. 2, pp. 3-10 (2003).
Zinin et al., Biosis Accession No. PREV200300308051 (2003).
Zinin et al., FEMS Microbiology Letters, vol. 236, No. 2, pp. 283-290 (2004).

* cited by examiner

*Primary Examiner* — Manjunath Rao
*Assistant Examiner* — William W Moore
(74) *Attorney, Agent, or Firm* — Elias Lambiris

(57) ABSTRACT

The present invention relates to phytases having at least 76% identity to a phytase derived from *Hafnia alvei* and comprises at least one modification in the amino acid sequence thereof. These phytase variants have modified, preferably improved, properties, such as, reduced protease sensibility, preferably they exhibit improved properties in respect of thermal performance, such as heat-stability (temperature stability, thermostability), steam stability, pelleting stability and/or temperature profile; and/or protease stability, in particular pepsin stability, pH profile, specific activity, substrate specificity, performance in animal feed (such as an improved release and/or degradation of phytate), susceptibility to glycation, and/or glycosylation pattern. The invention also relates to DNA encoding these phytases, methods of their production, as well as the use thereof, e.g., in animal feed and animal feed additives.

16 Claims, No Drawings

SEQUENCE LISTING

```
<160> NUMBER OF SEQ ID NOS: 2

<210> SEQ ID NO 1
<211> LENGTH: 1338
<212> TYPE: DNA
<213> ORGANISM: Hafnia alvei
<220> FEATURE:
<221> NAME/KEY: CDS
<222> LOCATION: (1)..(1338)
<220> FEATURE:
<221> NAME/KEY: sig_peptide
<222> LOCATION: (1)..(99)
<220> FEATURE:
<221> NAME/KEY: mat_peptide
<222> LOCATION: (100)..(1338)

<400> SEQUENCE: 1 atg aca atc tct ctg ttt aac cgt aat aaa ccc gct att gca cag cgt    48
Met Thr Ile Ser Leu Phe Asn Arg Asn Lys Pro Ala Ile Ala Gln Arg
        -30                 -25                 -20 att tta tgt cct ctg atc gtg gct tta ttc tca ggt tta ccg gca tac    96
Ile Leu Cys Pro Leu Ile Val Ala Leu Phe Ser Gly Leu Pro Ala Tyr
    -15                 -10                  -5 gcc agt gat acc gcc cct gct ggg ttc cag ttg gaa aag gtt gtt atc   144
Ala Ser Asp Thr Ala Pro Ala Gly Phe Gln Leu Glu Lys Val Val Ile
 -1   1               5                  10                  15 cta agc aga cat ggt gta cgc gcg cca acc aaa atg aca caa acg atg   192
Leu Ser Arg His Gly Val Arg Ala Pro Thr Lys Met Thr Gln Thr Met
                20                  25                  30 cgc gac gtc aca cct cac cag tgg cct gaa tgg ccg gta aaa ctc ggc   240
Arg Asp Val Thr Pro His Gln Trp Pro Glu Trp Pro Val Lys Leu Gly
            35                  40                  45 tat atc acg cca cgc ggc gaa cat ctg att agc ctg atg ggc ggt ttt   288
Tyr Ile Thr Pro Arg Gly Glu His Leu Ile Ser Leu Met Gly Gly Phe
```

-continued

```
                50                   55                   60
tat cga gag cgc ttt cag caa caa ggt tta tta cct aag gat aac tgt    336
Tyr Arg Glu Arg Phe Gln Gln Gln Gly Leu Leu Pro Lys Asp Asn Cys
    65                   70                   75 cct aca cca gat gcc gtg tat gtt tgg gca gac gtc gat caa cgc aca    384
Pro Thr Pro Asp Ala Val Tyr Val Trp Ala Asp Val Asp Gln Arg Thr
 80                   85                   90                   95 cgt aaa acc ggc gag gct ttc tta gca ggt ctt gct ccc cag tgt gat    432
Arg Lys Thr Gly Glu Ala Phe Leu Ala Gly Leu Ala Pro Gln Cys Asp
                    100                  105                  110 tta gcg atc cac cat cag caa aac act cag cag gcc gat ccg ctg ttc    480
Leu Ala Ile His His Gln Gln Asn Thr Gln Gln Ala Asp Pro Leu Phe
                115                  120                  125 cac cct gtg aaa gcc ggt att tgt tcg atg gat aaa tca cag gta cac    528
His Pro Val Lys Ala Gly Ile Cys Ser Met Asp Lys Ser Gln Val His
            130                  135                  140 gcc gcg gtt gaa aag cag gca ggc aca ccg att gag acg ctc aat caa    576
Ala Ala Val Glu Lys Gln Ala Gly Thr Pro Ile Glu Thr Leu Asn Gln
        145                  150                  155 cgc tat caa gcc tct tta gcg ctg atg agt tcg gta ctc gat ttt cca    624
Arg Tyr Gln Ala Ser Leu Ala Leu Met Ser Ser Val Leu Asp Phe Pro
160                  165                  170                  175 aaa tcc ccc tat tgt cag cag cac aac att ggc aaa ctc tgc gat ttt    672
Lys Ser Pro Tyr Cys Gln Gln His Asn Ile Gly Lys Leu Cys Asp Phe
                    180                  185                  190 tca cag gcg atg cct agc aga ctg gcg ata aat gac gac ggt aat aaa    720
Ser Gln Ala Met Pro Ser Arg Leu Ala Ile Asn Asp Asp Gly Asn Lys
                195                  200                  205 gtg gct ctc gaa ggt gcc gtg gga ctt gca tcg acg ttg gct gaa att    768
Val Ala Leu Glu Gly Ala Val Gly Leu Ala Ser Thr Leu Ala Glu Ile
            210                  215                  220 ttc ctg ctg gaa cac gct cag gga atg cct aaa gtg gct tgg ggg aat    816
Phe Leu Leu Glu His Ala Gln Gly Met Pro Lys Val Ala Trp Gly Asn
        225                  230                  235 att cac act gag cag caa tgg aac tct ctg ttg aaa ttg cat aat gcg    864
Ile His Thr Glu Gln Gln Trp Asn Ser Leu Leu Lys Leu His Asn Ala
240                  245                  250                  255 cag ttt gac ttg atg tcg cgc acg ccc tat atc gcc aag cat aac ggt    912
Gln Phe Asp Leu Met Ser Arg Thr Pro Tyr Ile Ala Lys His Asn Gly
                    260                  265                  270 act cca ctg ctg caa acc atc gcc cac gca ctg ggt tcc aat atc acg    960
Thr Pro Leu Leu Gln Thr Ile Ala His Ala Leu Gly Ser Asn Ile Thr
                275                  280                  285 agt cgc cca ctg ccg gat att tcg cca gac aat aag atc ctg ttt att   1008
Ser Arg Pro Leu Pro Asp Ile Ser Pro Asp Asn Lys Ile Leu Phe Ile
            290                  295                  300 gcc ggt cac gac acc aat att gcc aat att tct ggc atg tta ggg atg   1056
Ala Gly His Asp Thr Asn Ile Ala Asn Ile Ser Gly Met Leu Gly Met
        305                  310                  315 aca tgg aca ctt ccg gga caa cca gat aac acg cct ccg ggt ggc gct   1104
Thr Trp Thr Leu Pro Gly Gln Pro Asp Asn Thr Pro Pro Gly Gly Ala
320                  325                  330                  335 ttg gtg ttt gaa cgc tgg gta gat aac gcg ggg aaa ccg tat gtt agc   1152
Leu Val Phe Glu Arg Trp Val Asp Asn Ala Gly Lys Pro Tyr Val Ser
                    340                  345                  350 gtg aat atg gtg tat caa aca ctg gca cag ttg cac gac cag gcg ccg   1200
Val Asn Met Val Tyr Gln Thr Leu Ala Gln Leu His Asp Gln Ala Pro
                355                  360                  365 cta acg ttg cag cat cct gcg ggc agc gta cga cta aac ata ccg ggt   1248
Leu Thr Leu Gln His Pro Ala Gly Ser Val Arg Leu Asn Ile Pro Gly
```

```
                370             375             380
tgc agc gat caa acg ccc gat ggc tat tgc ccg ctc tcc acc ttc agc    1296
Cys Ser Asp Gln Thr Pro Asp Gly Tyr Cys Pro Leu Ser Thr Phe Ser
385                 390                 395 cgc tta gtc agc cac agc gtt gag cct gcg tgc cag ctt cct            1338
Arg Leu Val Ser His Ser Val Glu Pro Ala Cys Gln Leu Pro
400                 405                 410

<210> SEQ ID NO 2
<211> LENGTH: 446
<212> TYPE: PRT
<213> ORGANISM: Hafnia alvei

<400> SEQUENCE: 2

Met Thr Ile Ser Leu Phe Asn Arg Asn Lys Pro Ala Ile Ala Gln Arg
        -30                 -25                 -20

Ile Leu Cys Pro Leu Ile Val Ala Leu Phe Ser Gly Leu Pro Ala Tyr
        -15                 -10                  -5

Ala Ser Asp Thr Ala Pro Ala Gly Phe Gln Leu Glu Lys Val Val Ile
 -1  1               5                  10                  15

Leu Ser Arg His Gly Val Arg Ala Pro Thr Lys Met Thr Gln Thr Met
                20                  25                  30

Arg Asp Val Thr Pro His Gln Trp Pro Glu Trp Pro Val Lys Leu Gly
                35                  40                  45

Tyr Ile Thr Pro Arg Gly Glu His Leu Ile Ser Leu Met Gly Gly Phe
            50                  55                  60

Tyr Arg Glu Arg Phe Gln Gln Gln Gly Leu Leu Pro Lys Asp Asn Cys
 65                  70                  75

Pro Thr Pro Asp Ala Val Tyr Val Trp Ala Asp Val Asp Gln Arg Thr
 80                  85                  90                  95

Arg Lys Thr Gly Glu Ala Phe Leu Ala Gly Leu Ala Pro Gln Cys Asp
                100                 105                 110

Leu Ala Ile His His Gln Asn Thr Gln Gln Ala Asp Pro Leu Phe
                115                 120                 125

His Pro Val Lys Ala Gly Ile Cys Ser Met Asp Lys Ser Gln Val His
                130                 135                 140

Ala Ala Val Glu Lys Gln Ala Gly Thr Pro Ile Glu Thr Leu Asn Gln
145                 150                 155

Arg Tyr Gln Ala Ser Leu Ala Leu Met Ser Ser Val Leu Asp Phe Pro
160                 165                 170                 175

Lys Ser Pro Tyr Cys Gln His Asn Ile Gly Lys Leu Cys Asp Phe
            180                 185                 190

Ser Gln Ala Met Pro Ser Arg Leu Ala Ile Asn Asp Asp Gly Asn Lys
            195                 200                 205

Val Ala Leu Glu Gly Ala Val Gly Leu Ala Ser Thr Leu Ala Glu Ile
                210                 215                 220

Phe Leu Leu Glu His Ala Gln Gly Met Pro Lys Val Ala Trp Gly Asn
225                 230                 235

Ile His Thr Glu Gln Gln Trp Asn Ser Leu Leu Lys Leu His Asn Ala
240                 245                 250                 255

Gln Phe Asp Leu Met Ser Arg Thr Pro Tyr Ile Ala Lys His Asn Gly
            260                 265                 270

Thr Pro Leu Leu Gln Thr Ile Ala His Ala Leu Gly Ser Asn Ile Thr
            275                 280                 285

Ser Arg Pro Leu Pro Asp Ile Ser Pro Asp Asn Lys Ile Leu Phe Ile
            290                 295                 300
```

```
Ala Gly His Asp Thr Asn Ile Ala Asn Ile Ser Gly Met Leu Gly Met
    305             310             315
Thr Trp Thr Leu Pro Gly Gln Pro Asp Asn Thr Pro Pro Gly Gly Ala
320             325             330             335
Leu Val Phe Glu Arg Trp Val Asp Asn Ala Gly Lys Pro Tyr Val Ser
                340             345             350
Val Asn Met Val Tyr Gln Thr Leu Ala Gln Leu His Asp Gln Ala Pro
            355             360             365
Leu Thr Leu Gln His Pro Ala Gly Ser Val Arg Leu Asn Ile Pro Gly
        370             375             380
Cys Ser Asp Gln Thr Pro Asp Gly Tyr Cys Pro Leu Ser Thr Phe Ser
    385             390             395
Arg Leu Val Ser His Ser Val Glu Pro Ala Cys Gln Leu Pro
400             405             410
```

US 8,507,240 B2

HAFNIA PHYTASE VARIANTS

CROSS-REFERENCE TO RELATED APPLICATIONS

This application is a divisional of U.S. application Ser. No. 12/568,312 filed on Sep. 28, 2009, now U.S. Pat. No. 8,206,962, which claims priority or the benefit under 35 U.S.C. 119 of European application no. 08165245.5 filed Sep. 26, 2008 and U.S. provisional application No. 61/100,784 filed Sep. 29, 2008, the contents of which are fully incorporated herein by reference.

REFERENCE TO SEQUENCE LISTING

This application contains a Sequence Listing in the form of a text file, which is incorporated herein by reference.

FIELD OF THE INVENTION

The present invention relates to a phytase which has at least 76% identity to a phytase derived from *Hafnia alvei*, the amino acid sequence of which is shown in the appended sequence listing as SEQ ID NO: 2 and comprises at least one modification as compared to this phytase (i.e., is a variant thereof). The invention also relates to DNA encoding these phytases, nucleic acid constructs, vectors, and host cells comprising the polynucleotides as well as methods of their production, as well as the use thereof, e.g., in animal feed and animal feed additives.

BACKGROUND OF THE INVENTION

Background Art

Phytases are well-known enzymes, as are the advantages of adding them to foodstuffs for animals, including humans. Phytases have been isolated from various sources, including a number of fungal and bacterial strains.

It is an object of the present invention to provide alternative polypeptides having phytase activity (phytases) and polynucleotides encoding the polypeptides. The phytase variants of the invention exhibit modified or altered preferably improved properties as compared to the parent phytase. Non-limiting examples of such properties are: Stability (such as acid-stability, heat-stability, steam stability, pelleting stability, and/or protease stability, in particular pepsin stability), temperature profile, pH profile, specific activity, substrate specificity, performance in animal feed (such as an improved release and/or degradation of phytate), susceptibility to glycation, and/or glycosylation pattern.

A number of three-dimensional structures of phytases of the Histidine acid phosphate (HAP) type are known. (e.g., Lim et al., 2000, *Nature Struct. Biol.* 7: 108-113). These phytases are structurally related, but there are quite large differences in the amino acid sequences.

PCT/EP2008/053561 discloses the amino acid sequence of the wildtype HAP phytase of *Hafnia alvei* DSM 19197 (i.e., SEQ ID NO:2 herein), as SEQ ID NO:10 in PCT/EP2008/053561. The three-dimensional structure of the wildtype HAP phytase of *Hafnia alvei* DSM 19197 is also disclosed in PCT/EP2008/053561. The structure corresponds well with the known structures.

It is an object of the invention to provide phytases of modified, preferably, improved properties as compared to the parent or reference phytase from which they were derived.

Summary of Sequence Listing

In the sequence listing SEQ ID NO:1 and 2 provide DNA and amino acid sequences for the *Hafnia alvei* DSMZ 19197 phytase.

Summary of Examples

In the specification the following examples are provided:
Example 1: Preparation of variants, and determination of activity
Example 2: Specific activity
Example 3: Temperature stability
Example 4: Thermostability
Example 5: Temperature profile
Example 6: pH profile
Example 7: Steam Stability
Example 8: Glycation Residual activity
Example 9: Pelleting stability tests
Example 10: Performance in animal feed in an in vitro model for broilers
Example 11: Performance in an in vivo pig trial

SUMMARY OF THE INVENTION

The present invention relates to a phytase which has at least 76% identity to amino acid residues 1-413 of SEQ ID NO:2 and which comprises at least one modification in at least one position selected from the following: 139, 1, 4, 5, 6, 7, 8, 9, 10, 12, 16, 18, 25, 26, 27, 28, 29, 30, 31, 32, 33, 35, 36, 37, 38, 39, 40, 41, 45, 48, 49, 54, 55, 59, 63, 64, 66, 68, 69, 70, 71, 72, 74, 75, 76, 77, 78, 79, 80, 81, 82, 83, 89, 91, 92, 93, 95, 96, 97, 98, 100, 101, 103, 108, 109, 110, 111, 112, 113, 115, 116, 117, 118, 119, 120, 121, 122, 123, 124, 125, 126, 128, 130, 131, 132, 133, 134, 136, 137, 138, 140, 143, 144, 145, 146, 147, 148, 149, 150, 151, 152, 153, 154, 155, 156, 158, 159, 160, 161, 162, 163, 168, 172, 173, 175, 176, 177, 178, 179, 180, 181, 182, 183, 184, 185, 186, 187, 189, 190, 192, 193, 194, 195, 196, 198, 199, 200, 201, 202, 203, 204, 205, 206, 207, 208, 209, 211, 215, 217, 219, 221, 224, 227, 228, 230, 233, 234, 235, 236, 238, 239, 240, 241, 242, 243, 244, 245, 246, 247, 248, 249, 251, 256, 258, 259, 260, 261, 266, 268, 270, 279, 284, 285, 286, 287, 288, 289, 290, 292, 293, 294, 295, 296, 297, 298, 299, 301, 303, 304, 308, 310, 312, 313, 314, 316, 318, 319, 320, 322, 324, 325, 326, 331, 335, 343, 344, 345, 346, 347, 348, 354, 355, 356, 358, 360, 362, 363, 364, 365, 366, 367, 368, 369, 370, 371, 372, 373, 374, 375, 376, 378, 382, 383, 384, 385, 386, 387, 388, 389, 390, 391, 394, 395, 396, 397, 400, 401, 403, 404, 406, 408, 409, 411, 412, and 413, wherein the positions correspond to the positions of the phytase with the amino acids 1-413 of SEQ ID NO:2, with the proviso that the phytase is not the phytase with the amino acids 1-413 of SEQ ID NO:2.

The invention further relates to a phytase which has at least 76% identity to amino acid residues 1-413 of SEQ ID NO:2 and which comprises at least one modification in at least one position selected from the following: 139, 1, 4, 5, 6, 7, 8, 9, 10, 12, 16, 18, 25, 26, 27, 28, 29, 30, 31, 32, 33, 35, 36, 37, 38, 39, 40, 41, 45, 48, 49, 54, 55, 59, 63, 64, 66, 68, 69, 70, 71, 72, 74, 75, 76, 77, 78, 79, 80, 81, 82, 83, 89, 91, 92, 93, 95, 96, 97, 98, 100, 101, 103, 108, 109, 110, 111, 112, 113, 115, 116, 117, 118, 119, 120, 121, 122, 123, 124, 125, 126, 128, 130, 131, 132, 133, 134, 136, 137, 138, 140, 143, 144, 145, 146, 147, 148, 149, 150, 151, 152, 153, 154, 155, 156, 158, 159, 160, 161, 162, 163, 168, 172, 173, 175, 176, 177, 178, 179, 180, 181, 182, 183, 184, 185, 186, 187, 189, 190, 192, 193, 194, 195, 196, 198, 199, 200, 201, 202, 203, 204, 205, 206, 207, 208, 209, 211, 215, 217, 219, 221, 224, 227, 228, 230, 233, 234, 235, 236, 238, 239, 240, 241, 242, 243, 244, 245, 246, 247, 248, 249, 251, 256, 258, 259, 260, 261, 266, 268, 270, 279, 284, 285, 286, 287, 288, 289, 290, 292, 293, 294, 295, 296, 297, 298, 299, 301, 303, 304, 308, 310, 312, 313, 314, 316, 318, 319, 320, 322, 324, 325, 326, 331, 335, 343, 344, 345, 346, 347, 348, 354, 355, 356, 358, 360, 362, 363, 364, 365, 366, 367, 368, 369, 370, 371, 372, 373, 374, 375, 376, 378, 382, 383, 384, 385, 386, 387, 388, 389, 390, 391, 394, 395, 396, 397, 400, 401, 403, 404, 406, 408, 409, 411, 412, and 413; and at least one further modification in at least one position selected from the following: 1, 4, 5, 6, 7, 8, 9, 10, 12, 16, 18, 25, 26, 27, 28, 29, 30, 31, 32, 33, 35, 36, 37, 38, 39, 40, 41, 45, 48, 49, 54, 55, 59, 63, 64, 66, 68, 69, 70, 71, 72, 74, 75, 76, 77, 78, 79, 80, 81, 82, 83, 89, 91, 92, 93, 95, 96, 97, 98, 100, 101, 103, 108, 109, 110, 111, 112, 113, 115, 116, 117, 118, 119, 120, 121, 122, 123, 124, 125, 126, 128, 130, 131, 132, 133, 134, 136, 137, 138, 139, 140, 143, 144, 145, 146, 147, 148, 149, 150, 151, 152, 153, 154, 155, 156, 158, 159, 160, 161, 162, 163, 168, 172, 173, 175, 176, 177, 178, 179, 180, 181, 182, 183, 184, 185, 186, 187, 189, 190, 192, 193, 194, 195, 196, 198, 199, 200, 201, 202, 203, 204, 205, 206, 207, 208, 209, 211, 215, 217, 219, 221, 224, 227, 228, 230, 233, 234, 235, 236, 238, 239, 240, 241, 242, 243, 244, 245, 246, 247, 248, 249, 251, 256, 258, 259, 260, 261, 266, 268, 270, 279, 284, 285, 286, 287, 288, 289, 290, 292, 293, 294, 295, 296, 297, 298, 299, 301, 303, 304, 308, 310, 312, 313, 314, 316, 318, 319, 320, 322, 324, 325, 326, 331, 335, 343, 344, 345, 346, 347, 348, 354, 355, 356, 358, 360, 362, 363, 364, 365, 366, 367, 368, 369, 370, 371, 372, 373, 374, 375, 376, 378, 382, 383, 384, 385, 386, 387, 388, 389, 390, 391, 394, 395, 396, 397, 400, 401, 403, 404, 406, 408, 409, 411, 412, and 413, with the proviso that the phytase is not the phytase with the amino acids 1-413 of SEQ ID NO:2.

The invention also relates to a phytase which has at least 76% identity to amino acid residues 1-413 of SEQ ID NO:2 and which comprises at least one modification in at least one position selected from the following modifications: 8L,C, 9K,P,S, 10V, 12S,R, 16V, 18K, 25A, 26R,Q, 27A, 28A, 29P, R,K,A, 30P,L, 31I, 32Q,I,L, 33C,N, 35C, 36C, 37D,R,K, 38A, 41T, 45P, 48H,W,N, 49L, 54C,G, 55E, 59R,K, 63C, 66C, 68L, 69E,L, 70E, 74S, 75A, 76R,V, 77K,G,W, 78G,R, K,Q,S, 79L, 81E, 82S, 83G, 92Y, 93P,E,N, 95P,A, 96N,V, 97R, 100W, 101C, 103A, 109D, 111R,K,S, 112S, 115L,M, RK, 116S,T,N, 117A,Q, 118A,N,E,P,T, 119D,K,E, 120G,L, I,M, 121A,S,T,G,K, 122A,S,T,K, 123P,M,V,A,T, 128N,R, 130L, 131R, 132T,V, 134V, 136Q, 137L, 138N,V, 139C,R, 140P, 143C,V, 144R, 148R, 150C, 151D, 160G, 162N,R, 163P, 168V, 172C, 173N, 175N,S176C,Q, 177C, 178C,E 179C,L,W, 181L, 185R,K, 186S,T, 187E, 190N, 193R, 195L, 198E, 199C, 201C, 202A,K, 203Y, 206G,T,A, 207N,L, 208A, 209S, 211T,R, 215S, 217S,G, 219M,L, 221T,G, 224C, 227Q, 228C,Q, 230E, 234L,R,C,V, 235P, 236C, 239R, 243P, 244P, 245E, 246N, 247D, 248T, 249S,T, 251S,D,E,R, 256D, A, 258Y, 259C, 260L, 261F,Q,A, 268R, 270R, 284P, 285D, 286T, 287P, 288P, 293R,K,N, 298S, 299R, 301M, 308A, 310L, 312A, 313L, 314G, 316P,A, 318E, 319L, 320N, 325C, K, 326C, 331C,S,T, 335E, 343C, 344K, 346S,T, 347R, 348D, E,S,R 354L, 355S,T, 356F, 358C, 360P,Q, 362M, 363C,R,K, V, 365K, 366T, 368C, 369S, 370C, 374C,P, 376E, 378K, 380, 382S,T, 383N, 394N, 395E, 396D,E, 401N, 403N, and 411S.

The phytase variants of the invention exhibit modified or altered preferably improved properties as compared to the parent phytase. Non-limiting examples of such properties are: Stability (such as acid-stability, heat-stability, steam stability, and/or protease stability, in particular pepsin stability), temperature profile, pH profile, specific activity, substrate specificity, performance in animal feed (such as an improved release and/or degradation of phytate), susceptibility to glycation, and/or glycosylation pattern. The phytase variants of the invention preferably exhibit improved properties in respect of thermal performance, such as heat-stability (temperature stability, thermostability), steam stability, pelleting stability and/or temperature profile; and/or protease stability, in particular pepsin stability, pH profile, specific activity, substrate specificity, performance in animal feed (such as an improved release and/or degradation of phytate), susceptibility to glycation, and/or glycosylation pattern.

The invention also relates to DNA encoding these phytases, methods of their production, as well as the use thereof, e.g., in animal feed and animal feed additives.

DETAILED DESCRIPTION OF THE INVENTION

In a first aspect, the present invention relates to a phytase which has at least 76% identity to SEQ ID NO:2 and which comprises at least one modification in at least one position selected from the following: 139, 1, 4, 5, 6, 7, 8, 9, 10, 12, 16, 18, 25, 26, 27, 28, 29, 30, 31, 32, 33, 35, 36, 37, 38, 39, 40, 41, 45, 48, 49, 54, 55, 59, 63, 64, 66, 68, 69, 70, 71, 72, 74, 75, 76, 77, 78, 79, 80, 81, 82, 83, 89, 91, 92, 93, 95, 96, 97, 98, 100, 101, 103, 108, 109, 110, 111, 112, 113, 115, 116, 117, 118, 119, 120, 121, 122, 123, 124, 125, 126, 128, 130, 131, 132, 133, 134, 136, 137, 138, 140, 143, 144, 145, 146, 147, 148, 149, 150, 151, 152, 153, 154, 155, 156, 158, 159, 160, 161, 162, 163, 168, 172, 173, 175, 176, 177, 178, 179, 180, 181, 182, 183, 184, 185, 186, 187, 189, 190, 192, 193, 194, 195, 196, 198, 199, 200, 201, 202, 203, 204, 205, 206, 207, 208, 209, 211, 215, 217, 219, 221, 224, 227, 228, 230, 233, 234, 235, 236, 238, 239, 240, 241, 242, 243, 244, 245, 246, 247, 248, 249, 251, 256, 258, 259, 260, 261, 266, 268, 270, 279, 284, 285, 286, 287, 288, 289, 290, 292, 293, 294, 295, 296, 297, 298, 299, 301, 303, 304, 308, 310, 312, 313, 314, 316, 318, 319, 320, 322, 324, 325, 326, 331, 335, 343, 344, 345, 346, 347, 348, 354, 355, 356, 358, 360, 362, 363, 364, 365, 366, 367, 368, 369, 370, 371, 372, 373, 374, 375, 376, 378, 382, 383, 384, 385, 386, 387, 388, 389, 390, 391, 394, 395, 396, 397, 400, 401, 403, 404, 406, 408, 409, 411, 412, and 413. The percentage of identity is determined as described in the section "Phytase Polypeptides, Percentage of Identity".

The position numbers refer to the position numbering of SEQ ID NO:2, as described in the section "Position Numbering." Positions corresponding to these SEQ ID NO:2 position numbers in other phytases are determined as described in the section "Identifying Corresponding Position Numbers."

The phytase of the invention is a variant of the phytase of SEQ ID NO:2, viz. it is not identical to SEQ ID NO:2, as it comprises at least one modification as compared to SEQ ID NO:2.

In a preferred embodiment, the phytase of the invention comprises at least one of the following modifications: 8L,C, 9K,P,S, 10V, 12S,R, 16V, 18K, 25A, 26R,Q, 27A, 28A, 29P, R,K,A, 30P,L, 31I, 32Q,I,L, 33C,N, 35C, 36C, 37D,R,K, 38A, 41T, 45P, 48H,W,N, 49L, 54C,G, 55E, 59R,K, 63C, 66C, 68L, 69E,L, 70E, 74S, 75A, 76R,V, 77K,G,W, 78G,R, K,Q,S, 79L, 81E, 82S, 83G, 92Y, 93P,E,N, 95P,A, 96N,V, 97R, 100W, 101C, 103A, 109D, 111R,K,S, 112S, 115L,M, R,K, 116S,T,N, 117A,Q, 118A,N,E,P,T, 119D,K,E, 120G,L, I,M, 121A,S,T,G,K, 122A,S,T,K, 123P,M,V,A,T, 128N,R, 130L, 131R, 132T,V, 134V, 136Q, 137L, 138N,V, 139C,R, 140P, 143C,V, 144R, 148R, 150C, 151D, 160G, 162N,R, 163P, 168V, 172C, 173N, 175N,S 176C,Q, 177C, 178C,E 179C,L,W, 181L, 185R,K, 186S,T, 187E, 190N, 193R, 195L, 198E, 199C, 201C, 202A,K, 203Y, 206G,T,A, 207N,L, 208A, 209S, 211T,R, 215S, 217S,G, 219M,L, 221T,G, 224C, 227Q, 228C,Q, 230E, 234L,R,C,V, 235P, 236C, 239R, 243P, 244P, 245E, 246N, 247D, 248T, 249S,T, 251S,D,E,R, 256D, A, 258Y, 259C, 260L, 261F,Q,A, 268R, 270R, 284P, 285D, 286T, 287P, 288P, 293R,K,N, 298S, 299R, 301M, 308A, 310L, 312A, 313L, 314G, 316P,A, 318E, 319L, 320N, 325C, K, 326C, 331C,S,T, 335E, 343C, 344K, 346S,T, 347R, 348D, E,S,R 354L, 355S,T, 356F, 358C, 360P,Q, 362M, 363C,R,K, V, 365K, 366T, 368C, 369S, 370C, 374C,P, 376E, 378K, 380, 382S,T, 383N, 394N, 395E, 396D,E, 401N, 403N, and 411S.

The nomenclature used herein for modifications is described in detail in the section "Modifications, such as Substitutions, Deletions, Insertions."

Preferably the phytase of the invention exhibiting improved thermostability comprises at least one of the following modifications: 8C, 33C 35C, 36C, 54C, 63C, 66C, 101C, 139C, 143C, 201C, 150C, 172C, 176C, 177C, 178C, 179C, 224C, 228C, 236C, 259C, 325C, 326C, 331C, 343C, 358C, 363C, 368C, 370C, 374C. Specifically it comprises sets of modifications selected from the following: 8C/343C, 139C/201C, 179C/33C, 178C/33C, 172C/35C, 177C/36C, 176C/36C, 143C/201C, 54C/101C, 63C/368C, 66C/370C, 224C/236C, 150C/259C, 331C/326C, 358C/325C, 228C/363C, 368C/374C. The invention also comprises such combinations as 8C/343C in combination with 139C/201C, 179C/33C, 178C/33C, 172C/35C, 177C/36C, 176C/36C, 143C/201C, 54C/101C, 63C/368C, 66C/370C, 224C/236C, 150C/259C, 331C/326C, 358C/325C, 228C/363C, or 368C/374C. The invention also comprises such combinations as 139C/201C in combination with 179C/33C, 178C/33C, 172C/35C, 177C/36C, 176C/36C, 143C/201C, 54C/101C, 63C/368C, 66C/370C, 224C/236C, 150C/259C, 331C/326C, 358C/325C, 228C/363C, or 368C/374C. The invention also comprises such combinations as 179C/33C in combination with 178C/33C, 172C/35C, 177C/36C, 176C/36C, 143C/201C, 54C/101C, 63C/368C, 66C/370C, 224C/236C, 150C/259C, 331C/326C, 358C/325C, 228C/363C, or 368C/374C. The invention also comprises such combinations as 178C/33C in combination with 172C/35C, 177C/36C, 176C/36C, 143C/201C, 54C/101C, 63C/368C, 66C/370C, 224C/236C, 150C/259C, 331C/326C, 358C/325C, 228C/363C, or 368C/374C. The invention also comprises such combinations as 172C/35C in combination with 177C/36C, 176C/36C, 143C/201C, 54C/101C, 63C/368C, 66C/370C, 224C/236C, 150C/259C, 331C/326C, 358C/325C, 228C/363C, or 368C/374C. The invention also comprises such combinations as 177C/36C in combination with 176C/36C, 143C/201C, 54C/101C, 63C/368C, 66C/370C, 224C/236C, 150C/259C, 331C/326C, 358C/325C, 228C/363C, or 368C/374C. The invention also comprises such combinations as 176C/36C in combination with 143C/201C, 54C/101C, 63C/368C, 66C/370C, 224C/236C, 150C/259C, 331C/326C, 358C/325C, 228C/363C, or 368C/374C. The invention also comprises such combinations as 143C/201C in combination with 54C/101C, 63C/368C, 66C/370C, 224C/236C, 150C/259C, 331C/326C, 358C/325C, 228C/363C, or 368C/374C. The invention also comprises such combinations as 54C/101C in combination with 63C/368C, 66C/370C, 224C/236C, 150C/259C, 331C/326C, 358C/325C, 228C/363C, or 368C/374C. The invention also comprises such combinations as 63C/368C in combination with 66C/370C, 224C/236C, 150C/259C, 331C/326C, 358C/325C, 228C/363C, or 368C/374C. The invention also comprises such combinations as 66C/370C in combination with 224C/236C, 150C/259C, 331C/326C, 358C/325C, 228C/363C, or 368C/374C. The invention also comprises such combinations as 224C/236C in combination with 150C/259C, 331C/326C, 358C/325C, 228C/363C, or 368C/374C. The invention also comprises such combinations as 150C/259C in combination with 331C/326C, 358C/325C, 228C/363C, or 368C/374C. The invention also comprises such combinations as 331C/326C in combination with 358C/325C, 228C/363C, or 368C/374C. The invention also comprises such combinations as 358C/325C in combination with 228C/363C, or 368C/374C. The invention also comprises such combinations as 228C/363C in combination with 368C/3740.

In other embodiments for improving thermostability the phytase comprises a modification selected from the following: 29P, 30P, 93P, 95P, 140P, 163P, 235P, 243P, 244P, 284P, 287P, 288P, 316P, and 360P.

The phytase may also comprise a modification selected from the following: 8L, 9K, 12S, 16V, 27A, 30L, 32Q, 37D, 38A, 41T, 48W, 49L, 54G, 55E, 75A, 77K, 78G, 93E, 103A, 109D, 128N, 130L, 132T, 134V, 136Q, 137L, 173N, 176Q, 195L, 198E, 206T, 207N, 209S, 211T, 215S, 219M, 221T, 227Q, 228Q, 248T, 258Y, 260L, 261Q, 310L, 313L, 314G, 316A, 318E, 319L, 320N, 335E, 354L, 356F, 360Q, 362M, 251S, 363R, 365K, 366T, 369S, 374P, 376E, 378K, and 411S.

The phytase may also comprise a modification selected from the following: 9R, 29R,K, 37R,K, 59R,K, 69E, 70E, 78R,K, 81E, 93E, 111R,K, 115R,K, 119D, 185R,K, 230E, 239R, 245E, 251D,E, 293R,K, 348D,E, 363R,K, 395E, and 396D,E.

The phytase may also comprise a modification selected from the following: 12R, 25A, 26R, 28A, 29A, 30L, 45P, 48W, 76R, 97R, 117A, 118A, 119D, 120L, 121A, 122A, 131R, 139R, 148R, 176R, 179L, 187E, 202A, 206A, 207L, 219L, 234R, 251R, 261A, 268R, 270R, 299R, 347R, 256A, 308A, and 312A.

Further the efficacy of the phytase may be improved when it comprises a modification selected from the following: 31I, 120I, I134V, N202K, D203Y, and V208A.

In specific embodiments improving the efficiency of the phytase the amino acid residues between positions 180 and 189 have been replaced by small peptide having a length of 4, 5, 6, 7, or 8 amino acid residues, especially the pentapeptides QADKP, GEDKP, NGISA, IAGKS, KEKHQ, KEKQQ, KEKKV, or KTDKL, and or it also comprises that the amino acid residues between positions 115 and 124 have been replaced by a small peptide having a length of 5, 6, 7, 8, 9, 10 or 11 amino acid residues, especially the octatapeptide TQADTSSP.

In additional preferred embodiments, the phytase comprises the following combinations of modifications: 54C/55E/101C, 33C/178E/179C, and 33C/175S/176Q/178E/179C.

The phytase of the invention may be a variant of any wildtype or variant phytase.

Specifically for the phytase of SEQ ID NO:2 the following specific modifications are included:

M31I, 120I, I134V, N$_{202}$K, D203Y, V208A, Y179W, A221G, R321, R32L, D77G, D77W, T95A, D111S, K234C, K234V, K251S, H363V, H363R, D293R, Q93E, P348S, Q69L, Q245E, N78Q, K76V, G325K, G325G, A217G, A132T, and the following combination variants:

A132V/Q162R, A132V/Q181L, A132V/E211R, A132V/D83G, A132V/A217G, A132V/A217S, E100W/H363R D138V/Y48H, A132V/A217G, A132V/Q162R/Q181L/A217G, P348R/H363R, Q9S/D92Y, Q9P/L10V/D92Y/H115M, Q9P/L10V/D92Y/H115/L, D92Y/H115M, D92Y/H115M/L, D92Y/H115M, E100W/A217G/H363R, A217G/K251S, E100W/A217G/K251S, E100W/K251S, E100W/1555V/A217G, Q9S/E100W/R160G/A217G/H363R, D92Y/E100W/A217G/H363R, E100W/H115M/A217G/H363R, E100W/A217G/P348R/H363R, Q9S/A89A/D92Y/H115M/A217G/H363R, N78Q/E100W/A217G/H363R, K76V/N78Q/E100W/A217G/H363R, D83G/E100W/A217G/H363R, E100W/Y179W/A217G/H363R, E100W/

A217G/K234V/K251E/1286T/H363R, E100W/A217G/ K234V/P348R/H363R, Q9S/R18K/A89A/D92Y/H115M/ A217G/K234V/H363R, Q9S/D92Y/H115M/A217G/ K234V/H363R, Q9S/N78Q/D92Y/L112S/H115M/K234V/ P348R/H363R, Q9S/N78Q/A89A/D92Y/H115M/A132V/ Q162R/Q181L/A217G/K234V/P348R, Q9S/E54C/D92Y/ A101C/H143C/Q193R/I201C/A217G/H363R, E54C/N78S/ D92Y/A101C/H143C/L199C/A217G/H363R, E54C/ A101C/M168V/A217G/H363R, P82S/D92Y/E100W/ H143C/I201C/A217G/H363R, P82S/D92Y/E100W/ H143C/I201C/A217G/H363R, Q9S/N78Q/D92Y/L112S/ H115M/A217G/K234V/P348R/H363R, D92Y/A217G/ K234V/H363R, Y64S/D92Y/E100WN179W/A217G/ H363R, D92Y/A217G/H363R, Q9S/N78Q/A89A/D92Y/ H115M/A132V/H1430/Q162R/Q181L/I201C/A217G/ K234V/P348R, Q9S/N78Q/A89A/D92Y/H115M/A132V/ K139C/Q162R/Q181L/I201C/A217G/K234V/P348R, Q9S/ N78Q/A89A/D92Y/H115M/A132V/K139C/Q162R/ Q181L/L1990/A217G/K234V/L301M/P34 8R, Q9S/N78Q/ A89A/D92Y/H115M/A132V/Q162RN179W/Q181L/ A217G/K234V/P348R, D92Y/E100W/A217G/H363R/+ D33CN179C, D92Y/E100W/A217G/H363R/+116-123 (HQQNTQQA->TQADTSSP)=D92Y/E100W/H116T/Q118A/N119D/Q121S/Q122S/A123P/A217G/H363R, Q9S/E54C/D92Y/A101C/H143C/Q193R/I201C/A217G/N298S/H363R+116-123(HQQNTQQA->TQADTSSP)=Q9S/E54C/D92Y/A101C/H116T/Q118A/N119D/Q121S/Q122S/A123P/H143C/Q193R/I201C/A217G/N298S/H363R, Q9S/N78Q/A89A/D92Y/H115M/A132V/Q162RN179W/A217G/K234V/P348R/H363R, Q9S/N78Q/A89A/D92Y/H115M/A132V/Q162R/Y179W/A217G/K234V/S261F/P348R/H363R, Q9S/N78Q/A89A/D92Y/H115M/A132V/K139C/G151D/Q162RN179W/Q181L/I201C/A217G/K234V/P348R, D92Y/E100W/K139C/I201C/A217G/N247D/H363R, E54C/D92Y/A101C/M168V/A217G/H363R, Q9S/N78Q/A132V/K139C/Q162RN179W/I201C/A217G/K234L/P348R/H363R, D92Y/E100W/H1430/A144R/I201C/A217G/N247D/H363R, D92Y/E100W/H116S/K139C/I201C/A217G/N247D/H363R, D92Y/E100W/H128R/K139C/H143V/I201C/A217G/N247D/H363R, D92Y/E100W/K139C/I201C/$N_{206}$G/A217G/N247D/H363R, D92Y/E100W/K139C/I201C/A217G/N247D/H363R, D92Y/E100W/K139C/I201C/A217G/N247D/Q256D/H363R, D92Y/E100W/K139C/I201C/A217G/N247D/H363R, D92Y/E100W/K139C/I201C/A217G/N247D/N344K/H363R, D92Y/E100W/K139C/A144S/K176E/I201C/A217G/K234V/N247D/H363R, D92Y/E100W/K139C/I201C/A217G/K234V/N247D/H363R/E54C/H55E/A1010, D92Y/E100W/K139C/T152A/I201C/A217G/K234V/N247D/H363R, Y48H/D92Y/E100W/K139C/T152C/I201C/A217G/K234V/N247D/H363R, D92Y/E100W/K139C/I201C/A217G/K234V/N247D/S2840/H363R, D92Y/E100W/K139C/I201C/A217G/K234V/N247D/T287W/H363R, D92Y/E100W/K139C/I201C/A217G/K234V/N247D/R289M/H363R, Y48H/D92Y/E100W/K139C/I201C/A217G/K234V/N247D/R289W/H363R, N78Q/D92Y/E100W/K139C/I201C/A217G/K234V/N247D/Q256D/H363R, D92Y/E100W/K139C/I201C/A217G/K234V/N247D/Q256D/P348R/H363R, D92Y/E100W/K139C/Q162R/Q181L/I201C/A217G/K234V/N247D/Q256D/H363R, D92Y/E100W/A113G/K139C/I201C/A217G/K234V/N247D/H363R, D92Y/E100W/T120G or A*/K139C/I201C/A217G/K234V/N247D/H363R/L395L or V, D92Y/E100W/K139C/I201C/A217G/K234V/N247D/S284M/H363R, D92Y/E100W/K139C/I201C/A217G/K234V/N247D/H363R/A366S, D92Y/E100W/K139C/I201C/A217G/K234V/N247W/Q256D/H363R, D92Y/E100W/H128R/K139C/I201C/A217G/K234V/N247E/Q256D/H363R, D92Y/E100W/K139C/Q141S/I201C/A217G/K234V/N247D/H363R, D92Y/E100W/K139C/A144S/I201C/A217G/K234V/N247D/H363R, P75N/K76N/D77Q/N78T/D92Y/E100W/K139C/I201C/A217G/K234V/N247D/Q256D/H363R, D92Y/E100W/K139C/D173N/P175S/I201C/A217G/K234V/N247D/Q256D/H363R, D92Y/E100W/K139C/T152I/I201C/A217G/K234V/N247D/Q256D/1294T/H363R, D33 N/D92Y/E100W/K139C/I201C/A217G/K234V/N247 D/Q256D/H363R, Y48H/D92Y/E100W/K139C/T152C/I201C/A217G/K234V/N247D/Q256D/H363R, D92Y/E100W/K139C/T152A/I201C/A217G/K234V/N247D/Q256D/H363R, D92Y/T98S/E100W/K139C/T152A/I201C/A217G/K234V/N247D/Q256D/H363R, D92Y/T98S/E100W/K139C/T152A/L199S/I201C/A217G/K234V/N247W/Q256D/H363R, Y48H/D92Y/T98S/E100W/K139C/T152I/I201C/A217G/K234V/N247W/Q256D/H363R, E54C/D92Y/A101C/K139C/I201C/A217G/K234V/N247D/Q256D/H363R, Y48H/E54C/D92Y/A101C/K139C/I201C/A217G/K234V/N247D/R289W/H363R, D92Y/T98S/E100W/K139C/T152A/I201C/A217G/K234V/N247W/Q256D/R289W/H363R, Y48H/D92/E100W/K139C/T152C/I201C/A217G/K234V/N247W/Q256D/R289W/H363R, Y48H/D92Y/E100W/K139C/I201C/A217G/K234V/N247W/Q256D/H363R, Y48H/D92Y/E100W/K139C/T152A/I201C/A217G/K234V/N247D/R289W/H363R, Y48H/D92Y/E100W/K139C/T152A/I201C/A217G/K234V/N247W/Q256D/H363R, Y48H/E54C/D92Y/A101C/K139C/T152A/I201C/A217G/K234V/N247D/R289W/H363R, Y48H/E54C/D92Y/A101C/K139C/I201C/A217G/K234V/N247W/R289W/H363R, Y48H/E54C/D92Y/A101C/K139C/T152I201C/A217G/K234V/N247W/R289W/H363R, Y48H/E54C/D92Y/E100W/A101C/K139C/T152A/I201C/A217G/K234V/N247W/Q256D/H363R, Y48H/E54C/D92Y/A101C/K139C/T152A/I201C/$V_{208}$T/A217G/K234V/N247D/R289W/H363R, T35A/Y48H/E54C/P75N/K76N/D77Q/N78T/D92Y/A101C/K139C/T152A/I201C/A217G/K234V/N247D/R289W/H363R, Y48H/E54C/D92Y/A101C/K139C/T152A/I201C/K207Q/V208T/A217G/K234V/N247D/R289W/H363R, E540/D92Y/A101C/K139C/I201C/A217G/Q256D/H363R, E54C/P75N/K76N/D77Q/N78T/D92Y/A101C/K139C/I201C/A217G/H363R, E540/D92Y/A101C/K139C/I201C/V208T/A217G/H363R, E54C/P75N/K76N/D77Q/N78T/D92Y/A101C/K139C/I201C/V208T/A217G/H363R, Y48H/E54C/P75N/K76N/D77Q/N78T/D92Y/A101C/K139C/T152A/I201C/$V_{208}$T/A217G/K234V/N247D/R289W/H363R, E54C/P75N/K76N/D77Q/N78T/D92Y/A101C/K139C/I201C/V208T/A217G/K234V/N239S/N247D/Q256D/H363R.

The invention also relates to a method for producing a phytase variant, of a reference or parent phytase having at least 76% identity to SEQ ID NO:2 whereby said variant exhibits at least one substitution, insertion or deletion in one or more of the positions: 139, 1, 4, 5, 6, 7, 8, 9, 10, 12, 16, 18, 25, 26, 27, 28, 29, 30, 31, 32, 33, 35, 36, 37, 38, 39, 40, 41, 45, 48, 49, 54, 55, 59, 63, 64, 66, 68, 69, 70, 71, 72, 74, 75, 76, 77, 78, 79, 80, 81, 82, 83, 89, 91, 92, 93, 95, 96, 97, 98, 100, 101, 103, 108, 109, 110, 111, 112, 113, 115, 116, 117, 118, 119, 120, 121, 122, 123, 124, 125, 126, 128, 130, 131, 132, 133, 134, 136, 137, 138, 140, 143, 144, 145, 146, 147, 148, 149, 150, 151, 152, 153, 154, 155, 156, 158, 159, 160, 161, 162, 163, 168, 172, 173, 175, 176, 177, 178, 179, 180, 181, 182, 183, 184, 185, 186, 187, 189, 190, 192, 193, 194, 195, 196, 198, 199, 200, 201, 202, 203, 204, 205, 206, 207, 208, 209, 211, 215, 217, 219, 221, 224, 227, 228, 230, 233, 234, 235, 236, 238, 239, 240, 241, 242, 243, 244, 245, 246, 247, 248, 249, 251, 256, 258, 259, 260, 261, 266, 268, 270, 279, 284, 285, 286, 287, 288, 289, 290, 292, 293, 294, 295, 296, 297, 298, 299, 301, 303, 304, 308, 310, 312, 313, 314, 316, 318, 319, 320, 322, 324, 325, 326, 331, 335, 343, 344, 345, 346, 347, 348, 354, 355, 356, 358, 360, 362, 363, 364, 365, 366, 367, 368, 369, 370, 371, 372, 373, 374, 375, 376, 378, 382, 383, 384, 385, 386, 387, 388, 389, 390, 391, 394, 395, 396, 397, 400, 401, 403, 404, 406, 408, 409, 411, 412, and 413, wherein the positions correspond to the positions of the phytase with the amino acids 1-413 of SEQ ID NO:2, the method comprising, with the proviso that the variant is not the phytase with the amino acids 1-413 of SEQ ID NO:2, a) mutating the DNA or gene encoding the parent phytase in a manner whereby the DNA or gene encodes for said substitution, insertion and/or deletion, b) operably linking said DNA or gene to one or more control sequences that direct the production of the phytase in a suitable expression host to create a DNA construct or a recombinant expression vector, c) transferring said construct or vector to a suitable host, d) cultivating said host to produce the variant phytase, and e) recovering the phytase, Specifically the method provides for variants having improved properties in respect of thermal performance, including heat-stability, temperature stability, thermostability, steam stability, pelleting stability, and/or temperature profile, and/or an improved efficiency, including an improved pH profile, an improved specific activity, an altered glycosylation pattern, an improved performance in animal feed, and/or which incorporates a change of a potential protease cleavage site and/or glycation site.

Strategy for Preparing Variants

The structure of the *H. alvei* DSM 19197 phytase (amino acids 1 to 413 of SEQ ID NO:2) is disclosed in PCT/EP2008/053561.

The structure was subjected to molecular dynamics (MD) simulations and electrostatic calculations. Positions for putative disulfide bridges and prolines were also identified, as well as other positions of potential importance as regards the various desirable enzymatic properties. Finally, putative glycosylation sites (stretches of NXT or NXS) were identified.

All these suggestions were evaluated within the framework of the modelled structure and the simulation results, for the thermostability property with particular emphasis at the high temperature end.

The corresponding phytase variants were prepared by methods known in the art and tested as described in the experimental part.

Phytase Polypeptides, Percentage of Identity

In the present context a phytase is a polypeptide having phytase activity, i.e., an enzyme which catalyzes the hydrolysis of phytate (myo-inositol hexakisphosphate) to (1) myo-inositol and/or (2) mono-, di-, tri-, tetra- and/or penta-phosphates thereof and (3) inorganic phosphate.

In the present context the term a phytase substrate encompasses, i.a., phytic acid and any phytate (salt of phytic acid), as well as the phosphates listed under (2) above.

The ENZYME site at the internet (www.expasy.ch/enzyme/) is a repository of information relative to the nomenclature of enzymes. It is primarily based on the recommendations of the Nomenclature Committee of the International Union of Biochemistry and Molecular Biology (IUB-MB) and it describes each type of characterized enzyme for which an EC (Enzyme Commission) number has been provided (Bairoch A. The ENZYME database, 2000, *Nucleic Acids Res.* 28: 304-305). See also the handbook Enzyme Nomenclature from NC-IUBMB, 1992).

According to the ENZYME site, three different types of phytases are known: A so-called 3-phytase (alternative name 1-phytase; a myo-inositol hexaphosphate 3-phosphohydrolase, EC 3.1.3.8), a so-called 4-phytase (alternative name 6-phytase, name based on 1L-numbering system and not 1D-numbering, EC 3.1.3.26), and a so-called 5-phytase (EC 3.1.3.72). For the purposes of the present invention, all three types are included in the definition of phytase.

In a particular embodiment, the phytases of the invention belong to the family of histidine acid phosphatases (HAP), which includes the *Escherichia coli* pH 2.5 acid phosphatase (gene appA), as well as fungal phytases such as *Aspergillus awamorii* phytases A and B (EC: 3.1.3.8) (gene phyA and phyB). The histidine acid phosphatases share two regions of sequence similarity, each centered around a conserved histidine residue. These two histidines seem to be involved in the enzymes' catalytic mechanism. The first histidine is located in the N-terminal section and forms a phosphor-histidine intermediate while the second is located in the C-terminal section and possibly acts as proton donor.

In a further particular embodiment, the phytases of the invention have a conserved active site motif, viz. R—H-G-X—R—X—P, wherein X designates any amino acid (see amino acids 18 to 24 of SEQ ID NO:2). In a preferred embodiment, the conserved active site motif is R—H-G-V—R-A-P, i.e., amino acids 18-24 (by reference to SEQ ID NO:2) are RHGVRAP.

For the purposes of the present invention the phytase activity is determined in the unit of FYT, one FYT being the amount of enzyme that liberates 1 micro-mol inorganic orthophosphate per min. under the following conditions: pH 5.5; temperature 37° C.; substrate: sodium phytate ($C_6H_6O_{24}P_6Na_{12}$) in a concentration of 0.0050 mol/l. Suitable phytase assays are the FYT and FTU assays described in Example 1 of WO 00/20569. FTU is for determining phytase activity in feed and premix. Phytase activity may also be determined using the assays of Example 1 ("Determination of phosphatase activity" or "Determination of phytase activity").

In a particular embodiment the phytase of the invention is isolated. The term "isolated" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

The relatedness between two amino acid sequences is described by the parameter "identity". For purposes of the present invention, the alignment of two amino acid sequences is determined by using the Needle program from the EMBOSS package (http://emboss.org) version 2.8.0. The Needle program implements the global alignment algorithm described in Needleman and Wunsch, 1970, *J. Mol. Biol.* 48: 443-453. The substitution matrix used is BLOSUM62, gap opening penalty is 10, and gap extension penalty is 0.5.

The degree of identity between an amino acid sequence of the present invention ("invention sequence") and the amino acid sequence referred to in the claims (SEQ ID NO:2) is calculated as the number of exact matches in an alignment of the two sequences, divided by the length of the "invention sequence," or the length of the SEQ ID NO:2, whichever is the shortest. The result is expressed in percent identity.

An exact match occurs when the "invention sequence" and SEQ ID NO:2 have identical amino acid residues in the same positions of the overlap (in the alignment example below this is represented by "|"). The length of a sequence is the number of amino acid residues in the sequence (e.g., the length of amino acids 1-413 of SEQ ID NO:2 is 413).

For further detailed explanation reference is made to WO 2007/112739 at page 7, line 24 to page 8, line 5.

In particular embodiments of the phytase of the invention, the degree of identity to SEQ ID NO:2 is at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99%. In still further particular embodiments, the degree of identity is at least 98.0%, 98.2%, 98.4%, 98.6%, 98.8%, 99.0%, 99.1%, 99.2%, 99.3%, 99.4%, 99.5%, 99.6%, 99.7%, 99.8%, or at least 99.9%. In alternative embodiments, the degree of identity is at least 70%, 71%, 72%, or at least 73%.

In still further particular embodiments, the phytase of the invention has no more than 1, 2, 3, 4, 5, 6, 7, 8, 9, or no more than 10 modifications as compared to SEQ ID NO:2; no more than 11, 12, 13, 14, 15, 16, 17, 18, 19, or no more than 20 modifications as compared to SEQ ID NO:2; no more than 21, 22, 23, 24, 25, 26, 27, 28, 29, or no more than 30 modifications as compared to SEQ ID NO:2; no more than 31, 32, 33, 34, 35, 36, 37, 38, 39, or not more than 40 modifications as compared to SEQ ID NO:2; no more than 41, 42, 43, 44, 45, 46, 47, 48, 49, or no more than 50 modifications as compared to SEQ ID NO:2; no more than 51, 52, 53, 54, 55, 56, 57, 58, 59, or no more than 60 modifications as compared to SEQ ID NO:2; no more than 61, 62, 63, 64, 65, 66, 67, 68, 69, or no more than 70 modifications as compared to SEQ ID NO:2; no more than 71, 72, 73, 74, 75, 76, 77, 78, 79, or no more than 80 modifications as compared to SEQ ID NO:2; no more than 81, 82, 83, 84, 85, 86, 87, 88, 89, or no more than 90 modifications as compared to SEQ ID NO:2; no more than 91, 92, 93, 94, 95, 96, 97, 98, 99, or no more than 100 modifications as compared to SEQ ID NO:2; no more than 101, 102, 103, 104, 105, 106, 107, 108, 109, or no more than 110 modifications as compared to SEQ ID NO:2.

Position Numbering

The nomenclature used herein for defining amino acid positions is based on the amino acid sequence of the phytase derived from *Hafnia alvei* DSM 19197, the mature sequence of which is given in the sequence listing as SEQ ID NO:2 (amino acids 1-413 of SEQ ID NO:2). Accordingly, in the present context, the basis for numbering positions is SEQ ID NO:2 starting with S1 and ending with P413.

When used herein the term "mature" part (or sequence) refers to that part of the polypeptide which is secreted by a cell which contains, as part of its genetic equipment, a polynucleotide encoding the polypeptide. In other words, the mature polypeptide part refers to that part of the polypeptide which remains after the signal peptide part, as well as a propeptide part, if any, has been cleaved off. The signal peptide part can be predicted by programs known in the art (e.g., SignalP). SEQ ID NO:2 is the expected mature part. Generally, the first amino acid of the mature part of an enzyme can be determined by N-terminal sequencing of the purified enzyme. Any difference between the signal peptide part and the mature part must then be due to the presence of a propeptide.

Modifications, Such as Substitutions, Deletions, Insertions

A phytase variant can comprise various types of modifications relative to a template (i.e., a parent or reference phytase, or a comparative amino acid sequence such as SEQ ID NO:2): An amino acid can be substituted with another amino acid; an amino acid can be deleted; an amino acid can be inserted between two residues; as well as any combination of any number of such modifications. In the present context the term "insertion" is intended to cover also N- and/or C-terminal extensions.

The general nomenclature used herein for a single modification is the following: XDcY, where "X" and "Y" independently designate a one-letter amino acid code, or a "*" (deletion of an amino acid), "D" designates a number, and "c" designates an alphabetical counter (a, b, c, and so forth), which is only present in insertions. Reference is made to Table 1 below which describes purely hypothetical examples of applying this nomenclature to various types of modifications.

TABLE 1

Nomenclature examples

| Type | Description | Example |
|---|---|---|
| Substitution | X = Amino acid in template<br>D = Position in template<br>c empty<br>Y = Amino acid in variant | G80A<br><br>80<br>AALNNSIGVLGVAPSAELYAVKVLGASGSG<br>\|\|\|\|\|\|\|\|:\|\|\|\|\|\|\|\|\|\|\|\|\|\|\|\|\|\|\|\|\|\|<br>AALNNSIAVLGVAPSAELYAVKVLGASGSG |
| Insertion | X = "*"<br>D =<br>Position in template before the insertion<br>c = "a" for first insertion at this position, "b" for next, etc | *80aT *80bY *85aS<br><br>80    85<br>AALNNSIG..VLGVA.PSAELYAVKVLGASG<br>\|\|\|\|\|\|\|\|\| \|\|\|\|\| \|\|\|\|\|\|\|\|\|\|\|\|\|<br>AALNNSIGTYVLGVASPSAELYAVKVLGASG |
| Deletion | X = Amino acid in template<br>D = Position in template<br>c empty<br>Y = "*" | V81*<br><br>80<br>AALNNSIGVLGVAPSAELYAVKVLGASGSG<br>\|\|\|\|\|\|\|\| \|\|\|\|\|\|\|\|\|\|\|\|\|\|\|\|\|\|\|\|\|<br>AALNNSIG.LGVAPSAELYAVKVLGASGSG |
| N-terminal extension | Insertions at position "0". | *0aA *0bT *0cG<br><br>1<br>...AQSVPWGISRVQ<br>\|\|\|\|\|\|\|\|\|\|\|\|<br>ATGAQSVPWGISRVQ |
| C-terminal extension | Insertions after the N-terminal amino acid. | *275aS *275bT<br><br>270  275<br>ATSLGSTNLYGSGLVNAEAATR..<br>\|\|\|\|\|\|\|\|\|\|\|\|\|\|\|\|\|\|\|\|\|\|<br>ATSLGSTNLYGSGLVNAEAATRST |

As explained above, the position number ("D") is counted from the first amino acid residue of SEQ ID NO:2.

Several modifications in the same sequence are separated by "/" (slash), e.g., the designation "1*/2*/3*" means that the amino acids in position number 1, 2, and 3 are all deleted, and the designation "104A/105F" means that the amino acid in position number 104 is substituted by A, and the amino acid in position number 105 is substituted by F.

Alternative modifications are separated by "," (comma), e.g., the designation "119R,K" means that the amino acid in position 119 is substituted with R or K.

The commas used herein in various other enumerations of possibilities mean what they usually do grammatically, viz. often and/or. E.g., the first comma in the listing "53V,Q, 121D, and/or 167Q" denotes an alternative (V or Q), whereas the two next commas should be interpreted as and/or options: 53V or 53Q, and/or 121D, and/or 167Q.

In the present context, "at least one" (e.g., modification) means one or more, e.g., 1, 2, 3, 4, 5, 6, 7, 8, 9, or 10 modifications; or 12, 14, 15, 16, 18, 20, 22, 24, 25, 28, or 30 modifications; and so on, up to a maximum number of modifications of 125, 130, 140, 150, 160, 170, 180, 190, or of 200. The phytase variants of the invention, however, still have to be at least 76% identical to SEQ ID NO:2, this percentage being determined as described above.

A substitution or extension without any indication of what to substitute or extend with refers to the insertion of any natural, or non-natural, amino acid, except the one that occupies this position in the template.

Identifying Corresponding Position Numbers

As explained above, the mature phytase of *Hafnia alvei* DSM 19197 (SEQ ID NO:2) is used as the standard for position numbering and, thereby, also for the nomenclature.

For another phytase, in particular a phytase variant of the invention, the position corresponding to position D in SEQ ID NO:2 is found by aligning the two sequences as specified above in the section entitled "Phytase polypeptides, percentage of identity". From the alignment, the position in the sequence of the invention corresponding to position D of SEQ ID NO:2 can be clearly and unambiguously identified (the two positions on top of each other in the alignment).

Below some additional, purely hypothetical, examples are included which are derived from Table 1 above which in the third column includes a number of alignments of two sequences:

Consider the third cell in the first row of Table 1: The upper sequence is the template, the lower the variant. Position number 80 refers to amino acid residue G in the template. Amino acid A occupies the corresponding position in the variant. Accordingly, this substitution is designated G80A.

Consider now the third cell in the second row of Table 1: The upper sequence is again the template and the lower the variant. Position number 80 again refers to amino acid residue G in the template. The variant has two insertions, viz. TY, after G80 and before V81 in the template. Whereas the T and Y of course would have their own "real" position number in the variant amino acid sequence, for the present purposes we always refer to the template position numbers, and accordingly the T and the Y are said to be in position number 80a and 80b, respectively.

Finally, consider the third cell in the last row of Table 1: Position number 275 refers to the last amino acid of the template. A C-terminal extension of ST are said to be in position number 275a and 275b, respectively, although, again, of course they have their own "real" position number in the variant amino acid sequence.

Modified Properties, Reference or Parent Phytase

In a particular embodiment, the phytase of the invention has altered or modified, preferably improved, properties. The terms "altered", "modified" and "improved" imply a comparison with another phytase. Examples of such other, reference, parent or comparative, phytases are: SEQ ID NO:2, and/or other phytases having a sequence identity to SEQ ID NO:2 of more than 76%, preferably more than 80, 85, 90, 95, or 98%

Non-limiting examples of properties that are modified, preferably improved, are the following: Thermostability, steam stability, pelleting stability, pH profile, specific activity, performance in animal feed, protease-sensibility, and/or glycosylation pattern. The phytase of the invention may also have an altered, preferably improved, temperature profile, and/or it may incorporate changes of a potential protease cleavage sites to reduce the protease sensibility. Especially the thermal performance, including heat-stability, temperature stability, thermostability, steam stability, and/or pelleting stability is considered an important characteristic or proproperty, Thermal Performance Temperature-Stability Temperature stability may be determined as described in Example 3 by determining the residual activity after incubation for 30 minutes at temperatures from 70° C. to 80° C.

Thermostability

Thermostability may be determined as described in Example 4, i.e., using DSC measurements to determine the denaturation temperature, Td, of the purified phytase protein. The Td is indicative of the thermostability of the protein: The higher the Td, the higher the thermostability. Accordingly, in a preferred embodiment, the phytase of the invention has a Td which is higher than the Td of a reference phytase, wherein Td is determined on purified phytase samples (preferably with a purity of at least 90% or 95%, determined by SDS-PAGE).

Heat-Stability

Heat stability may be determined as described in Example 5 by determining the temperature/activity profile of the variant phytases.

Steam Stability

Steam stability may be determined as described in Example 7 by determining the residual activity of phytase molecules after steam treatment at 85° C. or 90° C. for a short time.

Pelleting Stability

Pelleting stability may be determined as described in Example 9 by using enzyme granulate pre-mixed with feed. This premix is mixed with feed. From the mixer the feed is conditioned with steam to 95° C. After conditioning the feed is pressed to pellets and the residual activity determined.

In preferred embodiments, the thermal properties such as heat-stability, temperature stability, thermostability, steam stability, and/or pelleting stability as provided by the residual activity, Td or other parameter of the phytase of the invention is higher than the corresponding value, such as the residual activity or Td, of the phytase of SEQ ID NO:2, more preferably at least 101% thereof, or at least 102%, 103%, 104%, 105%, 106%, 107%, 108%, 109%, or at least 110% thereof. Even more preferably, the value of the parameter, such as residual activity or Td, of the phytase of the invention is at least 120%, 130%, 140%, 150%, 160%, 170%, 180%, or at least 190% of the value for the phytase of SEQ ID NO:2.

In still further particular embodiments, the thermostable phytase of the invention has a melting temperature, Tm (or a denaturation temperature, Td), as determined using Differential Scanning calorimetry (DSC) as described in the Examples (i.e., in 20 mM sodium acetate, pH 4.0), of at least 50° C. In still further particular embodiments, the Tm is at least 51, 52, 53, 54, 55, 56, 57, 58, 59, 60, 61, 62, 62.5. 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or at least 100° C. DSC measurements may also be performed as described in the Examples.

The structure disclosed in PCT/EP2008/053561 was used to identify positions that are selected for modification. The structure was also compared to other known HAP phytase structures for the same purpose.

Using Molecular Dynamics simulations to analyse mobilities at high temperatures the following positions were identified for modification to provide improved thermal properties: 4, 5, 6, 7, 8, 9, 26, 27, 28, 29, 30, 32, 33, 37, 38, 39, 40, 41, 69, 70, 71, 72, 73, 74, 75, 76, 77, 78, 79, 80, 81, 82, 83, 91, 108, 109, 110, 111, 117, 118, 119, 120, 121, 122, 131, 132, 133, 134, 138, 139, 140, 144, 145, 147, 148, 149, 150, 151, 152, 153, 154, 155, 156, 158, 159, 160, 161, 163, 175, 178, 179, 180, 181, 182, 183, 184, 185, 186, 187, 189, 190, 193, 194, 196, 198, 200, 201, 202, 203, 204, 205, 206, 207, 233, 234, 235, 236, 238, 239, 240, 241, 242, 243, 244, 285, 286, 287, 288, 289, 290, 292, 293, 294, 295, 296, 297, 319, 320, 322, 324, 343, 344, 345, 346, 347, 364, 365, 366, 367, 369, 370, 371, 372, 373, 375, 382, 383, 384, 385, 386, 387, 388, 389, 390, 391, 396, 397, 400, 403, 404, 408, 409, 412, and 413.

It is specifically proposed that the modifications in some of these positions are selected from the following: 8L,C,M,Y, 9K,P,S, 26R,Q,H, 27A, 28A, 29P,R,K,A, 30P,L, 32Q,I,L, 33C,N, 37D,R,K, 38A, 41T,Q, 69E,L, 70E, 72A, 74S, 75A, 76R,V,N, 77K,G,W,Q, 78G,R,K,Q,S,T, 79L, 81E, 82S, 83G, 109D,G, 111R,K,S, 117A,Q, 118A,N,E,P,T, 119D,K,E, 120G,L,I,M, 121A,S,T,G,K, 122A,S,T,K, 131R,Q, 132T,V, 134V, 138N,V, 139C,R, 140P, 144R, 148R, 150C, 151D, 152A,G,T,I, 160G, 163P,K, 175N,S 178C,E 179C,L,W, 181L, 185R,K, 186S,T, 187E, 190N, 193R, 198E, 201C,G,V, 202A,K, 203Y, 206G,T,A, 207N,L,Q,R, 234L,R,C,V,E, 235P, 236C, 239R,K, 242S, 243P, 244P, 285D, 286T, 287P, 288P, 289W, 293R,K,N, 294L, 319L, 320N, 343C, 344K, 346S,T, 347R, 365K, 366T, 369S,D, 370C, 382S,T, 383N, 396D,E,K 403N, and 411S.

Based on comparisons to other known phytases the following positions were identitied to be able to provide improved thermal properties, such as thermostability: 12, 16, 48, 49, 54, 55, 77, 93, 100, 103, 128, 130, 136, 137, 173, 176, 195, 209, 211, 215, 219, 221, 227, 228, 248, 251, 258, 260, 261, 310, 313, 314, 316, 318, 335, 354, 356, 360, 362, 363, 374, 376, 378, and 411.

From the comparisons it is specifically indicated that the substitutions should be chosen among the following 12S, 16V, 48W, 49L, 54G, 55E, 77K, 93E, 100W, 103A, 128N, 130L, 136Q, 137L, 173N, 176Q, 195L, 209S, 211T, 215S, 219M, 221T, 227Q, 228Q, 248T, 251S, 258Y, 260L, 261Q, 310L, 313L, 314G, 316A, 318E, 335E, 354L, 356F, 360Q, 362M, 363R, 374P, 376E, 378K, and 411S In relation to variants produced from the phytase of SEQ ID NO:2 the modifications should be chosen from the following: K12S, L16V, Y48W, I49L, E54G, H55E, D77K, Q93E, L103A, H128N, V130L, S136Q, M137L, D173N, K176Q, M195L, A209S, E211T, G215S, T219M, A221T, E227Q, H228Q, S248T, K251S, D258Y, M260L, S261Q, I310L, I313L, S314G, M316A, G318E, A335E, M354L, Y356F, A360Q, L362M, H363R, A374P, S376E, R378K, and/or Q411S.

In particular embodiments, whereby disulfide bridges are created in the molecule, an improved thermostability is expected from the following variants of a phytase having at least 76% identity to amino acid residues 2-413 of SEQ ID NO:2: 8C/343C, 139C/201C, 179C/33C, 178C/33C, 172C/35C, 177C/36C, 176C/36C, 143C/201C, 54C/101C, 63C/368C, 66C/370C, 224C/236C, 150C/259C, 331C/326C, 358C/325C, 228C/363C, and 368C/374C.

Similarly an improved thermostability is also expected from substituting proline residues for the existing residues in selected positions. This is expected from the following phytase variants: 29P, 30P, 93P, 95P, 140P, 163P, 235P, 243P, 244P, 284P, 287P, 288P, 316P, and 360P. Specifically for modifications in SEQ ID NO:2 the following modifications should improve thermal stability Q29P, T30P, Q93P, K95P, S140P, A163P, V235P, E243P, Q244P, S284P, T287P, S288P, M316P, and A360P.

Also, the optimization of charged residues is able to improve thermal properties, such as thermostability. The optimization relates to the charge-charge interactions on the surface of the phytase molecule.

Three groups of substitutions are listed below for modifying parent or reference phytases having at least 76% identity to amino acid residues 1-413 of SEQ ID NO:2 with residues as indicated. The residues whose charge may be inverted, residues changed to a negative charge, and residues to be changed to a positive charge are:

Charge Inversion
D111R,K, K251D,E and D293R,K.
Change to Negative
Q69E, Q70E, T81E, Q93E, N119D, Q230E, Q245E, P348D,E, L395E, and S396D,E.
Change to Positive
Q9R, Q29R,K, H37R,K, L59R,K, N78R,K, H115R,K, I185R,K, N239R and H363R,K.

Temperature Profile/Temperature Stability

Whether or not a phytase of the invention has a modified temperature profile as compared to a reference phytase may be determined as described in Example 5. Accordingly, in a particular embodiment the phytase of the invention has a modified temperature profile as compared to a reference phytase, wherein the temperature profile is determined as phytase activity as a function of temperature on sodium phytate at pH 5.5 in the temperature range of 20-90° C. (in 10° C. steps). A preferred buffer is in 0.25 M Na-acetate buffer pH 5.5. The activity at each temperature is preferably indicated as relative activity (in %) normalized to the value at optimum temperature. The optimum temperature is that temperature within the tested temperatures (i.e., those with 5-10° C. jumps) where the activity is highest.

pH Profile

Whether or not a phytase of the invention has an altered pH profile as compared to a reference phytase may be determined as described in the Examples. Accordingly, in a particular embodiment the phytase of the invention has an altered pH profile as compared to a reference phytase, wherein the pH profile is determined as phytase activity as a function of pH on sodium phytate at 37° C. in the pH range of 2.0 to 7.5 (in 0.5 pH-unit steps). A preferred buffer is a cocktail of 50 mM glycine, 50 mM acetic acid and 50 mM Bis-Tris. The activity at each pH is preferably indicated as relative activity (in %) normalized to the value at optimum pH.

An example of an altered pH profile is where the pH curve (relative activity as a function of pH) is shifted towards higher, or lower, pH. Preferred substitutions which provide a shift of 0.5 pH units towards a higher pH as compared to the reference phytase of SEQ ID NO:2. However, for certain purposes it may be preferred to provide a shift of 0.5 pH units towards a lower pH as compared to the reference phytase of SEQ ID NO:2.

Another example of an altered pH profile is where the optimum pH is changed, in the upward or the downward direction.

In a particular embodiment, the phytase of the invention has an altered pH profile as compared to a reference phytase. More in particular, the pH profile is modified in the pH-range of 3.5-5.5. Still more in particular, the activity at pH 4.0, 4.5, 5.0, and/or 5.5 is at a level of at least 50%, 55%, 60%, 65%, 70%, 75%, 80%, 85%, 90%, or at least 95% of the activity at the pH-optimum.

Specific Activity

In a particular embodiment, the phytase of the invention has an improved specific activity relative to a reference phytase. More in particular, the specific activity of a phytase of the invention is at least 105%, relative to the specific activity of a reference phytase determined by the same procedure. In still further particular embodiments, the relative specific activity is at least 110, 115, 120, 125, 130, 140, 145, 150, 160, 170, 180, 190, 200, 220, 240, 260, 280, 300, 350 or even 400%, still relative to the specific activity of the reference phytase as determined by the same procedure.

In the alternative, the term high specific activity refers to a specific activity of at least 200 FYT/mg Enzyme Protein (EP). In particular embodiments, the specific activity is at least 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900 or 3000 FYT/mg EP.

Specific activity is measured on highly purified samples (an SDS poly acryl amide gel should show the presence of only one component). The enzyme protein concentration may be determined by amino acid analysis, and the phytase activity in the units of FYT, determined as described in Example 1. Specific activity is a characteristic of the specific phytase variant in question, and it is calculated as the phytase activity measured in FYT units per mg phytase variant enzyme protein. See the Examples for further details.

In particular embodiments, an modified specific activity is expected of the following variants of the phytase of SEQ ID NO:2, in which, in order of preference, the loop between replacing the loop between residues 115 and 127 (HQQNTQQADPL) which faces the active site with a loop selected from, e.g., HQEKMGTMDPT, HQQDIKQVDSL, HQPEIGKMDPV, TQADTSSPDPL, HQQDIKQADPL, TQTDTSSPDPL, NQADLKKTDPL.

Performance in Animal Feed

In a particular embodiment the phytase of the invention has an improved performance in animal feed as compared to a reference phytase. The performance in animal feed may be determined by the in vitro model indicated in the Examples. Accordingly, in a preferred embodiment the phytase of the invention has an improved performance in animal feed, wherein the performance is determined in an in vitro model, by preparing feed samples composed of 30% soybean meal and 70% maize meal with added $CaCl_2$ to a concentration of 5 g calcium per kg feed; pre-incubating them at 40° C. and pH 3.0 for 30 minutes followed by addition of pepsin (3000 U/g feed) and phytase; incubating the samples at 40° C. and pH 3.0 for 60 minutes followed by pH 4.0 for 30 minutes; stopping the reactions; extracting phytic acid and inositol-phosphates by addition of HCl to a final concentration of 0.5 M and incubation at 40° C. for 2 hours, followed by one freeze-thaw cycle and 1 hour incubation at 40° C.; separating phytic acid and inositol-phosphates by high performance ion chromatography; determining the amount of residual phytate phosphorus (IP6-P); calculating the difference in residual IP6-P between the phytase-treated and a non-phytase-treated blank sample (this difference is degraded IP6-P); and expressing the degraded IP6-P of the phytase of the invention relative to degraded IP6-P of the reference phytase.

The phytase of the invention and the reference phytase are of course dosed in the same amount, preferably based on phytase activity units (FYT). A preferred dosage is 125 FYT/kg feed. Another preferred dosage is 250 FYT/kg feed. The phytases may be dosed in the form of purified phytases, or in the form of fermentation supernatants. Purified phytases preferably have a purity of at least 95%, as determined by SDS-PAGE.

In preferred embodiments, the degraded IP6-P value of the purified phytase of the invention, relative to the degraded IP6-P value of the reference phytase, is at least 101%, or at least 102%, 103%, 104%, 105%, 110%, 115%, or at least 120%. In still further preferred embodiments, the degraded IP6-P value of the purified phytase of the invention, relative to the degraded IP6-P value of the reference phytase, is at least 125%, 130%, 140%, 150%, 160%, 170%, 180%, 190%, or at least 200%. Preferably, the degraded IP6-P value of the phytase of the invention, relative to the degraded IP6-P value of the SEQ ID NO:2 phytase, is at least 105%, 110%, 113%, 115%, 120%, 125%, or at least 130%.

The relative performance of a phytase of the invention may also be calculated as the percentage of the phosphorous released by the reference phytase.

In a still further particular embodiment, the relative performance of the phytase of the invention may be calculated as the percentage of the phosphorous released by the phytase of the invention, relative to the amount of phosphorous released by the reference phytase.

In still further particular embodiments, the relative performance of the phytase of the invention is at least 105%, preferably at least 110, 120, 130, 140, 150, 160, 170, 180, 190, or at least 200%.

Reduction in Glycation

Nonenzymatic glycation is a spontaneous posttranslational process where reducing sugars bind covalently to free amino groups in proteins primarily at Lysine (K) residues. In order to reduce glycation resulting in a reduction of activity of the phytase, the activity is improved by substituting certain amino acid residues, such as Lys. It is therefore proposed to make one or more of the following modifications in the phytase of SEQ ID NO:2: K12R,Q, K26R,Q, K45P, K76R,Q, K97R,Q, K131R,Q, K139R,Q, K148R,Q, K176R,Q, K187E, K207L, K234R,Q, K251R,Q, K268R,Q, K299R,Q, K347R, Q, S261A, T308A, T25A, T28A, T30L, T219L, T120L, $N_{202}A$, $N_2O_6A$, N270R,Q, N312A, N119D, Q256A, Q29A, Q121A, Q122A, Q117A, Q118A, Y48W, and Y179L. Specifically preferred modifications in respect of this improvement in efficiency are the modifications K26Q and K26R.

Reduced Protease-Sensibility

In a particular embodiment, the phytase of the invention has a reduced protease-sensibility. More in particular, it has a reduced sensibility towards the proteases pepsin and trypsin, meaning a reduced tendency to become cleaved by these protease.

The positions to be modified in this respect are indicated in Table 2 below

TABLE 2 positions for modifying protease sensibility

| Pepsin | Pepsin | Trypsin |
|--------|--------|---------|
| F8     | W42    | R22     |
| L46    | Y48    | K26     |
| L73    | L74    | K45     |
| L112   | F174   | K76     |
| L126   | W237   | K131    |

TABLE 2-continued positions for modifying protease sensibility

| Pepsin | Pepsin | Trypsin |
|--------|--------|---------|
| L157   | L323   | R160    |
| L188   | L379   | K176    |
| W321   |        | K187    |
| L368   |        | K234    |
| L370   |        |         |
| L395   |        |         |

To reduce the sensibility towards pepsin the amino acid residue should be modified to an amino-acid different from F, L, W or Y. In the case of Trypsin it should be modified to an amino acid residue different from R or K.

Glycosylation Pattern

Glycosylation is a phenomenon which is only observed when expressing proteins in eukaryotes such as fungi and transgenic plants, but not in prokaryotes such as bacteria. There are various types of glycosylation, but in the present context the most relevant is the N-glycosylation, i.e., the asparagine-linked glycosylation where sugars are attached to a protein, starting from an N-acetyglucosamine molecule attached to asparagines. N-glycosylation has been found to occur only to asparagines that in the sequence are part of the following tripeptides: N-X-T or N-X-S, where X designates any amino acid.

It has been observed that thermostability may be improved for phytases expressed in fungi by altering potential glycosylation sites.

The present invention accordingly also relates to phytase variants having an modified glycosylation pattern, preferably modified N-glycosylation sites. The modified glycosylation is expected to confer an improved thermostability upon the phytase variant, when expressed in a fungus.

Examples of phytases are bacterial phytases, e.g., Gram-negative phytases, such as *E. coli, Citrobacter* and *Hafnia* phytases and variants thereof, including the phytases of the present invention. Examples of fungal expression hosts are *Pichia, Saccharomyces*, and *Aspergillus* species.

In particular embodiments, an modified glycosylation pattern is expected of the following phytases of the invention:

Removal of a glycosylation site.

| Res. number | Res. type | Change to |
|-------------|-----------|-----------|
| 285         | Asn       | Asp       |

New glycosylation sites: NXX

| Res. number | Res. type | Change to |
|-------------|-----------|-----------|
| 121         | Gln       | Ser, Thr  |
| 186         | Gly       | Ser, Thr  |
| 249         | Leu       | Ser, Thr  |
| 331         | Pro       | Ser, Thr  |
| 346         | Gly       | Ser, Thr  |
| 355         | Val       | Ser, Thr  |
| 382         | Pro       | Ser, Thr  |

Creation of a new glycosylation sites of the type XXT

| Res. number | Res. type | Change to |
|-------------|-----------|-----------|
| 33          | Asp       | Asn       |
| 48          | Tyr       | Asn       |
| 93          | Gln       | Asn       |
| 96          | Arg       | Asn       |
| 118         | Gln       | Asn       |
| 320         | Thr       | Asn       |

Creation of a new glycosylation sites of the type XXS

| Res. number | Res. type | Change to |
|-------------|-----------|-----------|
| 138         | Asp       | Asn       |
| 162         | Gln       | Asn       |
| 175         | Pro       | Asn       |
| 190         | Asp       | Asn       |
| 246         | Trp       | Asn       |
| 293         | Asp       | Asn       |
| 383         | Gly       | Asn       |
| 394         | Pro       | Asn       |
| 401         | Leu       | Asn       |
| 403         | Ser       | Asn       |

Steam Stability

Thermostability is an important parameter, but associated with that also steam stability is important. In this respect reference is made to Example 8 below.

Low-Allergenic Variants

In a specific embodiment, the phytases of the present invention are (also) low-allergenic variants, designed to invoke a reduced immunological response when exposed to animals, including man. The term immunological response is to be understood as any reaction by the immune system of an animal exposed to the phytase variant. One type of immunological response is an allergic response leading to increased levels of IgE in the exposed animal. Low-allergenic variants may be prepared using techniques known in the art. For example the phytase variant may be conjugated with polymer moieties shielding portions or epitopes of the phytase variant involved in an immunological response. Conjugation with polymers may involve in vitro chemical coupling of polymer to the phytase variant, e.g., as described in WO 96/17929, WO 98/30682, WO 98/35026, and/or WO 99/00489. Conjugation may in addition or alternatively thereto involve in vivo coupling of polymers to the phytase variant. Such conjugation may be achieved by genetic engineering of the nucleotide sequence encoding the phytase variant, inserting consensus sequences encoding additional glycosylation sites in the phytase variant and expressing the phytase variant in a host capable of glycosylating the phytase variant, see e.g., WO 00/26354. Another way of providing low-allergenic variants is genetic engineering of the nucleotide sequence encoding the phytase variant so as to cause the phytase variants to self-oligomerize, effecting that phytase variant monomers may shield the epitopes of other phytase variant monomers and thereby lowering the antigenicity of the oligomers. Such products and their preparation is described e.g., in WO 96/16177. Epitopes involved in an immunological response may be identified by various methods such as the phage display method described in WO 00/26230 and WO 01/83559, or the random approach described in EP 561907. Once an epitope has been identified, its amino acid sequence may be altered to produce modified immunological properties of the phytase variant by known gene manipulation techniques such as site directed mutagenesis (see e.g., WO 00/26230, WO 00/26354 and/or WO 00/22103) and/or conjugation of a polymer may be done in sufficient proximity to the epitope for the polymer to shield the epitope.

Nucleic Acid Sequences and Constructs

The present invention also relates to nucleic acid sequences comprising a nucleic acid sequence which encodes a phytase variant of the invention.

The term "isolated nucleic acid sequence" refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The nucleic acid sequences of the invention can be prepared by introducing at least one mutation into a template phytase coding sequence or a subsequence thereof, wherein the mutant nucleic acid sequence encodes a variant phytase. The introduction of a mutation into the nucleic acid sequence to exchange one nucleotide for another nucleotide may be accomplished by any of the methods known in the art, e.g., by site-directed mutagenesis, by random mutagenesis, or by doped, spiked, or localized random mutagenesis.

Random mutagenesis is suitably performed either as localized or region-specific random mutagenesis in at least three parts of the gene translating to the amino acid sequence shown in question, or within the whole gene. When the mutagenesis is performed by the use of an oligonucleotide, the oligonucleotide may be doped or spiked with the three non-parent nucleotides during the synthesis of the oligonucleotide at the positions which are to be changed. The doping or spiking may be performed so that codons for unwanted amino acids are avoided. The doped or spiked oligonucleotide can be incorporated into the DNA encoding the phytase enzyme by any technique, using, e.g., PCR, LCR or any DNA polymerase and ligase as deemed appropriate.

Preferably, the doping is carried out using "constant random doping", in which the percentage of wild-type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints.

The random mutagenesis may be advantageously localized to a part of the parent phytase in question. This may, e.g., be advantageous when certain regions of the enzyme have been identified to be of particular importance for a given property of the enzyme.

Alternative methods for providing variants of the invention include gene shuffling e.g., as described in WO 95/22625 or in WO 96/00343, and the consensus derivation process as described in EP 897985.

Nucleic Acid Constructs

A nucleic acid construct comprises a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

The term "operably linked" denotes herein a configuration in which a control sequence is placed at an appropriate position relative to the coding sequence of the polynucleotide sequence such that the control sequence directs the expression of the coding sequence of a polypeptide.

When used herein the term "coding sequence" (CDS) means a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may a DNA, cDNA, or recombinant nucleotide sequence Expression Vector The term "expression" includes any step involved in the production of the polypeptide including, but not limited to, transcription, post-transcriptional modification, translation, post-translational modification, and secretion.

The term "expression vector" is defined herein as a linear or circular DNA molecule that comprises a polynucleotide encoding a polypeptide of the invention, and which is operably linked to additional nucleotides that provide for its expression.

A nucleic acid sequence encoding a phytase variant of the invention can be expressed using an expression vector which typically includes control sequences encoding a promoter, operator, ribosome binding site, translation initiation signal, and, optionally, a repressor gene or various activator genes.

The recombinant expression vector carrying the DNA sequence encoding a phytase variant of the invention may be any vector which may conveniently be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated.

The phytase variant may also be co-expressed together with at least one other enzyme of animal feed interest, such as a phytase, phosphatase, xylanase, galactanase, alpha-galactosidase, protease, phospholipase, amylase, and/or beta-glucanase. The enzymes may be co-expressed from different vectors, from one vector, or using a mixture of both techniques. When using different vectors, the vectors may have different selectable markers, and different origins of replication. When using only one vector, the genes can be expressed from one or more promoters. If cloned under the regulation of one promoter (di- or multi-cistronic), the order in which the genes are cloned may affect the expression levels of the proteins. The phytase variant may also be expressed as a fusion protein, i.e., that the gene encoding the phytase variant has been fused in frame to the gene encoding another protein. This protein may be another enzyme or a functional domain from another enzyme.

Host Cells

The term "host cell", as used herein, includes any cell type which is susceptible to transformation, transfection, transduction, and the like with a nucleic acid construct comprising a polynucleotide of the present invention.

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus*, *Bacillus licheniformis*, *Bacillus stearothermophilus*, or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

In an even more preferred aspect, the yeast host cell is a *Candida*, *Hansenula*, *Kluyveromyces*, *Pichia*, *Saccharomyces*, *Schizosaccharomyces*, or *Yarrowia* cell.

In a most preferred aspect, the yeast host cell is a *Pichia pastoris*, *Pichia methanolica*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium*, *Aspergillus*, *Aureobasidium*, *Bjerkandera*, *Ceriporiopsis*, *Coprinus*, *Coriolus*, *Cryptococcus*, *Filobasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

In a most preferred aspect, the filamentous fungal host cell is an *Aspergillus awamori*, *Aspergillus fumigatus*, *Aspergillus foetidus*, *Aspergillus japonicus*, *Aspergillus nidulans*, *Aspergillus niger* or *Aspergillus oryzae* cell. In another most preferred aspect, the filamentous fungal host cell is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* cell. In another most preferred aspect, the filamentous fungal host cell is a *Bjerkandera adusta*, *Ceriporiopsis aneirina*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Coprinus cinereus*, *Coriolus hirsutus*,

*Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* strain cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, Guide to Yeast Genetics and Molecular Biology, *Methods in Enzymology* 194: 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a phytase of the present invention comprising (a) cultivating a host cell under conditions conducive for production of the phytase; and (b) recovering the phytase.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

Transgenic Plants

The present invention also relates to a transgenic plant, plant part, or plant cell which has been transformed with a nucleotide sequence encoding a polypeptide having phytase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

In a particular embodiment, the polypeptide is targeted to the endosperm storage vacuoles in seeds. This can be obtained by synthesizing it as a precursor with a suitable signal peptide, see Horvath et al., 2000, *PNAS* 97(4): 1914-1919.

The transgenic plant can be dicotyledonous (a dicot) or monocotyledonous (a monocot) or engineered variants thereof. Examples of monocot plants are grasses, such as meadow grass (blue grass, *Poa*), forage grass such as *Festuca*, *Lolium*, temperate grass, such as *Agrostis*, and cereals, e.g., wheat, oats, rye, barley, rice, sorghum, triticale (stabilized hybrid of wheat (Triticum) and rye (Secale), and maize (corn). Examples of dicot plants are tobacco, legumes, such as sunflower (Helianthus), cotton (Gossypium), lupins, potato, sugar beet, pea, bean and soybean, and cruciferous plants (family Brassicaceae), such as cauliflower, rape seed, and the closely related model organism *Arabidopsis thaliana*. Low-phytate plants as described, e.g., in U.S. Pat. Nos. 5,689,054 and 6,111,168 are examples of engineered plants.

Examples of plant parts are stem, callus, leaves, root, fruits, seeds, and tubers, as well as the individual tissues comprising these parts, e.g., epidermis, mesophyll, parenchyma, vascular tissues, meristems. Also specific plant cell compartments, such as chloroplast, apoplast, mitochondria, vacuole, peroxisomes, and cytoplasm are considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seed coats.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences are determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific cell compartment, tissue or plant part such as seeds or leaves. Regulatory sequences are, for example, described by Tague et al., 1988, *Plant Physiology* 86: 506.

For constitutive expression, the following promoters may be used: The 35S-CaMV promoter (Franck et al., 1980, *Cell* 21: 285-294), the maize ubiquitin 1 (Christensen, Sharrock and Quail, 1992, Maize polyubiquitin genes: structure, thermal perturbation of expression and transcript splicing, and promoter activity following transfer to protoplasts by electroporation), or the rice actin 1 promoter (*Plant Mo. Biol.* 18: 675-689; Zhang, McElroy. and Wu, 1991, "Analysis of rice Act1 5' region activity in transgenic rice plants", *Plant Cell* 3: 1155-1165). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, Journal of Plant Physiology 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may be inducible by abiotic treatments such as temperature, drought or modifications in salinity or inducible by exogenously applied substances that activate the promoter, e.g., ethanol, oestrogens, plant hormones like ethylene, abscisic acid, gibberellic acid, and/or heavy metals.

A promoter enhancer element may also be used to achieve higher expression of the polypeptide in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

Still further, the codon usage may be optimized for the plant species in question to improve expression (see Horvath et al referred to above).

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38), and it can also be used for transforming monocots, although other transformation methods are more often used for these plants. Presently, the method of choice for generating transgenic monocots, supplementing the *Agrobacterium* approach, is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated therein the expression construct are selected and regenerated into whole plants according to methods well-known in the art. Often the transformation procedure is designed for the selective elimination of selection genes either during regeneration or in the following generations by using, e.g., co-transformation with two separate T-DNA constructs or site specific excision of the selection gene by a specific recombinase.

The present invention also relates to methods for producing a polypeptide of the present invention comprising (a) cultivating a transgenic plant or a plant cell comprising a nucleic acid sequence encoding a polypeptide having phytase activity of the present invention under conditions conducive for production of the polypeptide; and (b) recovering the polypeptide.

Transgenic Animals

The present invention also relates to a transgenic, non-human animal and products or elements thereof, examples of which are body fluids such as milk and blood, organs, flesh, and animal cells. Techniques for expressing proteins, e.g., in mammalian cells, are known in the art, see e.g., the handbook Protein Expression: A Practical Approach, Higgins and Hames (eds), Oxford University Press (1999), and the three other handbooks in this series relating to Gene Transcription, RNA processing, and Post-translational Processing. Generally speaking, to prepare a transgenic animal, selected cells of a selected animal are transformed with a nucleic acid sequence encoding a polypeptide having phytase activity of the present invention so as to express and produce the polypeptide. The polypeptide may be recovered from the animal, e.g., from the milk of female animals, or the polypeptide may be expressed to the benefit of the animal itself, e.g., to assist the animal's digestion. Examples of animals are mentioned below in the section headed Animal Feed.

To produce a transgenic animal with a view to recovering the polypeptide from the milk of the animal, a gene encoding the polypeptide may be inserted into the fertilized eggs of an animal in question, e.g., by use of a transgene expression vector which comprises a suitable milk protein promoter, and the gene encoding the polypeptide. The transgene expression vector is microinjected into fertilized eggs, and preferably permanently integrated into the chromosome. Once the egg begins to grow and divide, the potential embryo is implanted into a surrogate mother, and animals carrying the transgene are identified. The resulting animal can then be multiplied by conventional breeding. The polypeptide may be purified from the animal's milk, see e.g., Meade, H. M. et al (1999): Expression of recombinant proteins in the milk of transgenic animals, Gene expression systems: Using nature for the art of expression. J. M. Fernandez and J. P. Hoeffler (eds.), Academic Press.

In the alternative, in order to produce a transgenic non-human animal that carries in the genome of its somatic and/or germ cells a nucleic acid sequence including a heterologous transgene construct including a transgene encoding the polypeptide, the transgene may be operably linked to a first regulatory sequence for salivary gland specific expression of the polypeptide, as disclosed in WO 00/064247.

Compositions and Uses

In still further aspects, the present invention relates to compositions comprising a polypeptide of the present invention, as well as methods of using these.

The polypeptide compositions may be prepared in accordance with methods known in the art and may be in the form of a liquid or a dry composition. For instance, the polypeptide composition may be in the form of granulates or microgranulates. The polypeptide to be included in the composition may be stabilized in accordance with methods known in the art.

The phytase of the invention can be used for degradation, in any industrial context, of, for example, phytate, phytic acid, and/or the mono-, di-, tri-, tetra- and/or penta-phosphates of myo-inositol. It is well known that the phosphate moieties of these compounds chelates divalent and trivalent cations such as metal ions, i.a. the nutritionally essential ions of calcium, iron, zinc and magnesium as well as the trace minerals manganese, copper and molybdenum. Besides, the phytic acid also to a certain extent binds proteins by electrostatic interaction.

Accordingly, preferred uses of the polypeptides of the invention are in animal feed preparations (including human food) or in additives for such preparations.

In a particular embodiment, the polypeptide of the invention can be used for improving the nutritional value of an animal feed. Non-limiting examples of improving the nutritional value of animal feed (including human food), are: Improving feed digestibility; promoting growth of the animal; improving feed utilization; improving bio-availability of proteins; increasing the level of digestible phosphate; improving the release and/or degradation of phytate; improving bio-availability of trace minerals; improving bio-availability of macro minerals; eliminating or reducing the need for adding supplemental phosphate, trace minerals, and/or macro minerals; and/or improving egg shell quality. The nutritional value of the feed is therefore increased, and the growth rate and/or weight gain and/or feed conversion (i.e., the weight of ingested feed relative to weight gain) of the animal may be improved.

Furthermore, the polypeptide of the invention can be used for reducing phytate level of manure.

The phytase variants of the invention can also be used in in a method for producing a fermentation product, comprising (a) fermenting using a fermenting microorganism a carbohydrate containing material in the presence of a phytase of the invention and (b) producing the fermentation product or fermentation coproduct from the fermented carbohydrate containing material.

When used for this purpose the fermentation product is preferably ethanol, beer, wine, or distillers dried grains (DDG).

Animals, Animal Feed, and Animal Feed Additives

The term animal includes all animals, including human beings. Examples of animals are non-ruminants, and ruminants. Ruminant animals include, for example, animals such as sheep, goat, and cattle, e.g., cow such as beef cattle and dairy cows. In a particular embodiment, the animal is a non-ruminant animal. Non-ruminant animals include mono-gastric animals, e.g., pig or swine (including, but not limited to, piglets, growing pigs, and sows); poultry such as turkeys, ducks and chickens (including but not limited to broiler chicks, layers); fish (including but not limited to salmon, trout, tilapia, catfish and carp); and crustaceans (including but not limited to shrimp and prawn).

The term feed or feed composition means any compound, preparation, mixture, or composition suitable for, or intended for intake by an animal.

In the use according to the invention the polypeptide can be fed to the animal before, after, or simultaneously with the diet. The latter is preferred.

In a particular embodiment, the polypeptide, in the form in which it is added to the feed, or when being included in a feed additive, is substantially pure. In a particular embodiment it is well-defined. The term "well-defined" means that the phytase preparation is at least 50% pure as determined by Size-exclusion chromatography (see Example 12 of WO 01/58275). In other particular embodiments the phytase preparation is at least 60, 70, 80, 85, 88, 90, 92, 94, or at least 95% pure as determined by this method.

A substantially pure, and/or well-defined polypeptide preparation is advantageous. For instance, it is much easier to dose correctly to the feed a polypeptide that is essentially free from interfering or contaminating other polypeptides. The term dose correctly refers in particular to the objective of obtaining consistent and constant results, and the capability of optimising dosage based upon the desired effect.

For the use in animal feed, however, the phytase polypeptide of the invention need not be that pure; it may e.g., include other polypeptides, in which case it could be termed a phytase preparation.

The phytase preparation can be (a) added directly to the feed (or used directly in a treatment process of proteins), or (b) it can be used in the production of one or more intermediate compositions such as feed additives or premixes that is subsequently added to the feed (or used in a treatment process). The degree of purity described above refers to the purity of the original polypeptide preparation, whether used according to (a) or (b) above.

Polypeptide preparations with purities of this order of magnitude are in particular obtainable using recombinant methods of production, whereas they are not so easily obtained and also subject to a much higher batch-to-batch variation when the polypeptide is produced by traditional fermentation methods.

Such polypeptide preparation may of course be mixed with other polypeptides.

The polypeptide can be added to the feed in any form, be it as a relatively pure polypeptide, or in admixture with other components intended for addition to animal feed, i.e., in the form of animal feed additives, such as the so-called pre-mixes for animal feed.

In a further aspect the present invention relates to compositions for use in animal feed, such as animal feed, and animal feed additives, e.g., premixes.

Apart from the polypeptide of the invention, the animal feed additives of the invention contain at least one fat-soluble vitamin, and/or at least one water soluble vitamin, and/or at least one trace mineral. The feed additive may also contain at least one macro mineral.

Further, optional, feed-additive ingredients are colouring agents, e.g., carotenoids such as beta-carotene, astaxanthin, and lutein; aroma compounds; stabilisers; antimicrobial peptides; polyunsaturated fatty acids; reactive oxygen generating species; and/or at least one other polypeptide selected from amongst phytase (EC 3.1.3.8 or 3.1.3.26); phosphatase (EC 3.1.3.1; EC 3.1.3.2; EC 3.1.3.39); xylanase (EC 3.2.1.8); galactanase (EC 3.2.1.89); alpha-galactosidase (EC 3.2.1.22); protease (EC 3.4.-.-), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); and/or beta-glucanase (EC 3.2.1.4 or EC 3.2.1.6).

In a particular embodiment these other polypeptides are well-defined (as defined above for phytase preparations).

The phytase of the invention may also be combined with other phytases, for example ascomycete phytases such as

*Aspergillus phytases*, for example derived from *Aspergillus ficuum, Aspergillus niger*, or *Aspergillus awamori*; or basidiomycete phytases, for example derived from *Peniophora lycii, Agrocybe pediades, Trametes pubescens*, or *Paxillus involutus*; or derivatives, fragments or variants thereof which have phytase activity.

Thus, in preferred embodiments of the use in animal feed of the invention, and in preferred embodiments of the animal feed additive and the animal feed of the invention, the phytase of the invention is combined with such phytases.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus* and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and polypeptides such as an oxidase, an oxygenase or a syntethase.

Usally fat- and water-soluble vitamins, as well as trace minerals form part of a so-called premix intended for addition to the feed, whereas macro minerals are usually separately added to the feed. Either of these composition types, when enriched with a polypeptide of the invention, is an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The following are non-exclusive lists of examples of these components:

Examples of fat-soluble vitamins are vitamin A, vitamin D3, vitamin E, and vitamin K, e.g., vitamin K3.

Examples of water-soluble vitamins are vitamin B12, biotin and choline, vitamin B1, vitamin B2, vitamin B6, niacin, folic acid and panthothenate, e.g., Ca-D-panthothenate.

Examples of trace minerals are manganese, zinc, iron, copper, iodine, selenium, and cobalt.

Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

The present invention also relates to animal feed compositions. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

WO 01/58275 corresponds to U.S. Ser. No. 09/779,334 which is hereby incorporated by reference.

An animal feed composition according to the invention has a crude protein content of 50-800 g/kg, and furthermore comprises at least one polypeptide as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e., Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen bv, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one protein. The protein may be an animal protein, such as meat and bone meal, and/or fish meal; or it may be a vegetable protein. The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g., soybean, lupine, pea, or bean.

In another particular embodiment, the vegetable protein source is material from one or more plants of the family Chenopodiaceae, e.g., beet, sugar beet, spinach or quinoa.

Other examples of vegetable protein sources are rapeseed, sunflower seed, cotton seed, and cabbage.

Soybean is a preferred vegetable protein source.

Other examples of vegetable protein sources are cereals such as barley, wheat, rye, oat, maize (corn), rice, triticale, and sorghum.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

Animal diets can, e.g., be manufactured as mash feed (non pelleted) or pelleted feed or extruded feed. Typically, the milled feed-stuffs are mixed and sufficient amounts of essential vitamins and minerals are added according to the specifications for the species in question. Polypeptides can be added as solid or liquid polypeptide formulations. For example, a solid polypeptide formulation is typically added before or during the mixing step; and a liquid polypeptide preparation is typically added after the pelleting step. The polypeptide may also be incorporated in a feed additive or premix.

The final polypeptide concentration in the diet is within the range of 0.01-200 mg polypeptide protein per kg diet, for example in the range of 5-30 mg polypeptide protein per kg animal diet.

The phytase of the invention should of course be applied in an effective amount, i.e., in an amount adequate for improving solubilisation and/or improving nutritional value of feed. It is at present contemplated that the polypeptide is administered in one or more of the following amounts (dosage ranges): 0.01-200; 0.01-100; 0.5-100; 1-50; 5-100; 10-100; 0.05-50; or 0.10-10—all these ranges being in mg phytase polypeptide protein per kg feed (ppm).

For determining mg phytase polypeptide protein per kg feed, the phytase is purified from the feed composition, and the specific activity of the purified phytase is determined using a relevant assay. The phytase activity of the feed composition as such is also determined using the same assay, and on the basis of these two determinations, the dosage in mg phytase protein per kg feed is calculated.

The same principles apply for determining mg phytase polypeptide protein in feed additives. Of course, if a sample is available of the phytase used for preparing the feed additive or the feed, the specific activity is determined from this sample (no need to purify the phytase from the feed composition or the additive).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

EXAMPLES

Chemicals used were commercial products of at least reagent grade.

Example 1

Preparation of Variants, and Determination of Activity

Preparation of Phytase Variants
Expression of Phytase Variants in *Asperqillus oryzae*

The constructs comprising the *Hafnia* phytase variant genes in the examples were used to construct expression vectors for *Aspergillus*. The *Aspergillus* expression vectors consist of an expression cassette based on the *Aspergillus niger* neutral amylase II promoter fused to the *Aspergillus nidulans* triose phosphate isomerase non translated leader sequence (Pna2/tpi) and the *Aspergillus niger* amyloglycosidase terminator (Tamg). Also present on the plasmid was the *Aspergillus* selective marker amdS from *Aspergillus nidulans* enabling growth on acetamide as sole nitrogen source. The expression plasmids for phytase variants were transformed into *Aspergillus* as described in Lassen et al., 2001, Applied and Environmental Microbiology 67: 4701-4707. For each of the constructs 10-20 strains were isolated, purified and cultivated in shake flasks.

Purification of *Hafnia alvei* Phytase Variants

The fermentation supernatant with the phytase variant was filtered through a Fast PES Bottle top filter with a 0.22 µm cut-off. The resulting solution was diluted with water to the double volume and pH was adjusted to 4.5 with acetic acid. Occasionally, the solution became a little cloudy and this removed by filtration through a Fast PES Bottle top filter with a 0.22 µm cut-off.

After pretreatment the phytase variant was purified by chromatography on S Sepharose, approximately 30 ml in a XK26 column, using as buffer A 50 mM sodium acetate pH 4.5, and as buffer B 50 mM sodium acetate+1 M NaCl pH 4.5. The fractions from the column were analyzed for activity using the phosphatase assay (see below) and fractions with activity were pooled.

Finally, the solution containing the purified phytase variant was concentrated using an Amicon ultra-15 filtering device with a 30 kDa cut-off membrane.

The molecular weight, as estimated from SDS-PAGE, was approximately 45 kDa and the purity was >95%.

Determination of Phosphatase Activity 75 microliters phytase-containing enzyme solution is dispensed in a microtiter plate well, e.g. NUNC 269620 and 75 microliter substrate is added (for preparing the substrate, two 5 mg p-nitrophenyl phosphate tablets (Sigma, Cat. No. N-9389) are dissolved in 10 ml 0.1 M Na-acetate buffer, pH 5.5). The plate is sealed and incubated 15 min., shaken with 750 rpm at 37° C. After the incubation time 75 microliter stop reagent is added (the stop reagent is 0.1 M di-sodiumtetraborate in water) and the absorbance at 405 nm is measured in a microtiter plate spectrophotometer. One phosphatase unit is defined as the enzyme activity that releases 1 micromol phosphate/min under the given reaction conditions (buffer blind subtracted). The absorbance of 1 micromol p-nitrophenol is determined to be 56 AU (AU=absorbancy units) under assay conditions.

Determination of Phytase Activity 75 microliters phytase-containing enzyme solution, appropriately diluted in 0.25 M sodium acetate, 0.005% (w/v) Tween-20. pH 5.5, is dispensed in a microtiter plate well, e.g. NUNC 269620, and 75 microliter substrate is added (prepared by dissolving 100 mg sodium phytate from rice (Aldrich Cat. No. 274321) in 10 ml 0.25 M sodium acetate buffer, pH 5.5). The plate is sealed and incubated 15 min. shaken with 750 rpm at 37° C. After incubation, 75 microliters stop reagent is added (the stop reagent being prepared by mixing 10 ml molybdate solution (10% (w/v) ammonium heptamolybdate in 0.25% (w/v) ammonia solution), 10 ml ammonium vanadate (0.24% commercial product from Bie&Berntsen, Cat. No. LAB17650), and 20 ml 21.7% (w/v) nitric acid), and the absorbance at 405 nm is measured in a microtiter plate spectrophotometer. The phytase activity is expressed in the unit of FYT, one FYT being the amount of enzyme that liberates 1 micromole inorganic ortho-phosphate per minute under the conditions above. An absolute value for the measured phytase activity may be obtained by reference to a standard curve prepared from appropriate dilutions of inorganic phosphate, or by reference to a standard curve made from dilutions of a phytase enzyme preparation with known activity (such standard enzyme preparation with a known activity is available on request from Novozymes NS, Krogshoejvej 36, DK-2880 Bagsvaerd).

Example 2

Specific Activity

The specific activity of a phytase variant is determined on highly purified samples dialysed against 250 mM sodium acetate, pH 5.5. The purity is checked beforehand on an SDS poly acryl amide gel showing the presence of only one component.

The protein concentration is determined by amino acid analysis as follows: An aliquot of the sample is hydrolyzed in 6 N HCl, 0.1% phenol for 16 h at 110° C. in an evacuated glass tube. The resulting amino acids are quantified using an Applied Biosystems 420A amino acid analysis system operated according to the manufacturer's instructions. From the amounts of the amino acids the total mass—and thus also the concentration—of protein in the hydrolyzed aliquot can be calculated.

The phytase activity is determined in the units of FYT as described in Example 1 ("Determination of phytase activity"), and the specific activity is calculated as the phytase activity measured in FYT units per mg phytase variant enzyme protein.

Example 3

Temperature Stability

Strains and Plasmids
E. coli DH12S (available from Gibco BRL) was used for yeast plasmid rescue.
pJHP000 is a S. cerevisiae and E. coli shuttle vector under the control of TPI promoter, constructed from pJC039 described in WO 01/92502, in which the Hafnia alvei phytase gene has been inserted.
Saccharomyces cerevisiae YNG318: MATa Dpep4[cir+] ura3-52, leu2-D2, his 4-539 was used for the phytase variants expression. It is described in J. Biol. Chem. 272(15): 9720-9727, 1997.
Media and Substrates
10× Basal solution: Yeast nitrogen base w/o amino acids (DIFCO) 66.8 g/l, succinate 100 g/l, NaOH 60 g/l.
SC-glucose: 20% glucose (i.e., a final concentration of 2%=2 g/100 ml)) 100 ml/l, 5% threonine 4 ml/l, 1% tryptophan 10 ml/l, 20% casamino acids 25 ml/l, 10× basal solution 100 ml/l. The solution is sterilized using a filter of a pore size of 0.20 micrometer. Agar and H2O (approx. 761 ml) is autoclaved together, and the separately sterilized SC-glucose solution added to the agar solution.

YPD: Bacto peptone 20 g/l, yeast extract 10 g/l, 20% glucose 100 ml/l.
PEG/LiAc solution: 40% PEG4000 50 ml, 5 M Lithium Acetate 1 ml
DNA Manipulations
Unless otherwise stated, DNA manipulations and transformations were performed using standard methods of molecular biology as described in Sambrook et al., 1989, Molecular cloning: A laboratory manual, Cold Spring Harbor lab. Cold Spring Harbor, N.Y.; Ausubel, F. M. et al. (eds.) "Current protocols in Molecular Biology", John Wiley and Sons, 1995; Harwood, C. R. and Cutting, S. M. (eds.).
Yeast Transformation
Yeast transformation was carried out by lithium acetate method. Mix 0.5 microL of vector (digested by restriction endonucleases) and 1 microL of PCR fragments. Thaw YNG318 competent cells on ice. Mix 100 microL of the cells, the DNA mixture and 10 microL of carrier DNA (Clontech) in 12 ml polypropylene tubes (Falcon 2059). Add 0.6 ml PEG/LiAc solution and mix gently. Incubate for 30 min at 30° C., and 200 rpm. Incubate for 30 min at 42° C. (heat shock). Transfer to an Eppendorf tube and centrifuge for 5 sec. Remove the supernatant and resolve in 3 ml of YPD. Incubate the cell suspension for 45 min at 200 rpm at 30° C. Pour the suspension to SC-glucose plates and incubate 30° C. for 3 days to make colonies. Yeast total DNA was extracted by the Robzyk and Kassir's method described in Nucleic Acids Research 20(14): 3790 (1992).
DNA Sequencing
E. coli transformation for DNA sequencing was carried out by electroporation (BIO-RAD Gene Pulser). DNA Plasmids were prepared by alkaline method (Molecular Cloning, Cold Spring Harbor) or with the Qiagen® Plasmid Kit. DNA fragments were recovered from agarose gel by the Qiagen gel extraction Kit. PCR was performed using a PTC-200 DNA Engine. The ABI PRISM™ 310 Genetic Analyzer was used for determination of all DNA sequences.
Construction of Phytase Expression Vector The Hafnia phytase gene was amplified with the primer pairs (HafPhyF and HafPHyR). The resulting PCR fragments were introduced into S. cerevisiae YNG318 together with the pJC039 vector digested with restriction enzymes to remove the mature part of Humicola insolens cutinase gene.

```
HafPhyF (34mer)
CTCCTGAACTTGTTGCCCGGTCGGATACAGCCCC

HafPhyR (39mer)
ATTACATGATGCGGCCCTCTAGATTAGGGGAGCTGACATG
```

Plasmid, which is termed as pJHP000 from the yeast transformants on SC-glucose plates was recovered and the internal sequence was determined to confirm the phytase gene.
Construction of Yeast Library and Site-Directed Variants
Library in yeast and site-directed variants were constructed by SOE PCR method (Splicing by Overlap Extension, see "PCR: A practical approach", p. 207-209, Oxford University press, eds. McPherson, Quirke, Taylor), followed by yeast in vivo recombination.
General Primers for Amplification and Sequencing
The below primers are used to make DNA fragments containing any mutated fragments by the SOE method together with degenerated primers (AM34+Reverse primer and AM35+forward primer) or just to amplify a whole asparaginase gene (AM34+AM35).

| | | | | |
|---|---|---|---|---|
| AM34 | TAGGAGTTTAGTGAACTTGC | | | |
| AM35 | TTCGAGCGTCCCAAAACC | | | |

| PCR reaction system: | | | Conditions: | |
|---|---|---|---|---|
| 48.5 micro L | H₂O | 1 | 94° C. | 2 min |
| 2 beads | puRe Taq Ready-To-Go PCR | 2 | 94° C. | 30 sec |
| Beads (Amersham bioscineces) | | 3 | 55° C. | 30 sec |
| 0.5 micro L X 2100 pmole/micro L Primers | | 4 | 72° C. | 90 sec |
| 0.5 micro L | Template DNA | 2-4 | 25 cycles | |
| | | 5 | 72° C. | 10 min |

DNA fragments were recovered from agarose gel by the Qiagen gel extraction Kit. The resulting purified fragments were mixed with the vector digest. The mixed solution was introduced into *Saccharomyces cerevisiae* to construct libraries or site-directed variants by in vivo recombination.

Library Screening (the Primary Membrane Assay)

Yeast libraries were cultivated on SC-glucose plate with a cellulose acetate membrane (upper) and Biodyne C (from Pall gelman) membrane (lower) at 30° C. at least for 3 days. The BiodyneC membranes were transferred to pre-incubated plates containing 20 mM acetate buffer, pH 4.0 and incubated for 1-2 hours at a certain temperature (50° C. in the case of WT as a backbone).

Then, the membranes were removed and soaked in the fresh substrate solution (10 ml 20 mM acetate buffer, pH 4.0; 0.01 g, alpha-naphtyl phosphate (sigma); 0.02 g, Fast Garnet GBC (sigma)). Yeast clones corresponding to the positions of red color developed on the Biodyne C membranes were isolated from cellulose acetate membranes.

Library Screening (the Secondary Relative Activity Selection)

Yeast clones on cellulose acetate membranes were inoculated to a well of a 96-well micro titre plate and cultivated at 28° C. for 3 days. Phytase activity was measured at both 37° C. and the higher temperature (60, 62, 64, 66° C. etc.) to determine the relative activity at a certain temperature. Then the clones with higher relative activity were selected and the sequence was confirmed.

| | |
|---|---|
| Standard, Level control and samples are pipetted into a MTP or 8 strip tube. | 10 microliters |
| Pre-heated (50° C.) substrate is added. | 200 microliters |
| The 8-stripe tube or MTP is placed in an MTP incubator at 37, 60 and 64° C. (or above). | 30 min. |
| Take out 35 μl, add it into 100 microliters of stop-complex reagent and mixed 5-20 s. | 35 + 100 microliters |
| The sample waits before measurement. | 5-30 min |
| OD is measured at | 750 nm |

Substrate, Sodium Phytate Solution 2.0 mM (Every Time)
Example of preparation of 100 ml:
Sodium phytate 0.1847 g
0.1 M Acetate buffer, pH4.0 up to 100 ml
Complexing Reagent
Example of preparation of 200 ml:
FeSO₄.7H₂O 14.64 g
Ammonium heptamolybdate solution up to 200 ml
Stop-Complex Reagent
Example of preparation of 600 ml stop-complex reagent
0.5 M H2SO4 200 ml
Complexing Reagent 400 ml
Ammonium heptamolybdate solution
Example of preparation of 1000 ml:
(NH₄)₆Mo7O₂₄.4H₂O 10.0 g
Sulfuric acid 32 ml
Demineralized water up to 1000 ml The results are provided below. The column indicating the relative activity provides first the relative activity of the variant and thereafter the relative activity of the reference phytase used in the determination. The reference is either the wild type or variants nos. 62, 69, 84, 104, 105, 113 and/or 138. The variants were typically used as reference when the residual activity of the wild type was very low.

Results

| Variant no. | Modifications (substitutions, insertions or deletions) | Relative activity (control/reference variant) |
|---|---|---|
| 005 | A132V/Q162R | 11% at 72° C. (WT2%) |
| 007 | Y179W | 12% at 72° C. (WT2%) |
| 008 | A132V/Q181L | 15% at 72° C. (WT2%) |
| 011 | A132V/E211R | 10% at 72° C. (WT2%) |
| 012 | A132V/D83G | 11% at 72° C. (WT3%) |
| 013 | A132V/A217G | 50% at 72° C. (WT2%) |
| 014 | A132V/A217S | 47% at 72° C. (WT2%) |
| 015 | A221G | 11% at 72° C. (WT2%) |
| 016 | R32I | 46% at 72° C. (WT26%) |
| 017 | R32L | 38% at 72° C. (WT26%) |
| 020 | D77G | 46% at 72° C. (WT26%) |
| 021 | D77W | 40% at 72° C. (WT26%) |
| 023 | T95A | 44% at 72° C. (WT26%) |
| 024 | E100W/H363R | 42% at 72° C. (WT26%) |
| 025 | D111S | 69% at 72° C. (WT26%) |
| 027 | D138V/Y48H | 48% at 72° C. (WT39%) |
| 028-1 | K234C | 50% at 72° C. (WT39%) |
| 028-2 | K234V | 50% at 72° C. (WT39%) |
| 029 | K251S | 46% at 72° C. (WT39%) |
| 030 | H363V | 40% at 72° C. (WT39%) |
| 031 | H363R | 53% at 72° C. (WT39%) |
| 046-1 | A132V/A217G | 42% at 70° C. (WT13%) |
| 046-2 | A132V/Q162R/Q181L/A217G | 42% at 70° C. (WT13%) |

-continued

| Variant no. | Modifications (substitutions, insertions or deletions) | Relative activity (control/reference variant) |
|---|---|---|
| 047 | D293R | 30% at 70° C. (WT13%) |
| 048 | Q93E | 22% at 70° C. (WT13%) |
| 050-1 | P348R/H363R | 30% at 70° C. (WT13%) |
| 050-2 | P348S | 30% at 70° C. (WT13%) |
| 051 | Q69L | 20% at 70° C. (WT13%) |
| 052 | Q245E | 19% at 70° C. (WT13%) |
| 053 | Q9S/D92Y | 42% at 70° C. (WT13%) |
| 054-2 | D92Y/H115L | 28% at 70° C. (WT13%) |
| 054-re1,2 | D92Y/H115M | 32% at 70° C. (WT17%) |
| 057 | N78Q | 56% at 70° C. (WT28%) |
| 058 | K76V | 57% at 70° C. (WT28%) |
| 061-1 | G325K | 47% at 70° C. (WT28%) |
| 062 | E100W/A217G/H363R(reference) | 63% at 72° C. (WT17%) |
| 063 | A217G/K251S | 40% at 72° C. (WT17%) |
| 064 | E100W/A217G/K251S | 38% at 72° C. (WT17%) |
| 065 | E100W/K251S | 26% at 72° C. (WT17%) |
| 066 | A217G | 29% at 72° C. (WT10%) |
| 067 | E100W/I555V/A217G | 45% at 72° C. (WT9%) |
| 068 | Q9S/E100W/R160G/A217G/H363R | 45% at 72° C. (WT9%) |
| 069 | D92Y/E100W/A217G/H363R(reference) | 79% at 72° C. (WT9%) |
| 070 | E100W/H115M/A217G/H363R | 41% at 72° C. (WT9%) |
| 071 | E100W/A217G/P348R/H363R | 63% at 72° C. (WT9%) |
| 072 | Q9S/A89A/D92Y/H115M/A217G/H363R | 67% at 72° C. (WT9%) |
| 073 | A132T | 21% at 72° C. (WT16%) |

Reference = variant no. 62

| Variant no. | Modifications | Relative activity |
|---|---|---|
| 075 | N78Q/E100W/A217G/H363R | 47% at 72° C. (62 40%) |
| 076 | K76V/N78Q/E100W/A217G/H363R | 47% at 72° C. (62 40%) |
| 077 | D83G/E100W/A217G/H363R | 39% at 72° C. (62 40%) |
| 078 | E100W/Y179W/A217G/H363R | 48% at 72° C. (62 40%) |
| 079 | E100W/A217G/K234V/K251E/I286T/H363R | 60% at 72° C. (62 40%) |
| 081 | E100W/A217G/K234V/P348R/H363R | 50% at 72° C. (62 35%) |
| 082 | Q9S/R18K/A89A/D92Y/H115M/A217G/K234V/H363R | 61% at 72° C. (62 35%) |
| 082v2-1 | Q9S/D92Y/H115M/A217G/K234V/H363R | 61% at 72° C. (62 35%) |
| 083 | Q9S/N78Q/D92Y/L112S/H115M/K234V/P348R/H363R | 39% at 72° C. (62 35%) |
| 084 | Q9S/N78Q/A89A/D92Y/H115M/A132V/Q162R/Q181L/A217G/K234V/P348R(reference) | 64% at 72° C. (62 35%) |

Reference = WT and/or variant no. 69

| Variant no. | Modifications | Relative activity |
|---|---|---|
| 085 | Q9S/E54C/D92Y/A101C/H143C/Q193R/I201C/A217G/H363R | 82% at 72° C. (69 74% WT 14%) |
| 086 | E54C/N78S/D92Y/A101C/H143C/L199C/A217G/H363R | 74% at 72° C. (wt 49% 69 80%) |
| 088 | E54C/A101C/M168V/A217G/H363R | 33% at 72° C. (62 36% 69 73%) |
| 089-1 | P82S/D92Y/E100W/H143C/I201C/A217G/H363R | 65% at 72° C. (62 36% 69 73%) |
| 089-2 | P82S/D92Y/E100W/H143C/I201C/A217G/H363R | 65% at 72° C. (62 36% 69 73%) |
| 090 | Q9S/N78Q/D92Y/L112S/H115M/A217G/K234V/P348R/H363R | 65% at 72° C. (62 36% 69 73%) |
| 091 | D92Y/A217G/K234V/H363R | 81% at 72° C. (62 36% 69 73%) |
| 092-1 | Y64S/D92Y/E100W/Y179W/A217G/H363R | 80% at 72° C. (69 74% WT 14%) |
| 092-2 | D92Y/A217G/H363R | 80% at 72° C. (69 74% WT 14%) |
| 094 | Q9S/N78Q/A89A/D92Y/H115M/A132V/H143C/Q162R/Q181L/I201C/A217G/K234V/P348R | 54% at 74° C. (wt 9% 69 45%) |
| 095 | Q9S/N78Q/A89A/D92Y/H115M/A132V/K139C/Q162R/Q181L/I201C/A217G/K234V/P348R | 75% at 74° C. (wt 9% 69 45%) |
| 097 | Q9S/N78Q/A89A/D92Y/H115M/A132V/Q162R/Y179W/Q181L/A217G/K234V/P348R | 76% at 74° C. (wt 9% 69 45%) |
| 100 | D33C/D92Y/E100W/Y179C/A217G/H363R/ | 49% at 72° C. (69 79%) |
| 103-1 | Q9S/N78Q/A89A/D92Y/H115M/A132V/Q162R/Y179W/A217G/K234V/P348R/H363R | 103% at 72° C. (69 88%) |
| 103-3 | Q9S/N78Q/A89A/D92Y/H115M/A132V/Q162R/Y179W/A217G/K234V/S261F/P348R/H363R | 99% at 72° C. (69 88%) |

-continued

| Variant no. | Modifications (substitutions, insertions or deletions) | Relative activity (control/reference variant) |
|---|---|---|
| | | Reference = variant 69 and/or variant 84 |
| 101 | D92Y/E100W/A217G/H363R/+ 116-123(HQQNTQQA->TQADTSSP) | 21% at 76° C. (69 39%, 84 55%) |
| 102 | Q9S/E54C/D92Y/A101C/H143C/Q193R/I201C/A217G/N298S/H363R +116-123(HQQNTQQA->TQADTSSP) | 29% at 76° C. (69 39%, 84 55%) |
| 104 | Q9S/N78Q/A89A/D92Y/H115M/A132V/K139C/G151D/Q162R/Y179W/Q181L/I201C/A217G/K234V/P348R (reference) | 55% at 74° C. (69 57% 84 65%) |
| 105 | D92Y/E100W/K139C/I201C/A217G/N247D/H363R (reference) | 77% at 74° C. (69 57% 84 65%) |
| | | Reference = variant 104 and variant 69 |
| 106 | E54C/D92Y/A101C/M168V/A217G/H363R | 22% at 74° C. (104 70% 69 54%) |
| 107 | Q9S/N78Q/A132V/K139C/Q162R/Y179W/I201C/A217G/K234L/P348R/H363R | 34% at 74° C. (104 70% 69 54%) |
| | | Reference = variant 105 |
| 108 | D92Y/E100W/H143C/A144R/I201C/A217G/N247D/H363R | 37% at 80° C. (105 36%) |
| 109 | D92Y/E100W/H116S/K139C/I201C/A217G/N247D/H363R | 43% at 78° C. (105 36%) |
| 110 | D92Y/E100W/H128R/K139C/H143V/I201C/A217G/N247D/H363R | 44% at 78° C. (105 36%) |
| 111 | D92Y/E100W/K139C/I201C/N206G/A217G/N247D/H363R | 45% at 78° C. (105 36%) |
| 112 | D92Y/E100W/K139C/I201C/A217G/N247D/H363R | 51% at 78° C. (105 36%) |
| 113 | D92Y/E100W/K139C/I201C/A217G/N247D/Q256D/H363R | 98% at 78° C. (105 36%) |
| 114 | D92Y/E100W/K139C/I201C/A217G/N247D/H363R | 49% at 78° C. (105 36%) |
| 115 | D92Y/E100W/K139C/I201C/A217G/N247D/N344K/H363R | 32% at 78° C. (105 36%) |
| 117 | D92Y/E100W/K139C/A144S/K176E/I201C/A217G/K234V/N247D/H363R | 38% at 80° C. (105 34%) |
| 118 | D92Y/E100W/K139C/I201C/A217G/K234V/N247D/H363R/E54C/H55E/A101C | 32% at 80° C. (105 34%) |
| 123 | D92Y/E100W/K139C/T152A/I201C/A217G/K234V/N247D/H363R | 27% at 80° C. (105 15%) |
| 124 | Y48H/D92Y/E100W/K139C/T152I/I201C/A217G/K234V/N247D/H363R | 17% at 80° C. (105 15%) |
| 125 | D92Y/E100W/K139C/I201C/A217G/K234V/N247D/S284C/H363R | 20% at 80° C. (105 15%) |
| 126 | D92Y/E100W/K139C/I201C/A217G/K234V/N247D/T287W/H363R | 20% at 80° C. (105 15%) |
| 127 | D92Y/E100W/K139C/I201C/A217G/K234V/N247D/R289M/H363R | 18% at 80° C. (105 15%) |
| 128 | Y48H/D92Y/E100W/K139C/I201C/A217G/K234V/N247D/R289W/H363R | 17% at 80° C. (105 15%) |
| 129 | N78Q/D92Y/E100W/K139C/I201C/A217G/K234V/N247D/Q256D/H363R | 103% at 80° C. (105 34%) |
| 130 | D92Y/E100W/K139C/I201C/A217G/K234V/N247D/Q256D/P348R/H363R | 99% at 80° C. (105 34%) |
| 131 | D92Y/E100W/K139C/Q162R/Q181L/I201C/A217G/K234V/N247D/Q256D/H363R | 76% at 80° C. (105 34%) |
| 132 | D92Y/E100W/A113G/K139C/I201C/A217G/K234V/N247D/H363R | 34% at 80° C. (105 34%) |
| 133 | D92Y/E100W/T120GorA*/K139C/I201C/A217G/K234V/N247D/H363R/L395LorV | 41% at 80° C. (105 34%) |
| 135 | D92Y/E100W/K139C/I201C/A217G/K234V/N247D/S284M/H363R | 24% at 80° C. (105 34%) |
| 137 | D92Y/E100W/K139C/I201C/A217G/K234V/N247D/H363R/A366S | 31% at 80° C. (105 34%) |
| 138 | D92Y/E100W/K139C/I201C/A217G/K234V/N247W/Q256D/H363R | 89% at 80° C. (105 14%) |
| 140 | D92Y/E100W/H128R/K139C/I201C/A217G/K234V/N247E/Q256D/H363R | 49% at 80° C. (105 14%) |
| 141 | D92Y/E100W/K139C/Q141S/I201C/A217G/K234V/N247D/H363R | 24% at 80° C. (105 14%) |
| 142 | D92Y/E100W/K139C/A144S/I201C/A217G/K234V/N247D/H363R | 18% at 80° C. (105 14%) |
| 144 | P75N/K76N/D77Q/N78T/D92Y/E100W/K139C/I201C/A217G/K234V/N247D/Q256D/H363R | 71% at 80° C. (105 30%) |

| Variant no. | Modifications (substitutions, insertions or deletions) | Relative activity (control/reference variant) |
|---|---|---|
| 145 | D92Y/E100W/K139C/D173N/P175S/I201C/A217G/K234V/N247D/Q256D/H363R | 27% at 80° C. (105 30%) |
| 147 | D92Y/E100W/K139C/T152A/I201C/A217G/K234V/N247D/Q256D/I294T/H363R | 90% at 80° C. (105 26%) |
| | | Reference = variant 113 |
| 143 | D33N/D92Y/E100W/K139C/I201C/A217G/K234V/N247D/Q256D/H363R | 29% at 80° C. (113 62%) |
| 148 | Y48H/D92Y/E100W/K139C/T152I/I201C/A217G/K234V/N247D/Q256D/H363R | 74% at 80° C. (113 80%) |
| 150 | D92Y/E100W/K139C/T152A/I201C/A217G/K234V/N247D/Q256D/H363R | 67% at 82° C. (113 33%) |
| 151 | D92Y/T98S/E100W/K139C/T152A/I201C/A217G/K234V/N247D/Q256D/H363R | 29% at 82° C. (113 33%) |
| 152 | D92Y/T98S/E100W/K139C/T152A/L199S/I201C/A217G/K234V/N247W/Q256D/H363R | 38% at 80° C. (113 80%) |
| 153 | Y48H/D92Y/T98S/E100W/K139C/T152A/I201C/A217G/K234V/N247W/Q256D/H363R | 38% at 80° C. (113 54%) |
| 154 | E54C/D92Y/A101C/K139C/I201C/A217G/K234V/N247D/Q256D/H363R | 91% at 80° C. (113 73%) |
| 155 | Y48H/E54C/D92Y/A101C/K139C/I201C/A217G/K234V/N247D/R289W/H363R | 88% at 80° C. (113 80%) |
| 156 | D92Y/T98S/E100W/K139C/T152A/I201C/A217G/K234V/N247W/Q256D/R289W/H363R | 41% at 82° C. (113 33%) |
| 157 | Y48H/D92/E100W/K139C/T152I/I201C/A217G/K234V/N247W/Q256D/R289W/H363R | 79% at 80° C. (113 80%) |
| 158 | Y48H/D92Y/E100W/K139C/I201C/A217G/K234V/N247W/Q256D/H363R | 95% at 80° C. (113 80%) |
| 159 | Y48H/D92Y/E100W/K139C/T152A/I201C/A217G/K234V/N247D/R289W/H363R | 20% at 80° C. (113 57%) |
| 160 | Y48H/D92Y/E100W/K139C/T152A/I201C/A217G/K234V/N247W/Q256D/H363R | 92% at 80° C. (113 80%) |
| 161 | Y48H/E54C/D92Y/A101C/K139C/T152A/I201C/A217G/K234V/N247D/R289W/H363R | 55% at 80° C. (113 80%) |
| 162 | Y48H/E54C/D92Y/A101C/K139C/I201C/A217G/K234V/N247W/R289W/H363R | 56% at 80° C. (113 80%) |
| 163 | Y48H/E54C/D92Y/A101C/K139C/T152A/I201C/A217G/K234V/N247W/R289W/H363R | 66% at 80° C. (113 80%) |
| | | Reference = variant 138 |
| 164 | Y48H/E54C/D92Y/E100W/A101C/K139C/T152A/I201C/A217G/K234V/N247W/Q256D/H363R | 94% at 80° C. (138 78%) |
| 165 | Y48H/E54C/D92Y/A101C/K139C/T152A/I201C/V208T/A217G/K234V/N247D/R289W/H363R | 65% at 80° C. (138 78%) |
| 166 | T35A/Y48H/E54C/P75N/K76N/D77Q/N78T/D92Y/A101C/K139C/T152A/I201C/A217G/K234V/N247D/R289W/H363R | 15% at 80° C. (138 78%) |
| 167 | Y48H/E54C/D92Y/A101C/K139C/T152A/I201C/K207Q/V208T/A217G/K234V/N247D/R289W/H363R | 61% at 80° C. (138 78%) |
| | | Reference = wt |
| 168 | E54C/D92Y/A101C/K139C/I201C/A217G/Q256D/H363R | 69% at 80° C. (w 7%) |
| 169 | E54C/P75N/K76N/D77Q/N78T/D92Y/A101C/K139C/I201C/A217G/H363R | 33% at 80° C. (w 7%) |
| 170 | E54C/D92Y/A101C/K139C/I201C/V208T/A217G/H363R | 32% at 80° C. (w 7%) |
| 171 | E54C/P75N/K76N/D77Q/N78T/D92Y/A101C/K139C/I201C/V208T/A217G/H363R | 36% at 80° C. (w 7%) |
| 172 | Y48H/E54C/P75N/K76N/D77Q/N78T/D92Y/A101C/K139C/T152A/I201C/V208T/A217G/K234V/N247D/R289W/H363R | 48% at 80° C. (w 7%) |
| 173 | E54C/P75N/K76N/D77Q/N78T/D92Y/A101C/K139C/I201C/V208T/A217G/K234V/N239S/N247D/Q256D/H363R | 50% at 80° C. (w 7%) |

Example 4

Thermostability

An aliquot of the protein sample of *Hafnia alvei* phytase (purified as described in Example 1) was either desalted and buffer-changed into 20 mM Na-acetate, pH 4.0 using a pre-packed PD-10 column or dialysed against 2×500 ml 20 mM Na-acetate, pH 4.0 at 4° C. in a 2-3 h step followed by an overnight step. The sample was 0.45 micro-m filtered and diluted with buffer to approx. 2 A280 units. The dialysis buffer was used as reference in Differential Scanning calorimetry (DSC). The samples were degassed using vacuum suction and stirring for approx. 10 minutes.

A DSC scan was performed on a MicroCal VP-DSC at a constant scan rate of 1.5° C./min from 20-90° C. Data-handling was performed using the MicroCal Origin software (version 4.10), and the denaturation temperature, Td (also called the melting temperature, Tm) is defined as the temperature at the apex of the peak in the thermogram.

The results of DSC for *Hafnia alvei* phytase variants are summarized in the Table 3 below.

TABLE 3

Comparative Thermostability of Hafnia alvei Phytases

| Variant | Td 1st Scan (° C.) |
|---|---|
| A150C/L259C | 62.4 |
| Q162N/R96N | 63.8 |
| L16V/I310L/I313L/M319L/M354L | 64.3 |
| V87I/L103A/L112I/A113T/I114V | 67.4 |
| E66C/L370C | 67.2 |
| H363R | 68.3 |
| Q162N/G186S | 67.5 |
| E54C/A101C | 68.0 |
| V130L/M137L/V146I/I201V/M260L/I266V | 67.8 |
| Wt | 69 |
| K45P | 70.9 |
| K139C/I201C | 70.8 |
| E54C/A101C/K139C/I201C | 72.6 |
| D92Y/E100W/A217G/H363R | 75.1 |
| Q9S/N78Q/A89A/D92Y/H115M/A132/K139C/Q162/Q181L/I201C/A217G/K234V/P348R | 75.5 |
| Y48H/D92Y/E100W/K139C/T152I/I201C/A217G/K234V/N247D/H363R | 77.7 |
| D92Y/E100W/K139C/I201C/A217G/N247D/H363R | 78.0 |
| Y48H/D92Y/E100W/K139C/I201C/A217G/K234V/N247D/R289W/H363R | 78.9 |
| E54C/D92Y/A101C/K139C/I201C/A217G/H363R | 79.8 |
| E54C/D92Y/A101C/K139C/I201C/A217G/K234V/N247D/Q256D/H363R | 80.0 |
| Y48H/E54C/D92Y/A101C/K139C/T152A/I201C/A217G/K234V/N247D/R289W/H363R | 80.2 |
| Y48H/D92Y/E100W/K139C/I201C/A217G/K234V/N247D/Q256D/H363R | 81.7 |
| Y48H/D92Y/T98S/E100W/K139C/T152A/I201C/A217G/K234V/N247W/Q256/H363R | 82.7 |
| Y48H/D92Y/E100W/K139C/T152A/I201C/A217G/K234V/N247W/Q256D/H363R | 83.1 |
| D92Y/E100W/K139C/I201C/A217G/K234V/N247W/Q256D/H363R | 84.2 |
| S1QGPS/K26H/E54C/A101C/K139C/Q162N/G186S/I201C/K207Q/G346S | 71.9 |

Example 5

Temperature Profile

The temperature profile (phytase activity as a function of temperature) was determined for the *Hafnia alvei* phytase and variants in the temperature range of 20-90° C. essentially as described above ("Determination of phytase activity"). However, the enzymatic reactions (100 microliter phytase-containing enzyme solution+100 microliters substrate) were performed in PCR tubes instead of microtiter plates. After a 15 minute reaction period at desired temperature the tubes were cooled to 20° C. for 20 seconds and 150 microliters of each reaction mixture was transferred to a microtiter plate. 75 microliter stop reagent was added and the absorbance at 405 nm was measured in a microtiter plate spectrophotometer. The results are summarized in Table 4 below. The numbers given for each temperature are relative activity (in %) normalized to the value at optimum.

TABLE 4

Relative temperature profiles

| Phytase variant | Temperature (° C.) | | | | | | | | | | |
|---|---|---|---|---|---|---|---|---|---|---|---|
| | 20 | 30 | 40 | 50 | 60 | 65 | 70 | 75 | 80 | 85 | 90 |
| *wt | 18 | 29 | 50 | 75 | 100 | 94 | 93 | 24 | 12 | 7 | 5 |
| *K131Q | 21 | 34 | 53 | 77 | 94 | 99 | 100 | 26 | 16 | 10 | 6 |
| Q162N/D138N | 17 | 28 | 44 | 66 | 88 | 100 | 95 | 26 | 14 | 9 | 7 |
| I294L | 18 | 30 | 46 | 64 | 90 | 100 | 90 | 26 | 14 | 11 | 11 |
| G72A | 17 | 29 | 45 | 67 | 83 | 100 | 78 | 26 | 13 | 11 | 8 |
| H143C/I201C | 10 | 22 | 37 | 62 | 85 | 100 | 91 | 26 | 5 | 5 | 4 |
| Q162R | 18 | 30 | 49 | 73 | 91 | 100 | 95 | 26 | 15 | 11 | 9 |
| I49L | 17 | 29 | 45 | 65 | 90 | 100 | 94 | 26 | 13 | 9 | 11 |
| *E66C/L370C | 15 | 27 | 43 | 66 | 100 | 88 | 99 | 27 | 12 | 6 | 5 |
| T369S | 18 | 28 | 47 | 64 | 92 | 100 | 95 | 27 | 15 | 11 | 9 |
| I201V | 16 | 27 | 41 | 59 | 78 | 100 | 82 | 27 | 13 | 11 | 8 |
| K148R | 19 | 35 | 51 | 71 | 98 | 97 | 100 | 27 | 11 | 7 | 6 |
| A163K | 14 | 27 | 38 | 63 | 79 | 100 | 93 | 27 | 12 | 9 | 6 |
| S1QS | 15 | 26 | 40 | 62 | 87 | 93 | 100 | 27 | 9 | 4 | 2 |
| F8M | 15 | 27 | 38 | 67 | 96 | 100 | 91 | 27 | 10 | 5 | 5 |
| F8Y | 16 | 27 | 44 | 69 | 96 | 100 | 93 | 27 | 10 | 6 | 6 |
| T242S | 18 | 30 | 48 | 66 | 91 | 100 | 93 | 27 | 12 | 11 | 10 |
| K176R | 17 | 33 | 43 | 66 | 100 | 96 | 96 | 28 | 8 | 5 | 3 |
| S403N | 14 | 32 | 42 | 67 | 84 | 100 | 96 | 28 | 14 | 10 | 8 |
| S1P | 17 | 27 | 44 | 60 | 87 | 100 | 92 | 28 | 13 | 11 | 8 |
| E41Q | 16 | 28 | 44 | 63 | 87 | 100 | 99 | 28 | 13 | 9 | 9 |
| *K131L | 18 | 30 | 50 | 72 | 85 | 95 | 100 | 29 | 15 | 8 | 4 |
| *K207R | 18 | 30 | 48 | 70 | 88 | 93 | 100 | 29 | 15 | 8 | 5 |
| *K207Q | 23 | 37 | 58 | 81 | 92 | 97 | 100 | 29 | 18 | 10 | 7 |
| G346S | 16 | 28 | 47 | 65 | 95 | 100 | 92 | 29 | 10 | 6 | 4 |
| T308A | 9 | 17 | 33 | 56 | 80 | 99 | 100 | 29 | 12 | 9 | 6 |

TABLE 4-continued

| | Relative temperature profiles |
| | Temperature (° C.) |

| Phytase variant | 20 | 30 | 40 | 50 | 60 | 65 | 70 | 75 | 80 | 85 | 90 |
|---|---|---|---|---|---|---|---|---|---|---|---|
| S396K | 19 | 31 | 44 | 69 | 86 | 100 | 87 | 30 | 14 | 12 | 10 |
| L401N | 14 | 33 | 43 | 68 | 86 | 100 | 87 | 30 | 13 | 10 | 7 |
| I201G | 16 | 28 | 43 | 62 | 81 | 100 | 87 | 30 | 14 | 11 | 8 |
| P348R | 18 | 30 | 43 | 62 | 81 | 100 | 91 | 31 | 14 | 11 | 8 |
| E100W | 18 | 29 | 40 | 61 | 79 | 100 | 85 | 31 | 13 | 10 | 7 |
| K187E | 16 | 28 | 39 | 66 | 90 | 100 | 92 | 31 | 10 | −6 | 4 |
| N239R | 19 | 30 | 48 | 66 | 89 | 100 | 96 | 32 | 12 | 11 | 10 |
| A304V | 15 | 24 | 42 | 58 | 86 | 100 | 98 | 32 | 14 | 11 | 8 |
| S396D | 16 | 28 | 41 | 60 | 81 | 100 | 87 | 32 | 13 | 10 | 8 |
| T152G | 16 | 28 | 42 | 66 | 85 | 100 | 95 | 32 | 14 | 10 | 9 |
| K12R | 18 | 29 | 42 | 64 | 82 | 100 | 98 | 33 | 14 | 12 | 8 |
| I303L | 17 | 27 | 40 | 62 | 86 | 100 | 88 | 33 | 13 | 11 | 10 |
| Q162N | 16 | 27 | 42 | 62 | 89 | 90 | 100 | 34 | 10 | 7 | 3 |
| S192A | 17 | 26 | 43 | 59 | 88 | 100 | 94 | 35 | 13 | 9 | 9 |
| T369D | 18 | 29 | 43 | 66 | 86 | 100 | 90 | 35 | 14 | 12 | 11 |
| V130L/M137L/V146I/I201V/M260L/I266V | 13 | 25 | 43 | 67 | 89 | 98 | 100 | 35 | 14 | 10 | 6 |
| Q109G | 17 | 33 | 44 | 68 | 94 | 100 | 94 | 36 | 11 | 6 | |
| N239K | 19 | 31 | 47 | 70 | 92 | 100 | 94 | 38 | 14 | 12 | 6 |
| K234V | 17 | 29 | 42 | 63 | 79 | 100 | 94 | 39 | 15 | 11 | 8 |
| K234E | 17 | 27 | 43 | 61 | 86 | 100 | 92 | 40 | 15 | 11 | 7 |
| H363R | 18 | 28 | 42 | 66 | 90 | 100 | 90 | 41 | 11 | 6 | 5 |
| S261A | 13 | 24 | 39 | 62 | 83 | 98 | 100 | 41 | 14 | 10 | 7 |
| A217G | 14 | 32 | 41 | 65 | 84 | 100 | 90 | 43 | 15 | 11 | 7 |
| E54C/A101C/K207Q | 21 | 33 | 48 | 68 | 89 | 100 | 95 | 55 | 13 | 10 | 6 |
| K45P | 19 | 29 | 43 | 68 | 86 | 100 | 93 | 59 | 18 | 11 | 10 |
| E54C/A101C | 16 | 27 | 42 | 64 | 85 | 100 | 88 | 64 | 9 | 7 | 4 |
| D33C/E54C/A101C/Y179C | 16 | 31 | 45 | 67 | 94 | 100 | 82 | 74 | 9 | 6 | 3 |
| E54C/A101C/K139C/I201C/K207Q | 18 | 30 | 41 | 62 | 85 | 80 | 100 | 84 | 36 | 9 | 10 |
| D92Y/E100W/A217G/H363R | 6 | 13 | 27 | 50 | 89 | 85 | 100 | 84 | 32 | 10 | 5 |
| E54C/A101C/K139C/I201C | 15 | 28 | 40 | 59 | 86 | 78 | 100 | 86 | 47 | 8 | 9 |
| K139C/I201C | 18 | 25 | 37 | 56 | 91 | 91 | 100 | 87 | 15 | 7 | 4 |
| S1QGPS/K26H/E54C/A101C/K139C/Q162N/G186S/I201C/K207Q/G346S | 26 | 37 | 49 | 67 | 80 | 100 | 92 | 90 | 18 | 13 | 10 |
| Y48H/E54C/D92Y/A101C/K139C/T152A/I201C/K207Q/V208T/A217G/K234V/N247D/R289W/H363R | 10 | 20 | 39 | 63 | 85 | 81 | 100 | 92 | 58 | 11 | 6 |
| T35A/Y48H/E54C/P75N/K76N/D77Q/N78T/D92Y/A101C/K139C/T152A/I201C/A217G/K234V/N247D/R289W/H363R | 5 | 9 | 28 | 50 | 77 | 80 | 100 | 93 | 13 | 5 | 1 |
| Y48H/E54C/D92Y/A101C/K139C/T152A/I201C/V208T/A217G/K234V/N247D/R289W/H363R | 5 | 13 | 26 | 53 | 76 | 83 | 100 | 95 | 75 | 11 | 4 |
| E54C/D92Y/A101C/K139C/I201C/A217G/H363R | 10 | 15 | 28 | 52 | 81 | 93 | 100 | 96 | 83 | 10 | 1 |
| E54C/D92Y/A101C/K139C/I201C/A217G/K234V/N247D/Q256D/H363R | 9 | 16 | 33 | 58 | 81 | 84 | 100 | 96 | 79 | 18 | 6 |
| D92Y/E100W/K139C/I201C/A217G/K234V/N247D/H363R | 6 | 13 | 27 | 49 | 85 | 84 | 100 | 98 | 71 | 13 | 6 |
| P75N/K76N/D77Q/N78T/D92Y/E100W/K139C/I201C/A217G/K234V/N247D/Q256D/H363R | 6 | 15 | 30 | 51 | 81 | 82 | 100 | 98 | 76 | 20 | 5 |
| Y48H/D92Y/E100W/K139C/I201C/A217G/K234V/N247D/R289W/H363R | 8 | 11 | 25 | 44 | 78 | 88 | 100 | 99 | 68 | 10 | 2 |
| Q9S/N78Q/A89A/D92Y/H115M/A132V/K139C/Q162R/Q181L/I201C/A217G/K234V/P348R | 8 | 16 | 32 | 54 | 85 | 86 | 100 | 100 | 81 | 14 | 6 |
| Y48H/D92Y/E100W/K139C/I201C/A217G/K234V/N247D/Q256D/H363R | 3 | 12 | 24 | 46 | 77 | 89 | 85 | 100 | 75 | 14 | 1 |
| Y48H/D92Y/E100W/K139C/T152I/I201C/A217G/K234V/N247D/H363R | 4 | 12 | 24 | 45 | 76 | 92 | 87 | 100 | 66 | 14 | 4 |

TABLE 4-continued

Relative temperature profiles

| Phytase variant | Temperature (° C.) | | | | | | | | | | |
|---|---|---|---|---|---|---|---|---|---|---|---|
| | 20 | 30 | 40 | 50 | 60 | 65 | 70 | 75 | 80 | 85 | 90 |
| D92Y/E100W/K139C/I201C/A217G/K234V/N247W/Q256D/H363R | 9 | 16 | 22 | 47 | 70 | 81 | 89 | 100 | 78 | 24 | 6 |
| D92Y/E100W/K139C/D173N/P175S/I201C/A217G/K234V/N247D/Q256D/H363R | 6 | 16 | 37 | 52 | 81 | 89 | 88 | 100 | 37 | 9 | 3 |
| Y48H/D92Y/E100W/K139C/I201C/V208T/A217G/K234V/N247D/Q256D/H363R | 9 | 15 | 22 | 47 | 76 | 91 | 90 | 100 | 68 | 18 | 6 |
| Y48H/E54C/D92Y/A101C/K139C/I201C/A217G/K234V/N247D/R289W/H363R | 9 | 16 | 26 | 57 | 78 | 89 | 90 | 100 | 80 | 21 | 7 |
| Y48H/D92Y/E100W/K139C/I201C/A217G/K234V/N247W/Q256D/H363R | 9 | 12 | 19 | 46 | 68 | 76 | 85 | 100 | 77 | 29 | 4 |
| Y48H/D92Y/E100W/K139C/T152A/I201C/A217G/K234V/N247W/Q256D/H363R | 8 | 12 | 20 | 46 | 66 | 78 | 80 | 100 | 81 | 33 | 4 |
| Y48H/E54C/D92Y/A101C/K139C/T152A/I201C/A217G/K234V/N247D/R289W/H363R | 4 | 8 | 21 | 44 | 80 | 91 | 88 | 100 | 81 | 17 | 3 |
| Y48H/E54C/D92Y/A101C/K139C/I201C/A217G/K234V/N247W/R289W/H363R | 7 | 13 | 22 | 48 | 76 | 87 | 84 | 100 | 82 | 24 | 6 |
| Y48H/E54C/D92Y/A101C/K139C/T152A/I201C/A217G/K234V/N247W/R289W/H363R | 5 | 11 | 20 | 46 | 77 | 89 | 79 | 100 | 81 | 27 | 4 |

TABLE 5

Heat stability at 75° C., activity relative to maximum activity

| Mutation | Relative activity |
|---|---|
| wt | 24 |
| K131Q | 26 |
| Q162N/D138N | 26 |
| I294L | 26 |
| G72A | 26 |
| H143C/I201C | 26 |
| Q162R | 26 |
| I49L | 26 |
| E66C/L370C | 27 |
| T369S | 27 |
| I201V | 27 |
| K148R | 27 |
| A163K | 27 |
| S1QS | 27 |
| F8M | 27 |
| F8Y | 27 |
| T242S | 27 |
| K176R | 28 |
| S403N | 28 |
| S1P | 28 |
| E41Q | 28 |
| K131L | 29 |
| K207R | 29 |
| K207Q | 29 |
| G346S | 29 |
| T308A | 29 |
| S396K | 30 |
| L401N | 30 |
| I201G | 30 |
| P348R | 31 |
| E100W | 31 |
| K187E | 31 |
| N239R | 32 |
| A304V | 32 |
| S396D | 32 |
| T152G | 32 |
| K12R | 33 |
| I303L | 33 |
| Q162N | 34 |
| S192A | 35 |
| T369D | 35 |
| V130L/M137L/V146I/I201V/M260L/I266V | 35 |
| Q109G | 36 |
| N239K | 38 |
| K234V | 39 |
| K234E | 40 |
| H363R | 41 |
| S261A | 41 |
| A217G | 43 |
| E54C/A101C/K207Q | 55 |
| K45P | 59 |
| E54C/A101C | 64 |
| D33C/E54C/A101C/Y179C | 74 |
| E54C/A101C/K139C/I201C/K207Q | 84 |
| D92Y/E100W/A217G/H363R | 84 |
| E54C/A101C/K139C/I201C | 86 |
| K139C/I201C | 87 |
| S1QGPS/K26H/E54C/A101C/K139C/Q162N/G186S/I201C/K207Q/G346S | 90 |
| Y48H/E54C/D92Y/A101C/K139C/T152A/I201C/K207Q/V208T/A217G/K234V/N247D R289W/H363R | 92 |
| T35A/Y48H/E54C/P75N/K76N/D77Q/N78T/D92Y/A101C/K139C/T152A/I201C/A217G/K234V/N247D/R289W/H363R | 93 |
| Y48H/E54C/D92Y/A101C/K139C/T152A/I201C/V208T/A217G/K234V/N247D/R289/H363R | 95 |
| E54C/D92Y/A101C/K139C/I201C/A217G/H363R | 96 |
| E54C/D92Y/A101C/K139C/I201C/A217G/K234V/N247D/Q256D/H363R | 96 |

TABLE 5-continued

Heat stability at 75° C., activity relative to maximum activity

| Mutation | Relative activity |
|---|---|
| D92Y/E100W/K139C/I201C/A217G/K234V/N247D/H363R | 98 |
| P75N/K76N/D77Q/N78T/D92Y/E100W/K139C/I201C/A217G/K234V/N247D/Q256D/H363R | 98 |
| Y48H/D92Y/E100W/K139C/I201C/A217G/K234V/N247D/R289W/H363R | 99 |
| Q9S/N78Q/A89A/D92Y/H115M/A132V/K139C/Q162R/Q181L/I201C/A217G/K234V/P348R | 100 |
| Y48H/D92Y/E100W/K139C/I201C/A217G/K234V/N247D/Q256D/H363R | 100 |
| Y48H/D92Y/E100W/K139C/T152I/I201C/A217G/K234V/N247D/H363R | 100 |
| D92Y/E100W/K139C/I201C/A217G/K234V/N247W/Q256D/H363R | 100 |
| D92Y/E100W/K139C/D173N/P175S/I201C/A217G/K234V/N247D/Q256D/H363R | 100 |
| Y48H/D92Y/E100W/K139C/I201C/V208T/A217G/K234V/N247D/Q256D/H363R | 100 |
| Y48H/E54C/D92Y/A101C/K139C/I201C/A217G/K234V/N247D/R289W/H363R | 100 |
| Y48H/D92Y/E100W/K139C/I201C/A217G/K234V/N247W/Q256D/H363R | 100 |
| Y48H/D92Y/E100W/K139C/T152A/I201C/A217G/K234V/N247W/Q256D/H363R | 100 |
| Y48H/E54C/D92Y/A101C/K139C/T152A/I201C/A217G/K234V/N247D/R289W/H363R | 100 |
| Y48H/E54C/D92Y/K139C/I201C/A217G/K234V/N247W/R289W/H363R | 100 |
| Y48H/E54C/D92Y/A101C/K139C/T152A/I201C/A217G/K234V/N247W/R289W/H363R | 100 |

Example 6 pH Profile

The pH profile was determined at 37° C. in the pH range of 2.0 to 7.5 (in 0.5 pH-unit steps) as described above in the section "Determination of phytase activity", except that a buffer cocktail (50 mM glycine, 50 mM acetic acid and 50 mM Bis-Tris was used instead of the 0.25 M sodium acetate pH 5.5 buffer. The results are summarized in table 1 below. The values given for each pH in the range of 2.0-7.5 are the relative activity in % normalized to the value at optimum.

TABLE 6

Relative pH profiles at 37° C.

| Mutation | pH | | | | | | | | | | | |
|---|---|---|---|---|---|---|---|---|---|---|---|---|
| | 2 | 2.5 | 3 | 3.5 | 4 | 4.5 | 5 | 5.5 | 6 | 6.5 | 7 | 7.5 |
| K26P | 72 | 89 | 100 | 96 | 81 | 67 | 55 | 37 | 21 | 8 | 1 | 3 |
| K26Q | 40 | 69 | 91 | 100 | 98 | 95 | 84 | 59 | 35 | 12 | −1 | 1 |
| K26R | 48 | 66 | 85 | 100 | 99 | 98 | 87 | 64 | 40 | 14 | 2 | −1 |
| D92Y/E100W/A217G/H363R | 63 | 78 | 94 | 100 | 95 | 76 | 46 | 20 | 7 | 1 | −1 | 9 |
| Q9S/N78Q/A89A/D92Y/H115M/A132V/K139C/Q162R/Q181L/I201C/A217G/K234V/P348R | 50 | 68 | 90 | 100 | 99 | 79 | 42 | 17 | 3 | 0 | 0 | 5 |
| T35C/L172C | 39 | 65 | 87 | 100 | 99 | 94 | 73 | 51 | 30 | 10 | 1 | 1 |
| D92Y/E100W/A217G/H363R | 63 | 78 | 94 | 100 | 95 | 76 | 46 | 20 | 7 | 1 | −1 | 9 |
| Q9S/N78Q/A89A/D92Y/H115M/A132V/K139C/Q162R/Q181L/I201C/A217G/K234V/P348R | 50 | 68 | 90 | 100 | 99 | 79 | 42 | 17 | 3 | 0 | 0 | 5 |
| H143C/I201C | 49 | 71 | 89 | 100 | 93 | 90 | 77 | 55 | 33 | 12 | 2 | 0 |
| Y48H/E54C/D92Y/A101C/K139C/I201C/A217G/K234V/N247D/R289W/H363R | 42 | 65 | 89 | 100 | 98 | 85 | 53 | 21 | 7 | 1 | 0 | −1 |
| Y48H/E54C/D92Y/A101C/K139C/T152A/I201C/A217G/K234V/N247W/R289W/H363R | 47 | 62 | 89 | 100 | 97 | 85 | 52 | 18 | 6 | 0 | 0 | 0 |
| T35A/Y48H/E54C/P75N/K76N/D77Q/N78T/D92Y/A101C/K139C/T152A/I201C/A217G/K234V/N247D/R289W/H363R | 41 | 74 | 88 | 100 | 96 | 78 | 49 | 17 | 5 | 0 | −1 | −2 |
| Y48H/E54C/D92Y/A101C/K139C/T152A/I201C/ | 39 | 70 | 87 | 100 | 94 | 82 | 52 | 21 | 7 | 2 | 1 | −1 |

TABLE 6-continued

Relative pH profiles at 37° C.

| Mutation | pH | | | | | | | | | | | |
|---|---|---|---|---|---|---|---|---|---|---|---|---|
| | 2 | 2.5 | 3 | 3.5 | 4 | 4.5 | 5 | 5.5 | 6 | 6.5 | 7 | 7.5 |
| A217G/K234V/ N247D/R289W/ H363R | | | | | | | | | | | | |
| E54C/D92Y/A101C/ K139C/I201C/ A217G/H363R | 40 | 65 | 87 | 100 | 99 | 88 | 57 | 23 | 7 | 1 | 0 | −1 |
| Y48H/E54C/D92Y/ A101C/K139C/ T152A/I201C/ V208T/A217G/ K234V/N247D/ R289W/H363R | 40 | 70 | 84 | 100 | 98 | 90 | 65 | 29 | 11 | 3 | 1 | −1 |
| K131P | 50 | 64 | 83 | 95 | 100 | 99 | 95 | 83 | 65 | 36 | 5 | 3 |
| K131Q | 51 | 67 | 82 | 98 | 100 | 99 | 95 | 80 | 69 | 39 | 7 | −2 |
| K207R | 38 | 51 | 71 | 85 | 100 | 97 | 95 | 81 | 50 | 27 | 3 | 3 |
| D33C/Y179C | 40 | 53 | 72 | 86 | 100 | 92 | 83 | 65 | 38 | 18 | 2 | 5 |
| G325C/T358C | 40 | 54 | 78 | 93 | 100 | 100 | 90 | 68 | 41 | 16 | 0 | −3 |
| H228C/H363C | 36 | 53 | 75 | 92 | 100 | 97 | 88 | 67 | 38 | 16 | 2 | −1 |
| A150C/L259C | 36 | 57 | 78 | 95 | 100 | 97 | 89 | 64 | 42 | 16 | 3 | −2 |
| D92Y/E100W/ K139C/I201C/ A217G/N247D/ H363R | 58 | 73 | 90 | 99 | 100 | 84 | 49 | 20 | 6 | 1 | −1 | 3 |
| D92Y/E100W/ K139C/I201C/ A217G/K234V/ N247D/H363R | 58 | 73 | 90 | 99 | 100 | 84 | 49 | 20 | 6 | 1 | −1 | 3 |
| T308A | 39 | 58 | 79 | 99 | 100 | 94 | 85 | 76 | 55 | 36 | 4 | −3 |
| E54C/A101C | 42 | 55 | 77 | 98 | 100 | 90 | 85 | 63 | 40 | 15 | 2 | 1 |
| Y48H/D92Y/E100W/ K139C/T152I/I201C/ A217G/K234V/ N247D/H363R | 54 | 68 | 84 | 98 | 100 | 93 | 54 | 20 | 5 | 0 | 0 | −6 |
| K131Q | 51 | 67 | 82 | 98 | 100 | 99 | 95 | 80 | 69 | 39 | 7 | −2 |
| I49L | 40 | 62 | 83 | 97 | 100 | 94 | 80 | 58 | 37 | 14 | 2 | −1 |
| Y48H/E54C/D92Y/ A101C/K139C/ I201C/A217G/ K234V/N247W/ R289W/H363R | 42 | 62 | 87 | 96 | 100 | 81 | 50 | 22 | 6 | 0 | 0 | −1 |
| Q162N | 40 | 66 | 75 | 96 | 100 | 93 | 91 | 73 | 47 | 22 | 6 | 1 |
| Y48H/D92Y/E100W/ K139C/201C/ A217G/K234V/ N247D/R289W/ H363R | 46 | 69 | 86 | 95 | 100 | 79 | 55 | 23 | 9 | 2 | 0 | 0 |
| Y48H/D92Y/E100W/ K139C/T152A/ I201C/A217G/ K234V/N247W/ Q256D/H363R | 41 | 59 | 75 | 94 | 100 | 95 | 66 | 24 | 6 | 1 | 0 | −1 |
| E66C/L370C | 33 | 58 | 80 | 94 | 100 | 100 | 87 | 66 | 41 | 14 | 2 | 0 |
| E41Q | 44 | 62 | 78 | 93 | 100 | 97 | 86 | 68 | 41 | 17 | 3 | 0 |
| Q109G | 37 | 57 | 77 | 92 | 100 | 100 | 96 | 73 | 48 | 23 | 4 | 0 |
| A163K | 47 | 63 | 75 | 92 | 100 | 99 | 89 | 67 | 41 | 13 | 3 | 0 |
| Y48H/D92Y/E100W/ K139C/I201C/ A217G/K234V/ N247D/Q256D/ H363R | 50 | 55 | 72 | 91 | 100 | 91 | 57 | 19 | 4 | −1 | −1 | −1 |
| A304V | 53 | 60 | 82 | 91 | 100 | 95 | 88 | 68 | 45 | 19 | 3 | 3 |
| E54C/D92Y/A101C/ K139C/I201C/ A217G/K234V/ N247D/Q256D/ H363R | 35 | 48 | 68 | 90 | 100 | 94 | 64 | 22 | 6 | 0 | −1 | −1 |
| P75N/K76N/D77Q/ N78T/D92Y/E100W/ K139C/I201C/ A217G/K234V/ N247D/Q256D/ H363R | 42 | 55 | 71 | 88 | 100 | 95 | 62 | 23 | 6 | 0 | 0 | 0 |
| D92Y/E100W/ K139C/I201C/ | 37 | 51 | 65 | 89 | 100 | 97 | 69 | 20 | 2 | −3 | −5 | −4 |

TABLE 6-continued

Relative pH profiles at 37° C.

| Mutation | pH | | | | | | | | | | | |
|---|---|---|---|---|---|---|---|---|---|---|---|---|
| | 2 | 2.5 | 3 | 3.5 | 4 | 4.5 | 5 | 5.5 | 6 | 6.5 | 7 | 7.5 |
| A217G/K234V/N247W/Q256D/H363R Y48H/D92Y/T98S/E100W/K139C/T152A/I201C/A217G/K234V/N247W/Q256D/H363R | 39 | 50 | 69 | 89 | 100 | 99 | 73 | 28 | 8 | 0 | −1 | −1 |
| K234E | 44 | 53 | 75 | 88 | 100 | 99 | 95 | 71 | 47 | 19 | 3 | 1 |
| D92Y/E100W/K139C/D173N/P175S/I201C/A217G/K234V/N247D/Q256D/H363R | 44 | 54 | 70 | 87 | 100 | 93 | 62 | 22 | 5 | 1 | 0 | −1 |
| K207R | 38 | 51 | 71 | 85 | 100 | 97 | 95 | 81 | 50 | 27 | 3 | 3 |
| D33C/E54C/A101C/Y179C | 37 | 59 | 74 | 84 | 100 | 88 | 82 | 65 | 41 | 21 | 5 | 2 |
| Q162N/D138N | 39 | 58 | 81 | 95 | 100 | 100 | 91 | 71 | 47 | 21 | 4 | 3 |
| Q162R | 38 | 58 | 78 | 88 | 100 | 100 | 96 | 72 | 48 | 22 | 3 | 0 |
| N285D | 45 | 61 | 81 | 96 | 100 | 100 | 97 | 71 | 39 | 18 | 2 | 7 |
| E66C/L370C | 33 | 58 | 80 | 94 | 100 | 100 | 87 | 66 | 41 | 14 | 2 | 0 |
| T369S | 46 | 56 | 79 | 92 | 100 | 100 | 94 | 72 | 47 | 22 | 3 | −1 |
| S192A | 46 | 58 | 81 | 90 | 100 | 100 | 93 | 62 | 42 | 15 | 2 | 0 |
| Y48H/E54C/D92Y/A101C/K139C/T152A/I201C/K207Q/V208T/A217G/K234V/N247D/R289W/H363R | 36 | 63 | 83 | 96 | 100 | 100 | 85 | 61 | 36 | 14 | 2 | −1 |
| wild type | 41 | 57 | 77 | 93 | 99 | 100 | 94 | 75 | 48 | 20 | 3 | 0 |
| K131L | 45 | 59 | 75 | 93 | 98 | 100 | 96 | 84 | 71 | 44 | 13 | −1 |
| D33C/P178C | 37 | 61 | 77 | 90 | 94 | 100 | 88 | 66 | 43 | 15 | 1 | 1 |
| F63C/L368C | 29 | 55 | 78 | 92 | 98 | 100 | 83 | 65 | 38 | 14 | 2 | −1 |
| S1QS | 45 | 56 | 80 | 86 | 99 | 100 | 83 | 63 | 45 | 14 | 3 | 0 |
| I303L | 40 | 59 | 75 | 89 | 98 | 100 | 91 | 73 | 45 | 18 | 2 | 0 |
| F8Y | 44 | 59 | 78 | 93 | 98 | 100 | 88 | 64 | 37 | 14 | 3 | −4 |
| I201V | 36 | 53 | 73 | 91 | 98 | 100 | 88 | 68 | 40 | 13 | −1 | −2 |
| Y48H/D92Y/E100W/K139C/I201C/V208T/A217G/K234V/N247D/Q256D/H363R | 46 | 60 | 76 | 88 | 98 | 100 | 74 | 35 | 10 | 1 | 0 | 1 |
| K176R | 38 | 58 | 76 | 90 | 97 | 100 | 94 | 72 | 45 | 18 | 0 | −4 |
| S1P | 46 | 56 | 80 | 90 | 97 | 100 | 84 | 64 | 40 | 15 | 2 | −2 |
| T242S | 38 | 58 | 73 | 85 | 97 | 100 | 97 | 73 | 48 | 22 | 2 | −1 |
| S396D | 41 | 54 | 76 | 87 | 97 | 100 | 93 | 71 | 47 | 19 | 4 | 0 |
| F8M | 48 | 57 | 71 | 90 | 96 | 100 | 82 | 70 | 40 | 14 | 5 | 1 |
| N239R | 32 | 46 | 69 | 93 | 96 | 100 | 98 | 74 | 50 | 24 | 1 | 2 |
| N239K | 38 | 52 | 70 | 91 | 96 | 100 | 95 | 73 | 48 | 20 | 3 | 0 |
| S396K | 37 | 51 | 72 | 87 | 96 | 100 | 96 | 73 | 46 | 21 | 3 | −1 |
| K139C/I201C | 34 | 48 | 69 | 84 | 96 | 100 | 94 | 72 | 45 | 17 | 1 | −2 |
| K148R | 35 | 57 | 70 | 90 | 95 | 100 | 92 | 75 | 47 | 15 | 1 | −1 |
| P348R | 38 | 54 | 73 | 91 | 95 | 100 | 98 | 72 | 48 | 25 | 3 | 1 |
| I201G | 36 | 52 | 73 | 93 | 95 | 100 | 89 | 68 | 41 | 14 | −1 | −5 |
| V130L/M137L/V146I/I201V/M260L/I266V | 32 | 53 | 69 | 88 | 95 | 100 | 89 | 71 | 52 | 26 | 8 | 2 |
| T152G | 30 | 50 | 67 | 84 | 94 | 100 | 95 | 73 | 47 | 19 | 2 | 0 |
| L401N | 30 | 50 | 63 | 87 | 94 | 100 | 100 | 72 | 50 | 23 | 2 | 1 |
| I294L | 37 | 53 | 78 | 83 | 93 | 100 | 94 | 73 | 46 | 20 | 2 | −1 |
| G346S | 34 | 55 | 71 | 86 | 93 | 100 | 90 | 69 | 43 | 18 | 2 | −5 |
| H363R | 29 | 50 | 67 | 87 | 92 | 100 | 96 | 77 | 49 | 22 | 2 | 0 |
| T369D | 35 | 54 | 68 | 82 | 92 | 100 | 90 | 72 | 51 | 18 | 3 | 0 |
| G72A | 35 | 47 | 67 | 85 | 90 | 100 | 80 | 61 | 37 | 14 | −1 | −2 |
| E54C/A101C/K139C/I201C | 37 | 49 | 75 | 87 | 90 | 100 | 89 | 66 | 50 | 23 | 6 | 0 |
| S261A | 30 | 46 | 69 | 83 | 90 | 100 | 84 | 67 | 43 | 19 | −1 | −3 |
| K187E | 34 | 57 | 72 | 88 | 89 | 100 | 92 | 70 | 44 | 21 | 1 | −1 |
| E54C/A101C/K139C/I201C/K207Q | 28 | 48 | 65 | 79 | 89 | 100 | 98 | 85 | 71 | 47 | 18 | 1 |

TABLE 6-continued

Relative pH profiles at 37° C.

| Mutation | 2 | 2.5 | 3 | 3.5 | 4 | 4.5 | 5 | 5.5 | 6 | 6.5 | 7 | 7.5 |
|---|---|---|---|---|---|---|---|---|---|---|---|---|
| A217G | 39 | 54 | 73 | 85 | 88 | 100 | 85 | 59 | 39 | 14 | −1 | −1 |
| K207L | 41 | 52 | 69 | 84 | 92 | 98 | 100 | 92 | 69 | 41 | 11 | 1 |
| K207Q | 38 | 49 | 69 | 83 | 95 | 95 | 100 | 92 | 65 | 45 | 10 | 5 |
| S403N | 33 | 51 | 72 | 85 | 99 | 99 | 100 | 77 | 49 | 22 | 1 | −1 |
| K45P | 34 | 60 | 72 | 90 | 91 | 98 | 100 | 75 | 48 | 23 | 2 | 0 |
| E100W | 29 | 44 | 69 | 78 | 93 | 98 | 100 | 84 | 57 | 28 | 3 | 0 |
| S1QGPS/K26H/ E54C/A101C/ K139C/Q162N/G186S/ I201C/K207Q/G346S | 38 | 54 | 69 | 83 | 92 | 98 | 100 | 88 | 64 | 29 | 2 | −1 |
| K234V | 35 | 54 | 65 | 94 | 93 | 96 | 100 | 74 | 44 | 26 | 3 | 1 |
| E54C/A101C/K207Q | 34 | 52 | 70 | 85 | 96 | 96 | 100 | 92 | 76 | 47 | 14 | 1 |
| K207Q | 38 | 49 | 69 | 83 | 95 | 95 | 100 | 92 | 65 | 45 | 10 | 5 |

Example 7

Steam Stability

Method 1

Residual activity of phytase molecules after steam treatment was evaluated using the following assay:

20 microliters of each purified enzyme sample is dispensed into a single well of a Corning® 96 Well (1×8 Stripwell™) plate (Corning, Lowell, Mass., USA) and subsequently evaporated to dryness in a vacuum centrifuge (Genevac EZ-1 Plus, Genevac Ltd, Suffolk, UK). The steam incubation is performed in a closed styropor container with the inner dimensions 27×18×20 cm. The samples, in open strips, are placed approximately 10 cm above the bottom of the container on a metal rack, in order not to be in contact with the water.

One liter of boiling water is poured into the container, the lid is closed and the temperature of the produced steam monitored using a thermometer mounted in the lid of the container. The incubation proceeds for 60 seconds from the moment the water is poured into the container. During this period the temperature increases to about 85° C. Immediately after the incubation the samples are cooled down on ice, re-suspended and evaluated with respect to phytase activity using the colorimetric p-nitrophenyl phosphate (pNPP) assay (Sigma, Broendby, DK). Each enzyme sample is compared to a similar sample that had not been steam treated in order to calculate residual activity.

The results are presented in Tables 7 and 8 below.

TABLE 7

Steam Stability determined by method 1

| Variant | Residual Activity [%] |
|---|---|
| Experiment 1 | Wt 12 |
| E66C/L370C | 23 |
| D33C/E54C/A101C/Y179C | 22 |
| Experiment 2 | Wt 14 |
| G346S | 25 |
| Q109G | 22 |
| H143C/I201C | 16 |
| Experiment 3 | Wt 10 |
| Q162N (performed twice) | 31; 35 |
| Experiment 4 | Wt 20 |
| E54C/D92Y/A101C/K139C/I201C/A217G/H363R | 88 |
| Q9S/N78Q/A89A/D92Y/H115M/A132V/K139C/ Q162R/Q181L/I201C/A217G/K234V/P348R | 62 |
| D92Y/E100W/K139C/I201C/A217G/N247D/H363R | 51 |
| D92Y/E100W/K139C/I201C/A217G/N247D/Q256D/ H363R | 54 |
| Y48H/D92Y/E100W/K139C/T152I/I201C/A217G/ K234V/N247D/H363R | 45 |
| Y48H/D92Y/T98S/E100W/K139C/T152A/I201C/ A217G/K234V/N247D/Q256D/H363R | 86 |
| E54C/D92Y/A101C/K139C/I201C/A217G/K234V/ N247D/Q256D/H363R | 91 |
| Y48H/D92Y/E100W/K139C/T152A/I201C/A217G/ K234V/N247W/Q256D/H363R | 88 |
| Y48H/E54C/D92Y/A101C/K139C/T152A/I201C/ A217G/K234V/N247D/R289W/H363R | 90 |
| Y48H/E54C/D92Y/A101C/K139C/T152A/I201C/ V208T/A217G/K234V/N247D/R289W/H363R | 95 |
| T35A/Y48H/E54C/P75N/K76N/D77Q/N78T/D92Y/ A101C/K139C/T152A/I201C/A217G/K234V/ N247D/R289W/H363R | 81 |
| Y48H/E54C/D92Y/A101C/K139C/T152A/I201C/ K207Q/V208T/A217G/K234V/N247D/R289W/H363R | 95 |
| Experiment 5 | Wt 25.9 |
| D92Y/E100W/A217G/H363R | 39.5 |
| D92Y/E100W/K139C/I201C/A217G/N247D/H363R | 57.5 |
| Q9S/N78Q/A89A/D92Y/H115M/A132V/K139C/ Q162R/Q181L/I201C/A217G/K234V/P348R | 68.5 |

Method 2

In these experiments a modified set-up was used whereby the steam is provided from a steam generator and led into the box. The samples placed on a plate are inserted into the box through a drawer when the temperature has reached. Upon the insertion of the samples the temperature drops 4° C. Incubation is performed for 30 seconds while the temperature remains approximately constant at 90° C. Thereafter the plate is quickly removed from the box and the samples placed on ice. The samples are analyzed as in method 1.

TABLE 8

Steam Stability determined by method 2

| Variant | Residual Activity [%] |
|---|---|
| Experiment 1 | Wt 15 |
| V130L/M137L/V146I/I201V/M260L/I266V | 27 |
| Experiment 2 | Wt 6 |
| S1QGPS/K26H/E54C/A101C/K139C/Q162N/ G186S/I201C/K207Q/G346S | 29 |
| Experiment 3 | Wt 4 |
| S261A | 12 |
| T308A | 9 |
| Experiment 4 | wt 8 |
| L401N | 14 |
| S403N | 9 |
| T308A | 11 |
| Experiment 5 | wt 4 |
| E54C/A101C | 9 |
| Experiment 6 | wt 6 |
| T152G | 10 |
| Experiment 7 | wt 5 |
| S1P | 10 |
| F8M | 14 |
| Experiment 8 | wt 3 |
| K139C/I201C | 13 |
| Experiment 9 | wt 5 |
| S1QS | 9 |
| A217G | 9 |

Example 8

Glycation Residual Activity

Inactivation by Glycation

The effect of glycation was investigated by incubation of purified phytase variants with glucose. For this 0.5 mg/ml enzyme in 0.1 M HEPES pH 7.5 was mixed with 1 M glucose and incubated at 50° C. for 5 hr. The phosphatase activity was measured before and after incubation and the results indicated below in Table 9.

TABLE 9

Modification of Glycation.

| Mutation | Residual activity |
|---|---|
| Wt | 18% |
| K26Q | 55% |
| K26R | 47% |

The results shown above indicate the wild type enzyme is strongly inhibited by glycation (18% residual activity). Variants at position K26 are clearly much improved in this respect being less affected.

Example 9

Pelleting Stability Tests

Measurements of Pelleting Stability

Approximately 50 g enzyme granulate was pre-mixed with 10 kg feed for 10 minutes in a small horizontal mixer. This premix was mixed with 90 kg feed for 10 minutes in a larger horizontal mixer. From the mixer the feed was led to the conditioner (a cascade mixer with steam injection) at a rate of approximately 300 kg/hour. The conditioner heated up the feed to 95° C. (measured at the outlet) by injecting steam. The residence time in the conditioner was 30 seconds. From the conditioner the feed was led to a Simon Heesen press equipped with 3.0×35 mm horizontal die and pressed to pellets with a length of around 15 mm. After the press the pellets were placed in an air cooler and cooled for 15 minutes.

Feed Formulation:
74.0% Grind corn
5.0% soy oil
20.7% Toasted soy grits
0.3% Solivit Mikro 106 premix of minerals and vitamins
12% water content Test 1
A powder consisting of:
1.5 kg fibrous cellulose, Arbocel BC200
0.75 kg carbohydrate binder, Avedex W80
11.552 kg finely ground sodium sulphate
is granulated in a Lodige mixer FM 50 with a granulation liquid consisting of:
0.75 kg carbohydrate binder, Avedex W80
2.49 kg Phytase *Hafnia* wt concentrate
0.45 kg water The granulation is performed in a manner as described in U.S. Pat. No. 4,106,991, Example 1. The obtained granulate is dried in a fluid bed to a water content below 1% and sifted to obtain a product with the particle range 250 micro-m to 850 micro-m. Finally, the product is coated with 10% palm oil and 22% calcium carbonate in a manner as described in U.S. Pat. No. 4,106,991, Example 22.

Test 2
A powder consisting of:
1.6 kg fibrous cellulose, Arbocel BC200
0.80 kg carbohydrate binder, Avedex W80
12.027 kg finely ground sodium sulphate
is granulated in a Lödige mixer FM 50 with a granulation liquid consisting of:
0.80 kg carbohydrate binder, Avedex W80
3.5 kg Y48H/D92Y/E100W/K139C/T152C/I201C/A217G/K234V/N247D/H363R variant concentrate
0.02 kg water The granulation, drying and sifting is performed as above. Finally, the product is coated with 9% palm oil and 22% calcium carbonate in a manner as above.

Test 3
A powder consisting of:
1.6 kg fibrous cellulose, Arbocel BC200
0.80 kg carbohydrate binder, Avedex W80
12.013 kg finely ground sodium sulphate
is granulated in a Lödige mixer FM 50 with a granulation liquid consisting of:
0.80 kg carbohydrate binder, Avedex W80
3.2 kg phytase variant 2 concentrate
0.30 kg water The granulation, drying and sifting is performed as above. Finally, the product is coated with 9.8% palm oil and 22% calcium carbonate in a manner as above.

Test 4
A powder consisting of:
1.6 kg fibrous cellulose, Arbocel BC200
0.80 kg carbohydrate binder, Avedex W80
12.225 kg finely ground sodium sulphate
is granulated in a Lödige mixer FM 50 with a granulation liquid consisting of:
0.80 kg carbohydrate binder, Avedex W80
3.50 kg E54C/D92Y/A101C/K139C/I201C/A217G/H363R variant concentrate The granulation, drying and sifting is performed as above. Finally, the product is coated with 9.0% palm oil and 22% calcium carbonate in a manner as above.

Test 5
A powder consisting of:
1.6 kg fibrous cellulose, Arbocel BC200
0.80 kg carbohydrate binder, Avedex W80
12.225 kg finely ground sodium sulphate
is granulated in a Lödige mixer FM 50 with a granulation liquid consisting of:
0.80 kg carbohydrate binder, Avedex W80
3.50 kg Y48H/D92Y/E100W/K139C/I201C/A217G/K234V/N247D/Q256D/H363R variant concentrate The granulation, drying and sifting is performed as above. Finally, the product is coated with 9.0% palm oil and 22% calcium carbonate in a manner as above.

Test 6
A powder consisting of:
1.6 kg fibrous cellulose, Arbocel BC200
0.80 kg carbohydrate binder, Avedex W80
12.435 kg finely ground sodium sulphate
is granulated in a Lödige mixer FM 50 with a granulation liquid consisting of:
0.80 kg carbohydrate binder, Avedex W80
3.50 kg Y48H/D92Y/E100W/K139C/T152A/I201C/A217G/K234V/N247W/Q256D/H363R variant concentrate
0.30 kg water The granulation, drying and sifting is performed as above. Finally, the product is coated with 9.7% palm oil and 22% calcium carbonate in a manner as above.

Test 7
A powder consisting of:
1.6 kg fibrous cellulose, Arbocel BC200
0.80 kg carbohydrate binder, Avedex W80
12.193 kg finely ground sodium sulphate
is granulated in a Lödige mixer FM 50 with a granulation liquid consisting of:
0.64 kg carbohydrate binder, Avedex W80
3.50 kg phytase variant 5 concentrate
0.16 kg water The granulation, drying and sifting is performed as above. Finally, the product is coated with 8.3% palm oil and 22% calcium carbonate in a manner as above.

The samples produced in Test 1 to Test 7 were tested in a pelleting trial at 95° C., outlet of the conditioner. The phytase content was measured using analytical method EB-SM 0559.02 version 01 (available from Novozymes upon request) prior to pelletizing and in the feed pellets after pelletizing. The following residual activities of the phytase were found:

TABLE 10

| | Pelleting Stability | |
|---|---|---|
| Test | Residual phytase activity [%] | Variant |
| 1 | 13 | Wt |
| 2 | 26 | Y48H/D92Y/E100W/K139C/T152I/I201C/A217G/K234V/N247D/H363R |
| 3 | 20 | D92Y E100W K139C I201C A217G K234V N247D H363R |
| 4 | 30 | E54C/D92Y/A101C/K139C/I201C/A217G/H363R |
| 5 | 26 | Y48H/D92Y/E100W/K139C/I201C/A217G/K234V/N247D/Q256D/H363R |
| 6 | 28 | Y48H/D92Y/E100W/K139C/T152A/I201C/A217G/K234V/N247W/Q256D/H363R |
| 7 | 43 | Y48H/E54C/D92Y/A101C/K139C/T152A/I201C/A217G/K234V/N247D/R289W/H363R |

The conclusion is that the variants have improved the pelleting stability compared to the reference Test 1.

Example 10

Performance in Animal Feed in an In Vitro Model

The performance in animal feed of a number of phytase variants of the invention are compared in an in vitro model to the performance of a reference protein such as SEQ ID NO:2. The in vitro model simulates gastro-intestinal conditions in a monogastric animal and correlates well with results obtained in animal trials in vivo. The version used in this example simulates the crop and stomach of a broiler. The comparison is performed as follows:

Phytase activity in the variant sample is determined as described in Example 1 under "Determination of phytase activity".

Feed pellets from a broiler feeding trial—and with maize, soybean meal and soybean oil as main constituents—are pre-incubated at 40° C. and pH 4.6 for 5 minutes followed by the addition of suitable dosages of the phytases (identical dosages are used for all phytases to be tested to allow comparison), for example between 125 to 1000 phytase units FYT/kg feed, or buffer in the control samples. After 5 minutes of incubation, pepsin (3000 U/g feed) in an HCl-solution is added and in this way pH is reduced to 3. The samples are then incubated at 40° C. for another 5 minutes.

The reactions are stopped and phytic acid and inositol-phosphates extracted by addition of HCl to a final concentration of 0.5 M and incubation at 40° C. for 2 hours, followed by one freeze-thaw cycle and 1 hour incubation at 40° C.

Phytic acid and inositol-phosphates are separated by high performance ion chromatography as described by Chen et al., 2003, *Journal of Chromatography A* 1018: 41-52 and quantified as described by Skoglund et al., 1997, *J. Agric. Food Chem.* 45: 431-436.

Degradation of phytate is then calculated as the difference in inositol-6-phosphate bound phosphorous (IP6-P) between phytase-treated and non-treated samples. The relative performance of the variant is calculated as the percentage of phytate degradation by the wild type phytase.

The relative degradation of the phytase variants (Table 11) show that the variants are all capable of degrading inositol-6-phosphate in the in vitro system applied. Certain candidates performed better than the wild type (e.g., variant: D92Y/E100W/A217G/H363R, variant: Y48H/D92Y/E100W/K139C/I201C/A217G/K234V/N247D/Q256D/H363R, variant: Y48H/D92Y/E100W/K139C/T152C/I201C/A217G/K234V/N247D/H363R) whereas others were not as efficient in vitro as the wild type (e.g., variant: K207Q).

TABLE 11

In vitro degradation of IP6-P from a soybean/maize based diet. Phytate degradation of the variant is calculated as the percentage of phytate degradation by the wild type phytase.

| Phytase variant | Phytase dosage (FYT/kg feed) | Phytate degradation of the variant as percentage of phytate degradation by the wild type (two numbers represent data from two different trials) |
|---|---|---|
| D92Y/E100W/A217G/H363R | 125 | 181 |
| As above | 250 | 199 |
| D92Y/E100W/K139C/I201G/A217G/K234V/N247D/H363R | 125 | 74; 101 |
| As above | 250 | 71; 137 |
| As above | 500 | 72 |
| As above | 1000 | 76 |
| Y48H/D92Y/E100W/K139C/I201C/A217G/K234V/N247D/Q256D/H363R | 125 | 252; 543 |
| As above | 250 | 219; 347 |
| As above | 500 | 184; 215 |
| Y48H/D92Y/E100W/K139C/T152I/I201C/A217G/K234V/N247D/H363R | 125 | 237; 297 |
| As above | 250 | 160; 246 |
| As above | 500 | 148; 197 |
| K207Q | 250 | 57 |
| E54C/A101C | 250 | 119 |
| G346S | 250 | 79 |
| Q162N | 250 | 180 |
| S1QS | 255 | 68* |
| S1P | 277 | 70* |
| F8M | 246 | 74* |
| F8Y | 229 | 71* |
| K139C/I201C | 250 | 105 |
| S1QGPS/K26H/E54C/A101C/K139C/Q162N/G186S/I201C/K207Q/G346S | 250 | 90 |

*For these data the wt was tested at 250 FYT/kg

Example 11

Performance in an In Vivo Pig Trial

Comparative evaluation of the effects of graded amounts of two *Hafnia alveii* phytase variants on the faecal digestibility and excretion of phosphorus and calcium in growing pigs.

Sixty four Large White×Landrace pigs having an initial body weight of 43.55±4.35 kg were used.

The animals were housed in floor-pen cages in an environmentally controlled room. Each pen had a plastic-coated welded wire floor and was equipped with two water nipples and four stainless-stee individualized feeders. Room temperature was 21-22° C. and humidity percentage was 50%.

The pigs were fed a basal diet formulated to provide phosphorus (P) exclusively from vegetable origin during an adaptive period of 14 days. After that period they were allocated into 16 equal groups of 4 animals each.

They were fed for 12 days the basal diet or this diet supplemented with 1000, 2000 U/kg and 4000 U/kg of *Hafnia alveii* wild type phytase, with 500, 1000 and 2000 U/kg of the Y48H/D92Y/E100W/K139C/I201C/A217G/K234V/N247D/Q256D/H363R variant or with 500, 1000 and 2000 U/kg of the Y48H/D92Y/E100W/K139C/T152C/I201C/A217G/K234V/N247D/H363R variant.

An indigestible tracer (chromium oxide) was added at a concentration of 0.4% to all the diets allowing calculation of the digestibility of P and calcium (Ca). The feed was distributed ad libitum in mash form, under pen feed consumption control, and the animals had free access to drinking water. The digestibility of Ca was not corrected for Ca intake with the drinking water.

Faecal P, Ca and Cr concentrations were measured at the 12$^{th}$ day of the second period. Faeces were sampled individually, in approximately the same amount at the same time of the day, during the last 3 days preceding that date. Thus, for each dietary treatment and for each criterion a total of 12 individual determinations have been performed. All minerals were determined according to standard Association of Official Analytical Chemists (1990) methods using a Vista-MPX ICP-OES spectrometer. The apparent digestibility (% of the intake) of the minerals was calculated for the mentioned 3 day period.

The mean P faecal concentration of the enzyme supplemented animals was very significantly lower than that observed for the animals ingesting the control diet (a).

The P digestibility was dose depend and highly significantly improved with the five phytases in all supplemented groups (b). The highest P digestibility was observed in the 4000 U/kg *Hafnia alvei* wild type supplemented diet and in the JHP113 group at 2000 U/kg.

The faecal excretion of P was significantly reduced in all the phytase supplemented animals and for all the tested inclusion levels (c).

The apparent absorbed P was higher than the 2.25 g/kg recommended for the growing pigs in the 4000 U/kg *Hafnia alvei* wild type group and very close to it with JHP113 and "*C. braakii*" wild type at 2000 U/kg and 4000 U/kg respectively (d).

The P equivalences, considered as supplemental P digested comparatively to the non-supplemented control, were highly significantly greater to the control in all five phytases supplemented diets (e).

The Ca digestibility was improved and the Ca faecal excretion reduced with all tested enzymes and at all inclusion levels (f).

The maximum of efficiency on these parameters was observed with *Hafnia alvei* wild type at the inclusion level of 4000 U/kg, whereas the Y48H/D92Y/E100W/K139C/I201C/A217G/K234V/N247D/Q256D/H363R variant performed the best when comparing the efficacy at the 1000 U/kg and 2000 U/kg supplementations.

The results are presented in the following Table 12

TABLE 12

Residual levels of parameters for digestibility

| | Dose (U/kg) | | | |
|---|---|---|---|---|
| | 0 | 500 | 1000 | 2000 |
| (a) Phosphorus fecal concentration (mg/g DM) | | | | |
| Wt | | | 14.3 | 11.5 |
| Y48H/D92Y/E100W/K139C/I201C/A217G/K234V/N247D/Q256D/H363R | | 13.7 | 12.6 | 11.5 |
| Y48H/D92Y/E100W/K139C/T152I/I201C/A217G/K234V/N247D/H363R | | 14.5 | 13.9 | 11.0 |
| Control | 18.3 | | | |
| (b) Phosphorus apparent fecal digestibility (%) | | | | |
| Wt | | | 47.3 | 50.1 |
| Y48H/D92Y/E100W/K139C/I201C/A217G/K234V/N247D/Q256D/H363R | | 44.1 | 55.3 | 58.0 |
| Y48H/D92Y/E100W/K139C/T152I/I201C/A217G/K234V/N247D/H363R | | 43.1 | 48.6 | 51.4 |
| Control | 27.9 | | | |
| (c) Phosphorus excretion (mg/g DM) | | | | |
| Wt | | | 2.06 | 1.93 |
| Y48H/D92Y/E100W/K139C/I201C/A217G/K234V/N247D/Q256D/H363R | | 2.14 | 1.74 | 1.61 |
| Y48H/D92Y/E100W/K139C/T152I/I201C/A217G/K234V/N247D/H363R | | 2.16 | 1.97 | 1.81 |
| Control | 2.80 | | | |
| (d) Phosphorus absorption (mg/g) | | | | |
| Wt | | | 1.85 | 1.94 |
| Y48H/D92Y/E100W/K139C/I201C/A217G/K234V/N247D/Q256D/H363R | | 1.69 | 2.16 | 2.22 |
| Y48H/D92Y/E100W/K139C/T152I/I201C/A217G/K234V/N247D/H363R | | 1.63 | 1.86 | 1.91 |
| Control | 1.09 | | | |
| (e) Phosphorus equivalences (mg/g) | | | | |
| Wt | | | 0.77 | 0.86 |
| Y48H/D92Y/E100W/K139C/I201C/A217G/K234V/N247D/Q256D/H363R | | 0.61 | 1.07 | 1.14 |
| Y48H/D92Y/E100W/K139C/T152I/I201C/A217G/K234V/N247D/H363R | | 0.56 | 0.78 | 0.83 |
| Control | 0.00 | | | |
| (f) Calcium apparent digestibility (%) | | | | |
| Wt | | | 58.9 | 55.2 |
| Y48H/D92Y/E100W/K139C/I201C/A217G/K234V/N247D/Q256D/H363R | | 54.1 | 63.1 | 63.5 |
| Y48H/D92Y/E100W/K139C/T152I/I201C/A217G/K234V/N247D/H363R | | 53.2 | 55.3 | 57.9 |
| Control | 51.0 | | | |

The invention claimed is:

1. A non-naturally occurring phytase which has at least 80% identity to the sequence of amino acid residues 1-413 of SEQ ID NO:2 and which comprises a set of modifications selected from the group consisting of:
   a. S 1QGPS/K26H/E54C/A101C/K139C/Q162N/G186S/I201C/K207Q/G346S,
   b. Q9S/N78Q/A89A/D92Y/H115M/A132V/K139C/Q162R/Q181L/I201C/A217G/K234V/P348R,
   c. D33C/E54C/A101C/Y179C,
   d. T35A/Y48H/E54C/P75N/K76N/D77Q/N78T/D92Y/A101C/K139C/T152A/I201C/A217G/K234V/N247D/R289W/H363R,
   e. Y48H/E54C/D92Y/A101C/K139C/T152A/I201C/K207Q/V208T/A217G/K234V/N247D/R289W/H363R,
   f. Y48H/E54C/D92Y/A101C/K139C/T152A/I201C/V208T/A217G/K234V/N247D/R289W/H363R,
   g. Y48H/E54C/D92Y/A101C/K139C/T152A/I201C/A217G/K234V/N247D/R289W/H363R,
   h. Y48H/E54C/D92Y/A101C/K139C/T152A/I201C/A217G/K234V/N247W/R289W/H363R,
   i. Y48H/E54C/D92Y/A101C/K139C/I201C/A217G/K234V/N247D/R289W/H363R,
   j. Y48H/E54C/D92Y/A101C/K139C/I201C/A217G/K234V/N247W/R289W/H363R,
   k. Y48H/D92Y/E100W/K139C/T152A/I201C/A217G/K234V/N247W/Q256D/H363R,
   l. Y48H/D92Y/E100W/K139C/T152I/I201C/A217G/K234V/N247D/H363R,
   m. Y48H/D92Y/E100W/K139C/I201C/V208T/A217G/K234V/N247D/Q256D/H363R,
   n. Y48H/D92Y/E100W/K139C/I201C/A217G/K234V/N247D/Q256D/H363R,
   o. Y48H/D92Y/E100W/K139C/I201C/A217G/K234V/N247D/R289W/H363R,
   p. Y48H/D92Y/E100W/K139C/I201C/A217G/K234V/N247W/Q256D/H363R,
   q. E54C/D92Y/A101C/K139C/I201C/A217G/K234V/N247D/Q256D/H363R,
   r. E54C/D92Y/A101C/K139C/I201C/A217G/H363R,
   s. E540/A101C/V130L/M137L/V146I/I201V/M260L/I266V/K207Q,
   t. E54C/A101C/K139C/I201C,
   u. E54C/A101C/K139C/I201C/K207Q,
   v. P75N/K76N/D77Q/N78T/D92Y/E100W/K139C/I201C/A217G/K234V/N247D/Q256D/H363R,
   w. D92Y/E100W/K139C/D173N/P175S/I201C/A217G/K234V/N247D/Q256D/H363R,
   x. D92Y/E100W/K139C/I201C/A217G/K234V/N247D/H363R, and
   y. D92Y/E100W/K139C/I201C/A217G/K234V/N247W/Q256D/H363R, wherein each position corresponds to the position of the phytase with the sequence of amino acids 1-413 of SEQ ID NO:2.

2. The phytase of claim 1, which has at least 85% identity to the sequence of amino acid residues 1-413 of SEQ ID NO:2.

3. The phytase of claim 1, which has at least 90% identity to the sequence of amino acid residues 1-413 of SEQ ID NO:2.

4. The phytase of claim 1, which has at least 95% identity to the sequence of amino acid residues 1-413 of SEQ ID NO:2.

5. The phytase of claim 1, which has at least 97% identity to the sequence of amino acid residues 1-413 of SEQ ID NO:2.

6. The phytase of claim 1, which is a variant of the parent phytase of SEQ ID NO:2.

7. The phytase of claim 1, which has an improved property as compared to the parent phytase in respect of thermal performance, including heat-stability, temperature stability, thermostability, steam stability, pelleting stability, and/or temperature profile and/or an improved efficiency, including an improved pH profile, an improved specific activity, an altered glycosylation pattern, an improved performance in animal feed, and/or which incorporates a change of a potential protease cleavage site and/or glycation site.

8. A composition comprising the phytase of claim 1, and (a) at least one fat soluble vitamin; (b) at least one water soluble vitamin; and/or (c) at least one trace mineral.

9. The composition of claim 8, further comprising at least one enzyme selected from the group consisting of amylase, galactanase, alpha-galactosidase, beta-glucanase, phosphatase, phospholipase, phytase, protease, and xylanase.

10. The composition of claim 8, which is an animal feed additive.

11. An animal feed composition having a crude protein content of 50 to 800 g/kg and comprising the phytase of claim 1.

12. A process for improving the nutritional value of an animal feed, comprising adding the phytase of claim 1 to the animal feed.

13. A process for reducing phytate levels in animal manure, comprising feeding an animal with an effective amount of the feed composition of claim 11.

14. A process for the treatment of vegetable proteins, comprising adding the phytase of claim 1 to at least one vegetable protein or protein source.

15. A process for producing a fermentation product, comprising
   (a) fermenting using a fermenting microorganism a carbohydrate containing material in the presence of the phytase of claim 1; and
   (b) recovering the fermentation product.

16. The process of claim 15, wherein the fermentation product is ethanol, beer, wine, or distillers dried grains (DDG).

\* \* \* \* \*

UNITED STATES PATENT AND TRADEMARK OFFICE
CERTIFICATE OF CORRECTION

PATENT NO. : 8,507,240 B2  Page 1 of 1
APPLICATION NO. : 13/472822
DATED : August 13, 2013
INVENTOR(S) : Lassen et al.

It is certified that error appears in the above-identified patent and that said Letters Patent is hereby corrected as shown below:

In the Claims

Please amend Claim 1, at column 71, lines 64-65 as follows:

s.  ~~E540~~E54C/A101C/V130L/M137L/V146I/I201V/M260L/I266V/K207Q,

Signed and Sealed this
Twelfth Day of November, 2013

Teresa Stanek Rea
*Deputy Director of the United States Patent and Trademark Office*